United States Patent
Frohberg

(10) Patent No.: US 8,304,606 B2
(45) Date of Patent: Nov. 6, 2012

(54) GENETICALLY MODIFIED PLANTS WHICH SYNTHESIZE A STARCH HAVING INCREASED SWELLING POWER

(75) Inventor: Claus Frohberg, Kleinmachnow (DE)

(73) Assignee: Bayer Cropscience AG, Monheim am Rhein (DE)

( * ) Notice: Subject to any disclaimer, the term of this patent is extended or adjusted under 35 U.S.C. 154(b) by 439 days.

(21) Appl. No.: 12/376,713

(22) PCT Filed: Aug. 9, 2007

(86) PCT No.: PCT/EP2007/007282
§ 371 (c)(1),
(2), (4) Date: Feb. 6, 2009

(87) PCT Pub. No.: WO2008/017518
PCT Pub. Date: Feb. 14, 2008

(65) Prior Publication Data
US 2010/0034953 A1    Feb. 11, 2010

Related U.S. Application Data

(60) Provisional application No. 60/836,817, filed on Aug. 10, 2006.

(30) Foreign Application Priority Data

Aug. 9, 2006   (EP) ..................................... 06090134

(51) Int. Cl.
*A01H 5/00* (2006.01)
*A01H 5/10* (2006.01)
*C12N 15/82* (2006.01)

(52) U.S. Cl. ..................... 800/284; 800/298; 800/320.1; 435/468; 435/419

(58) Field of Classification Search .......................... None
See application file for complete search history.

(56) References Cited

U.S. PATENT DOCUMENTS

| | | | |
|---|---|---|---|
| 4,280,851 A | 7/1981 | Pitchon et al. | |
| 299,907 A1 | 10/2001 | Seib et al. | |
| 6,734,340 B2 * | 5/2004 | Schewe et al. | 800/284 |

FOREIGN PATENT DOCUMENTS

| | | |
|---|---|---|
| WO | WO 9745545 A1 * | 12/1997 |
| WO | WO 2002/34923 | 5/2002 |
| WO | WO 0234923 A2 * | 5/2002 |
| WO | WO 2004/1056999 | 7/2004 |
| WO | WO 2005/1002359 | 1/2005 |
| WO | WO 2005/1095617 | 10/2005 |

OTHER PUBLICATIONS

Mikkelsen et al, Functional characterization of α-glucan, water dikinase, the starch phosphorylating enzyme, Biochem J (2004) 377(2), 525-532.*
Singh et al, Relationship between various physicochemical, thermal and rheological properties of starches separated from different potato cultivars, J Sci Food Agric (2004), 84: 714-720.*
Tester and Karkalas, Swelling and Gelatinization of Oat Starches, 1996, 73: 271-277.*
Leach, et al. (1959) "Structure of the Starch Granule." Cereal Chemistry 36: 534-544.
Li, et al. (2003) "The structural organisation of the gene encoding class II starch synthase of wheat and barley and the evolution of the genes encoding starch synthases in plants." Funct. Integr Genomics 3 76-85.
Ball and Morell, (2003) Ann. Rev Plant Biol. 54: 207-233.
Baunsgaard, et al. (2005) Plant Journal 41: 595-605.
Blennow, et al. (2000) Int. Journal of Biol. Macromolecules 27: 211-218.
Blennow, et al. (2000) Carbohydrate Polymers 41: 163-1 74.
Blennow, et al. (2005) Int. Journal of Blol. Macromolecules 36(3): 159-168.
Chen, et al. (2003) Starch/Starke 55: 203-212.
Jane, et al. (1996) Cereal Foods World 41(11): 827-832.
Kotting, et al. (2005) Plant Physiology 137(I):242-252.
Liu, et al. (1999) Starch/Starke 51(7): 249-252.
Liu, et al. (2003) Funct. Integr. Genomics 3: 76-85.
Lorberth, et al. (1998) Nature Biotechnology 16: 473-477.
Mikkelsen, et al. (2004) Biochemical Journal 377(2): 525-532.
Morell, et al. (2003) Plant Journal 34(2):173-185.
Narayana and Moorthy (2002) Starch /Starke 54: 559-592.
Ritte, et al. (2002) PNAS 99(71): 66-71 71.
Ritte, et al. (2006) FEBS Letters 580: 4872-4876.
Shi, et al. (1998) Journal of Cereal Science 27:289-299.
Singh, et al. (2002) J. of the Science of Food and Agriculture 82: 1376-1383.
Sodhi and Singh (2003) Food Chemistry 80: 99-108.
Tabata and Hizukuir (1971) Starch/Starke 23(8): 267-27.
Takizawa, et al. (2004) Brazilian Archives of Biology and Technology 47(6): 921-931.
Tetlow, et al. (2004) Journal of Experimental Botany 55(406): 2131-2145.
Van Hung and Morita (2005) Starch/Starke 57: 413-420.
Yamamori and Quynh (2000) Theor. Appl. Genet 100: 23-28.
Yasui, et al. (2002) Starch / Starke 54(1): 179-184.
Waduge, et al. (2006) Food Research International 39(1): 59-77.
Gaspar et al., "Plant Hormones and Plant Growth Regulators in Plant Tissue Culture," In Vitro Cellular and Developmental Biology—Plant, vol. 32, pp. 272-289 (1996).

* cited by examiner

*Primary Examiner* — Eileen B O Hara
(74) *Attorney, Agent, or Firm* — Hunton & Williams LLP

(57) ABSTRACT

The present invention relates to genetically modified plant cells and plants, and to processes for the production of genetically modified plant cells and plants which have an increased activity of a protein having the activity of a starch synthase II and an increased activity of a protein having the activity of a glucan-water dikinase. Plants of this type synthesize starches having increased hot water swelling power. The present invention likewise relates to starches having increased hot water swelling power, and to processes for their production.

33 Claims, 5 Drawing Sheets

Determination of SS2 activity in Transgenic Lines

GENETICALLY MODIFIED PLANTS WHICH SYNTHESIZE A STARCH HAVING INCREASED SWELLING POWER

CROSS-REFERENCE TO RELATED APPLICATIONS

This application is the U.S. National Stage filing of International Patent Application No. PCT/EP2007/007282, filed Aug. 9, 2007, which claims priority to EP 060 90 134.5, filed Aug. 9, 2006 and U.S. Provisional Patent Application No. 60/836,817, filed Aug. 10, 2006, the disclosures of each of which are hereby incorporated by reference.

BACKGROUND OF THE INVENTION (i) Field of the Invention

The present invention relates to genetically modified plant cells and plants, and to processes for the production of genetically modified plant cells and plants which have an increased activity of a protein having the activity of a starch synthase II and an increased activity of a protein having the activity of a glucan-water dikinase. Plants of this type synthesize starches having increased hot water swelling power. The present invention likewise relates to starches having increased hot water swelling power, and to processes for their preparation.

(ii) Description of the Related Art

Beside oils, fats and proteins, polysaccharides are the main renewable raw materials of plants. Starch, which is one of the most important reserve substances in higher plants, beside cellulose, takes on a central role in the polysaccharides.

Furthermore, starch is an essential constituent of human and animal nutrition in nutritional physiology terms. The structural features of the starch contained in foods can influence the functional (e.g. water-binding power, swelling power), nutritional physiology (e.g. digestibility, influence of the food on the glycemic index) or structure-imparting (e.g. cut resistance, texture, stickiness, processability) properties of all sorts of foods. Food compositions therefore often contain a starch having certain structural features which determine the desired properties of the food in question. The properties of foods containing starch-storing plant tissue (e.g. grains, fruit, flours) can also be influenced by the starch contained in the plant tissues.

The polysaccharide starch is a polymer of chemically homogeneous basic structural units, the glucose molecules. What is involved here, however, is a very complex mixture of different molecular forms, which differ with respect to their degree of polymerization, the occurrence of branchings of the glucose chains and their chain lengths, and which can moreover be modified, e.g. phosphorylated. Starch is therefore not a homogeneous raw material. In particular, amylose, an essentially unbranched polymer of alpha-1,4-glycosidically linked glucose molecules, is distinguished from amylopectin, which is a complex mixture of differently branched glucose chains. The branchings come about here as a result of the occurrence of additional alpha-1,6-glycosidic linkages. In typical plants used for industrial starch production or as foods, such as, for example, corn, rice, wheat or potatoes, the synthesized starch consists to about 20%-25% of amylose and to about 70%-75% of amylopectin.

The functional, nutritional physiology or structure-imparting properties of the starch, such as, for example, the solubility, the retrogradation behavior, the water-binding capacity, the film formation properties, the viscosity, the gelatinization properties, the freeze-thaw stability, the acid stability, the gel strength, the swelling power, the digestibility and the starch granule size of starches are influenced, among other things, by the structural features of the starch such as the amylose/amylopectin ratio, the molecular weight of the glucose polymers, the pattern of side chain distribution, the content of ions, the lipid and protein content and/or the starch granule morphology etc.

By means of processes based on breeding, selected structural features of the starch and thus also functional, nutritional physiology or structure-imparting properties of starch in plant cells can be altered. However, this is only possible today for selected structural features of starch (e.g. amylopectin/amylose content, U.S. Pat. No. 5,300,145). At present, for example, it is not possible to influence the content of phosphate in plant starch alone by breeding measures.

An alternative to breeding processes consists in the selected modification of starch-producing plants by genetic engineering methods. A prerequisite for this, however, is the identification and characterization of the enzymes involved in starch synthesis and/or starch modification and their subsequent functional analysis in transgenic plants.

Various enzymes which catalyze different reactions are involved in starch synthesis in plant cells. Starch synthases (EC2.4.1.21, ADP-glucose, 1,4-alpha-D-glucan 4-alpha-D-glucosyltransferase) catalyze a polymerization reaction by transfer of a glucosyl radical of ADP-glucose to alpha-1,4-glucans, the transferred glucosyl radical being linked to the alpha-1,4-glucan by production of an alpha-1,4 bond. In almost all plants investigated up to now, it was possible in each case to demonstrate a number of isoforms of starch synthases. Starch synthases can be divided into two different groups: granule-bound starch synthases (GBSS) and soluble starch synthases (also abbreviated as "SS" in connection with the present invention). Granule-bound starch synthases catalyze the synthesis of amylose, whereas soluble starch synthases are involved in the synthesis of amylopectin (Ball and Morell, 2003, Annu. Rev, Plant Biol. 54, 207-233; Teltow et al., 2004, J. Expt. Bot. 55(406), 2131-2145). The group of soluble starch synthases has a number of isoforms which are designated in the technical literature as SSI, SSII, SSIII, SSIV. The assignment of starch synthases to the individual groups (SSI, SSII, SSIII, SSIV) is carried out by means of sequence homologies of the protein sequences of the respective enzymes in question (Ball and Morell, 2003, Annu. Rev, Plant Biol. 54, 207-233). Each individual isoform of the soluble starch synthases is assigned a specific function in starch synthesis according to current doctrine. In dicotyledonous plants, up to now it was only possible to demonstrate one isoform of SSII proteins, whereas in many monocotyledonous plants (e.g. corn) two different classes of SSII proteins were demonstrated, which are designated by SSIIa or SSIIb. In monocotyledonous plants, SSIIa is expressed preferentially in the endosperm and SSIIb preferably in the leaf tissue (Teltow et al., 2004, J. Expt. Bot. 55(406), 2131-2145). The specific function, in particular of the individual soluble starch synthases in the synthesis of starch, is at present still not finally clarified (Ball and Morell, 2003, Annu. Rev, Plant Biol. 54, 207-233).

The functional, nutritional physiology or structure-imparting properties of starch are also influenced by the phosphate content, a non-carbon component of starch. A distinction is to be made here between phosphate which is covalently bonded to the glucose molecule of the starch in the form of monoesters (in connection with the present invention designated as starch phosphate) and phosphate in the form of phospholipids associated with the starch.

The content of starch phosphate varies depending on the type of plant. For instance, certain corn mutants synthesize a starch having an increased content of starch phosphate (waxy corn 0.002% and high amylose corn 0.013%), while conventional types of corn only contain traces of starch phosphate. Likewise, small amounts of starch phosphate are found in wheat (0.001%) while in oats and *Sorghum* it was not possible to detect any starch phosphate. Less starch phosphate was likewise found in rice mutants (waxy rice 0.003%) than in conventional types of rice (0.013%). Significant amounts of starch phosphate were found in plants synthesizing tuber or root store starch such as, for example, tapioca (0.008%), sweet potato (0.011%), arrowroot (0.021%) or potato (0.089%). The percentage values for the starch phosphate content cited in the preceding text in each case relate to the dry weight of the starch and have been determined by Jane et al. (1996, Cereal Foods World 41 (11), 827-832).

Starch phosphate can be present in the form of monoesters in the C2, C3 or C6 position of the polymerized glucose monomers (Takeda and Hizukuri, 1971, Starch/Stärke 23, 267-272). The phosphate distribution of the phosphate in starch synthesized by plants is distinguished in general in that approximately 30% to 40% of the phosphate radicals in the C3 position and approximately 60% to 70% of the phosphate radicals in the C6 position of the glucose molecules are covalently bonded (Blennow et al., 2000, Int. J. of Biological Macromolecules 27, 211-218). Blennow et al. (2000, Carbohydrate Polymers 41, 163-174) determined a content of starch phosphate which is bonded in the C6 position of the glucose molecules for various starches, such as, for example, potato starch (between 7.8 and 33.5 nmol per mg of starch, depending on cultivar), starch from various *Curcuma* species (between 1.8 and 63 nmol per mg, depending on cultivar), tapioca starch (2.5 nmol per mg of starch), rice starch (1.0 nmol per mg of starch), mung bean starch (3.5 nmol per mg of starch) and sorghum starch (0.9 nmol per mg of starch). In barley starch and starch from various waxy mutants of corn, these authors were not able to detect any starch phosphate bonded in the C6 position. Up to now, it has not been possible to make any connection between the genotype of a plant and the content of starch phosphate (Jane et al., 1996, Cereal Foods World 41 (11), 827-832). Therefore it is not possible at present to influence the content of starch phosphate in plants by breeding measures.

Up to now, two proteins have been described which mediate the introduction of covalent bonds of phosphate radicals into the glucose molecules of starch. The first protein has the enzymatic activity of an alpha-glucan-water dikinase (GWD, E.C.: 2.7.9.4) (Ritte et al., 2002, PNAS 99, 7166-7171), is often called R1, in particular in the older scientific literature, and is bonded to the starch granules of the reserve starch in potato tubers (Lorberth et al., 1998, Nature Biotechnology 16, 473-477). The second protein described in the literature, which catalyzes the introduction of starch phosphate into starch, has the enzymatic activity of a phosphoglucan-water dikinase (PWD, E.C.: 2.7.9.5) (Kötting et al., 2005, Plant Physiol. 137, 2424-252, Baunsgaard et al., 2005, Plant Journal 41, 595-605).

A significant difference between GWD and PWD consists in the fact that GWD can use unphosphorylated starch as a substrate, i.e. a de novo phosphorylation of unphosphorylated starch can be catalyzed by GWD, whereas PWD needs already phosphorylated starch as a substrate, i.e. additionally introduces phosphate into already phosphorylated starch (Kötting et al., 2005, Plant Physiol. 137, 2424-252, Baunsgaard et al., 2005, Plant Journal 41, 595-605). A further significant difference between GWD and PWD consists in the fact that GWD introduces phosphate groups exclusively into the C6 position of the glucose molecules of starch, whereas PWD exclusively phosphorylates the C3 position of the glucose molecules of phosphorylated starch (Ritte et al., 2006, FEBS Letters 580, 4872-4876).

In the reaction catalyzed by GWD or PWD, the starting materials alpha-1,4-glucan (for GWD) or phosphorylated alpha-1,4-glucan (for PWD), adenosine triphosphate (ATP) and water are reacted to give the products glucan phosphate (starch phosphate), monophosphate and adenosine monophosphate (Kötting et al., 2005, Plant Physiol. 137, 2424-252, Ritte et al., 2002, PNAS 99, 7166-7171).

Wheat plants which have an increased activity of GWD proteins due to expression of a GWD-encoding gene from potato are described in WO 02 34923. In comparison to corresponding wild-type plants in which it was not possible to detect any starch phosphate, these plants synthesize a starch containing significant amounts of starch phosphate in the C6 position of the glucose molecules.

WO 05 2359 describes the overexpression of a GWD from potato in corn plants, optimized with respect to codons used by corn plants. By means of $^{31}P$ NMR, a total phosphate content (bonded in the C6, C3 and C2 position of the glucose molecules) of the corn starch in question of 0.0736% phosphate based on the amount of glucose was determined. If a molecular weight of 98 is taken as a basis for phosphate, a total phosphate content of about 7.5 nmol of phosphate per mg of starch results for the total phosphate content determined in WO 05 2359 of 0.0736% for starch isolated from transgenic corn plants.

Plants which have an increased activity of a PWD protein due to overexpression of a PWD-encoding gene from *Arabidopsis thaliana* are described in WO 05 095617. In comparison to corresponding untransformed wild-type plants, these plants have an increased content of starch phosphate.

An important functional property, for example in the processing of starches in the food industry, is the swelling power. Various structural properties of starches, such as the amylose/amylopectin ratio, the side chain length, the molecular weight, the number of branchings, have an influence on the swelling power of the starches in question (Narayana and Moorthy, 2002, Starch/Stärke 54, 559-592).

The advice can be taken from the scientific literature that, in addition to the amylose/amylopectin ratio, the side chain distribution of the amylopectin and the molecular weight distribution of the starch polymers, also the amount of starch phosphate, has an influence on functional properties, in particular on the swelling power of the starch (Narayana and Moorthy, 2002, Starch/Stärke 54, 559-592).

It is to be emphasized that concerning the swelling power of starch a distinction is to be made between the swelling power in cold water (e.g. room temperature) and the swelling power in warm or hot water. Native starches have a negligible swelling power, if at all, in cold water, whereas physically modified (pregelatinized, dried) starches are already able to swell in cold water. Production processes for starches swelling in cold water are described, for example, in U.S. Pat. No. 4,280,851. In connection with the present invention, the term "swelling power" relates to the behavior of starch in warm/hot aqueous suspensions. The swelling power is standardly determined by warming starch granules in the presence of an excess of water, removing unbound water after centrifugation of the suspension and forming the quotient of the weight of the residue obtained and the weight of the amount of starch weighed in. When carrying out this process, on warming the starch suspension crystalline areas of the starch granules are dissolved and water molecules are intercalated in the starch granules, but without the structure of the starch granules itself being destroyed here, i.e. only a swelling of the individual starch granules, caused by the absorption of water molecules, takes place.

In comparison to cereal starches, starches isolated from tubers or tuberous tissues have a significantly higher hot water swelling power.

For potato starches isolated from various varieties, a maximum swelling power of 74.15 g/g (Kufri Jyoti variety) was determined at 85° C. (Singh et al., 2002, Journal of the Science of Food and Agriculture 82, 1376-1383) according to the method of Leach et al. (1959, Cereal Chemistry 36, 534-544). Takizawa et al. (2004, Brazilian Archives of Biology and Technology 47 (6), 921-931) determined a swelling power of 100 g/g for potato starch (90° C., according to the method of Leach et al. (1959, Cereal Chemistry 36, 534-544)). Wheat starch, isolated from various cultivars, has a swelling power of 16.6 g/g to 26.0 g/g (temperature: boiling aqueous 0.1% $AgNO_3$ suspension) (Yamamori and Quynh, 2000, Theor Appl Genet 100, 23-28). Starch isolated from various cultivars of hull-less barley has a swelling power of 16.5 g/g or 19.3 g/g and waxy or amylose-free starch of the various cultivars of said barley has a swelling power of 36.0 g/g to 55.7 g/g (temperature: 70° C. aqueous 0.1% $AgNO_3$, Yasui et al., 2002, Starch/Stärke 54, 179-184). For corn starch, a swelling power of 22.3 g/g and for high amylose corn starches a swelling power of 9.6 g/g (Hylon V), 6.1 g/g (Hylon VII) or 3.9 g/g (LAPS=Low AmyloPectin Starch) was determined (90° C., Shi et al., 1998, J. Cereal Sci. 27, 289-299). In U.S. Pat. No. 6,290 9,907, a swelling power of 35.4 g/g was indicated for waxy corn starch. For starch isolated from various rice cultivars, a swelling power of 26.0 g/g to 33.2 g/g was determined (Sodhi and Singh, 2003, Food Chemistry 80, 99-108) according to the method of Leach et al. (1959, Cereal Chemistry 36, 534-544). Chen et al. (2003, Starch/Stärke 55, 203-212) determined a swelling power of approximately 25 g/g to approximately 49 g/g (95° C., aqueous suspension) for various mixtures of waxy rice starches with high-amylose rice starches. Yasui et al. (2002, Starch/Stärke 54, 179-184) determined a swelling power of 55.7 g/g (measured in boiling water in 0.1% aqueous silver nitrate solution) for an amylose-free rice starch.

By the preparation of derivatives of native starches, functional properties of the starches can be altered. "Cross-linked" wheat starches, depending on the degree of cross-linking, have a swelling power of 6.8 g/g to 8.9 g/g, acetylated wheat starches have a swelling power of at most 10.3 g/g and at the same time cross-linked and acetylated wheat starches have a swelling power of 9.4 g/g, whereas the corresponding underivatized starches had a swelling power of 8.8 g/g (measured at 90° C.; Van Hung and Morita, 2005, Starch/Stärke 57, 413-420).

For acetylated waxy rice starches, a swelling power of about 30 g/g and for cross-linked waxy rice starch a swelling power of about 15 g/g was determined, whereas corresponding underivatized waxy rice starch had a swelling power of about 41 g/g. Acetylated rice starch had a swelling power of about 20 g/g and cross-linked rice starch had a swelling power of about 13 g/g, whereas corresponding underivatized rice starch had a swelling power of about 14 g/g (measured at 90° C., Liu et al., 1999, Starch/Stärke 52, 249-252). U.S. Pat. No. 6,299,907 describes cross-linked starches, the cross-linking reaction being carried out after pre-swelling of the starches in question in a sodium hydroxide/sulfate solution. Depending on the degree of crosslinkage, for wheat starch a swelling power of 6.8 g/g to 7.3 g/g (corresponding underivatized wheat starch 14.7 g/g), for hydroxypropyl-wheat starch a swelling power of 9.7 g/g (corresponding underivatized wheat starch 22.9 g/g), for cross-linked corn starch a swelling power of 5.9 g/g (corresponding underivatized corn starch 16.7 g/g), for cross-linked waxy corn starch a swelling power of 8.3 g/g (corresponding underivatized waxy corn starch 35.4 g/g) and for cross-linked potato starch a swelling power of 6.7 g/g (corresponding underivatized potato starch was not accurately specified) was determined (measured at 95° C.). It results from this that the swelling power of starch cannot be increased significantly, if at all, by methods of derivatization customary nowadays.

SUMMARY OF THE INVENTION

The present invention is based on the object of making available modified starches having altered functional properties, and plant cells and plants which synthesize a starch having altered functional properties, and processes and means for the production of said plants and/or plant cells.

DETAILED DESCRIPTION OF THE INVENTION

The present invention thus relates to genetically modified plant cells and genetically modified plants which have an increased activity of a protein having the activity of a starch synthase II and an increased activity of a protein having the activity of a glucan-water dikinase, in comparison to corresponding genetically unmodified wild-type plant cells or wild-type plants.

A first aspect of the present invention relates to a plant cell or a plant which is genetically modified, the genetic modification leading to the increase in the activity of at least one protein having the activity of a starch synthase II and at the same time to the increase in the activity of at least one protein having the activity of a glucan-water dikinase, in comparison to corresponding wild-type plant cells or wild-type plants which are not genetically modified.

The genetic modification can here be any genetic modification which leads to an increase in the activity of at least one protein having the activity of a starch synthase II and (at the same time) at least one protein having the activity of a glucan-water dikinase in genetically modified plant cells or genetically modified plants, in comparison to corresponding wild-type plant cells or wild-type plants which are not genetically modified.

The term "wild-type plant cell" means, in connection with the present invention, that these are plant cells which served as a starting material for the production of the plant cells according to the invention, i.e. their genetic information, apart from the genetic modification introduced, corresponds to that of a plant cell according to the invention.

In connection with the present invention, the term "wild-type plant" means that these are plants which served as a starting material for the production of the plants according to the invention, i.e. their genetic information, apart from the genetic modification introduced, corresponds to that of a plant according to the invention.

The term "corresponding" means, in connection with the present invention, that on comparison of a number of articles, the articles in question which are being compared with one another were kept under identical conditions. In connection with the present invention, the term "corresponding" in connection with a wild-type plant cell or wild-type plant means that the plant cells or plants which are being compared with one another were grown under identical culture conditions and that they have an identical (cultivation) age.

The term "increased activity of at least one protein having the activity of a starch synthase II" here means, in the context of the present invention, an increase in the expression of endogenous genes which encode proteins having the activity of a starch synthase II and/or an increase in the amount of proteins having the activity of a starch synthase II in the cells and/or an increase in the enzymatic activity of proteins having the activity of a starch synthase II in the cells.

The term "increased activity of a protein having the activity of a glucan-water dikinase" here means, in the context of the present invention, an increase in the expression of endogenous genes which encode proteins having the activity of a glucan-water dikinase and/or an increase in the amount of proteins having the activity of a glucan-water dikinase in the cells and/or an increase in the enzymatic activity of proteins having the activity of a glucan-water dikinase in the cells.

The increase in the expression can be determined, for example, by measurement of the amount of transcripts which encode proteins having the activity of a starch synthase II or which encode proteins having the activity of a glucan-water dikinase. This can be carried out, for example, by Northern blot analysis or RT-PCR. An increase in the amount of transcripts which encode a protein having the activity of a starch synthase II here preferably means an increase in the amount of transcripts in comparison to corresponding cells which are not genetically modified by at least 100%, in particular by at least 125%, preferably by at least 150% and particularly preferably by at least 200%. An increase in the amount of transcripts encoding a protein having the activity of a starch synthase II also means that plants or plant cells which contain no detectable amounts of transcripts encoding a protein having the activity of a starch synthase II contain, after genetic modification according to the invention, detectable amounts of transcripts encoding a protein having the activity of a starch synthase II.

An increase in the amount of transcripts which encode a protein having the activity of a glucan-water dikinase here preferably means an increase in the amount of transcripts in comparison to corresponding cells which are not genetically modified by at least 50%, in particular by at least 70%, preferably by at least 85% and particularly preferably by at least 100%.

An increase in the amount of transcripts encoding a protein having the activity of a glucan-water dikinase also means that plants or plant cells which contain no detectable amounts of transcripts encoding a protein having the activity of a glucan-water dikinase, after genetic modification according to the invention, contain detectable amounts of transcripts encoding a protein having the activity of a glucan-water dikinase.

The increase in the amount of protein having the activity of a starch synthase II or having the activity of a glucan-water dikinase which has an increased activity of these proteins in the plant cells in question as a result, can be determined, for example, by immunological methods such as Western blot analysis, ELISA (enzyme linked immunosorbent assay) or RIA (radioimmunoassay). An increase in the amount of a protein having the activity of a starch synthase II here preferably means an increase in the amount of protein in question in comparison to corresponding cells which are not genetically modified by at least 100%, in particular by at least 125%, preferably by at least 150% and particularly preferably by at least 200%. An increase in the amount of proteins having the activity of a starch synthase II also means that plants or plant cells which contain no detectable amounts of protein having the activity of a starch synthase II contain, after genetic modification according to the invention, a detectable amount of protein having the activity of a starch synthase II.

An increase in the amount of a protein having the activity of a glucan-water dikinase here preferably means an increase in the amount of protein in question in comparison to corresponding cells which are not genetically modified, by at least 50%, in particular by at least 70%, preferably by at least 85% and particularly preferably by at least 100%.

An increase in the amount of protein having the activity of a glucan-water dikinase also means that plants or plant cells which contain no detectable amounts of proteins having the activity of a glucan-water dikinase contain, after genetic modification according to the invention, a detectable amount of protein having the activity of a glucan-water dikinase.

Methods for the production of antibodies which react specifically with a certain protein, i.e. which specifically bind to said protein, are known to the person skilled in the art (see, for example, Lottspeich and Zorbas (Eds.), 1998, Bioanalytik [Bioanalytics], Spektrum akad. Velag, Heidelberg, Berlin, ISBN 3-8274-0041-4). The production of antibodies of this type is offered as contract service by some firms (e.g. Eurogentec, Belgium). Antibodies with which an increase in the amount of protein having the activity of a glucan-water dikinase can be detected by means of immunological methods are described in Lorberth et al. (1998, Nature Biotechnology 16, 473-477) and Ritte et al. (2000, Plant Journal 21, 387-391). Antibodies with which an increase in the amount of protein having the activity of a starch synthase II can be determined by means of immunological methods are described in Walter ("Untersuchungen der Expression und Funktion der Stärkesynthase II (SS II) aus Weizen (*Triticum aestivum*)" [Investigations of the expression and function of starch synthase II (SS II) from wheat (*Triticum aestivum*)], dissertation in the faculty of Biology of the University of Hamburg, ISBN 3-8265-8212-8).

The amount of activity of a protein having the activity of a glucan-water dikinase can be detected, for example, as described in the literature (Mikkelsen et al., 2004, Biochemical Journal 377, 525-532; Ritte et al., 2002, PNAS 99, 7166-7171).

The amount of activity of a protein having the activity of a starch synthase II can be determined, for example, as described in the literature (Nishi et al., 2001, Plant Physiology 127, 459-472). A preferred method for the determination of the amount of activity of a protein having the activity of a starch synthase II is described under general methods item 9.

Preferably, plant cells according to the invention or plants according to the invention have an activity of a protein having the activity of a starch synthase II, which is increased at least 6-fold, preferably at least 7-fold, particularly preferably at least 8-fold, especially preferably at least 9-fold, and very especially preferably at least 10-fold, in comparison to corresponding wild-type plant cells or wild-type plants which are not genetically modified.

Proteins having the activity of a starch synthase II (ADP-glucose-1,4-alpha-D-glucan-4-alpha-D-glucosyl transferase; EC 2.4.1.21) have a sequence of certain domains in their structure. At the N terminus, they have a signal peptide for transport in plastids. In the direction from the N-terminus to the C-terminus follow an N-terminal region and a catalytic domain. (Li et al., 2003, Funct Integr Genomics 3, 76-85). Further analyses, based on amino acid sequence comparisons available on the world wide web at hits.isb-sib.ch/cgi-bin/PFSCAN) of various proteins having the activity of a starch synthase II showed that these proteins have three specific domains. In the amino acid sequence shown under SEQ ID NO 6, the amino acids 322 to 351 represent domain 1, the amino acids 423 to 462 represent domain 2 and in the amino acids 641 to 705 represent domain 3. Domain 1 is encoded by the nucleotides 1190 to 1279, domain 2 is encoded by the nucleotides 1493 to 1612 and domain 3 is encoded by the nucleotides 2147 to 2350 of the nucleic acid sequence shown under SEQ ID NO 5.

In connection with the present invention, the term "protein having the activity of a starch synthase II" should be understood as meaning a protein that catalyzes a glycosylation reaction in which glucose molecules of the substrate ADP-glucose are transferred to alpha-1,4-linked glucan chains with formation of an alpha-1,4-linkage (ADP-glucose+{(1,4)-alpha-D-glucosyl}(N)<=>ADP+{(1,4)-alpha-D-glucosyl}(N+1)), where the amino acid sequence of the protein having the activity of a protein of a starch synthase II has an identity of at least 86%, preferably at least 93%, particularly preferably at least 95% with the amino acids 322 to 351 (domain 1) of the amino acid sequence shown under SEQ ID NO 6 and has an identity of at least 83%, preferably at least 86%, particularly preferably at least 95% with the amino acids 423 to 462 (domain 2) of the amino acid sequence shown under SEQ ID NO 6 and has an identity of at least 70%, preferably at least 82%, preferably 86%, particularly preferably 98%, in particular preferably of at least 95% with the amino acids 641 to 705 (domain 3) of the amino acid sequence shown under SEQ ID NO 6.

Nucleic acid sequences and the amino acid sequences corresponding thereto, which have said identity with the domains 1, 2 and 3 and encode a protein having the activity of a starch synthase II, are known to the person skilled in the art and are published, for example, under Accession No AY133249 (*Hordeum vulgate*), Accession No AY133248 (*Aegilops tauschii*), Accession Nos XP467757, AAK64284 (*Oryza sativa*), MK81729 (*Oryza sativa*), Accession Nos MD13341, MS77569, No AAD13342 (*Zea Mays*), Accession No MF13168 (*Manihot eculenta*), Accession No BAD18846 (*Phaseolus vulgaris*), Accession No CM61241 (*Solanum tuberosum*), Accession No CAA61269 (*Pisum sativum*), Accession No MC19119 (*Ipomea batatas*), Accession No MF26156 (*Arabidopsis thaliana*), Accession No AAP41030 (*Colocasia esculenta*), Accession No AAS 88880 (*Ostraeococcus taun*), or Accession No AAC17970 (*Chlamydomonas reinhardil*). The nucleic acid sequences and amino acid sequences mentioned encoding a protein having the activity of a starch synthase II are accessible by means of NCBI available on the world wide web at ncbi.nim.nih.gov/entrez/) and are expressly included in the description of the present application by mention of the references.

In the context of the present invention, the term "protein having the activity of a glucan-water dikinase" should be understood as meaning a protein which transfers a beta-phosphate residue from ATP to starch. Starches isolated from leaves of an *Arabidopsis thaliana* sex1-3 mutant have no detectable amounts of covalently bonded phosphate radicals, but are phosphorylated by a protein having the activity of a glucan-water dikinase. I.e. unphosphorylated starch, e.g. isolated from leaves of an *Arabidopsis thaliana* sex1-3 mutant, is used as a substrate in a phosphorylation reaction catalyzed by a protein having the activity of a glucan-water dikinase.

The beta-phosphate radical of the ATP is transferred from a protein having the activity of a glucan-water dikinase to the starch and the gamma-phosphate radical of the ATP is transferred to water. AMP (adenosine monophosphate) results as a further reaction product. A protein having the activity of a glucan-water dikinase is therefore also designated as [alpha-1,4-glucan]-water dikinase or as a starch-water dikinase (EC: 2.7.9.4; Ritte et al., 2002, PNAS 99, 7166-7171). In the phosphorylation of starch catalyzed by a protein having the activity of a glucan-water dikinase, additional phosphate monoester bonds result exclusively in the C6 position of the glucose molecules (Ritte et al., 2006, FEBS Letters 580, 4872-4876). In the catalysis of the phosphorylation reaction of a starch by a protein having the activity of a glucan-water dikinase, a phosphorylated protein in which the beta-phosphate radical of the ATP is bonded covalently to an amino acid of the protein having the activity of a glucan-water dikinase results as an intermediate (Ritte et al., 2002, PNAS 99, 7166-7171). The intermediate results by autophosphorylation of the protein having the activity of a glucan-water dikinase, i.e. the protein having the activity of a glucan-water dikinase itself catalyzes the reaction which leads to the intermediate. Amino acid sequences which encode proteins having the activity of a glucan-water dikinase contain a phosphohistidine domain. Phosphohistidine domains are described, for example, in Tien-Shin Yu et al. (2001, Plant Cell 13, 1907-1918). In the autophosphorylation of a protein having the activity of a glucan-water dikinase, a histidine radical in the phosphohistidine domain of the amino acid sequence encoding a protein having the activity of a glucan-water dikinase is phosphorylated (Mikkelsen et al., 2004, Biochemical Journal 377, 525-532). In the protein sequence of a protein having the activity of a glucan-water dikinase from *Solanum tuberosum* shown under SEQ ID NO 2, the amino acids 1064 to 1075 are the phosphohistidine domains. If the conserved histidine radical (in the protein sequence of amino acid 1069 shown, for example, under SEQ ID NO 2) of the phosphohistidine domains is replaced by another amino acid, autophosphorylation and thus also phosphorylation of glucans by the mutagenized protein no longer takes place (Mikkelsen et al., 2004, Biochemical Journal 377, 525-532). Furthermore, a protein having the activity of a glucan-water dikinase is distinguished in that it has a C-terminal nucleotide binding domain which is included in the amino acid sequence of the amino acids 1121 to 1464 shown, for example, under SEQ ID NO 2. A deletion of the nucleotide binding domain leads to the inactivation of a protein having the activity of a glucan-water dikinase (Mikkelsen and Blennow, 2005, Biochemical Journal 385, 355-361). On the N-terminus, proteins having the activity of a glucan-water dikinase contain a carbohydrate-binding domain (CBM) which is included in the amino acid sequence of the amino acids 78 to 362 shown under SEQ ID NO 2. Carbohydrate binding domains are distinguished, inter alia, in that their amino acid sequence contains conserved tryptophan residues. If these conserved amino acid residues are replaced by another amino acid, the carbohydrate binding domains lose their ability to bind glucans. For instance, replacement of the amino acids W139 or W194 in the amino acid sequence shown under SEQ ID NO 2 leads to a loss of the function of this carbohydrate binding domain. If the carbohydrate binding domain of a glucan-water dikinase is deleted (for example a deletion of the amino acids 1 to 362, where the amino acids 1 to 77 in the amino acid sequence shown under SEQ ID NO 2 are a plastidic signal peptide), this does not lead, however, to the inactivation of the phosphorylating activity of the enzyme (Mikkelsen et al., 2006, Biochemistry 45, 4674-4682).

Nucleic acid sequences and amino acid sequences corresponding to these, encoding a protein having the activity of a glucan-water dikinase, are described of different species, such as, for example, potato (WO 97 11188, GenBank Acc.: AY027522, Y09533), wheat (WO 00 77229, U.S. Pat. No. 6,462,256, GenBank Acc.: AAN93923, GenBank Acc.: AR236165), rice (GenBank Acc.: AAR61445, GenBank Acc.: AR400814), corn (GenBank Acc.: AAR61444, GenBank Acc.: AR400813), soybean (GenBank Acc.: AAR61446, GenBank Acc.: AR400815), *Curcuma longa* (SEQ ID NO 3), citrus (GenBank Acc.: AY094062), *Arabi*-

*dopsis* (GenBank Acc.: AF312027) and the green alga *Ostreococcus tauri* (GenBank Acc.: AY570720.1). The nucleic acid sequences and amino acid sequences mentioned encoding a protein having the activity of a glucan-water dikinase are published, inter alia, by the NCBI (available on the world wide web at www.ncbi.nlm.nih.gov/entrez/) and are expressly included in the description of the present application by mention of the references.

A further embodiment of the present invention relates to a genetically modified plant cell according to the invention or a genetically modified plant according to the invention, where the genetic modification consists in the introduction of at least one foreign nucleic acid molecule into the genome of the plant cell or into the genome of the plant.

In this connection, the term "genetic modification" means the introduction of homologous and/or heterologous foreign nucleic acid molecules into the genome of a plant cell or into the genome of a plant, where said introduction of these molecules leads to the increase in the activity of a protein having the activity of a glucan-water dikinase and to the increase in the activity of a protein having the activity of a starch synthase II.

By introduction of a foreign nucleic acid molecule, the plant cells according to the invention or plants according to the invention are altered in their genetic information. The presence or the expression of at least one foreign nucleic acid molecule leads to a phenotypic alteration. "Phenotypic" alteration here preferably means a measurable alteration of one or more functions of the cells. For example, the genetically modified plant cells according to the invention and the genetically modified plants according to the invention, on account of the presence or in the case of expression of introduced foreign nucleic acid molecules, show an increase in the activity of a protein having the activity of a glucan-water dikinase and an increase in the activity of a protein having the activity of a starch synthase II.

The term "foreign nucleic acid molecule" is understood in connection with the present invention as meaning a molecule of the type which either does not occur naturally in corresponding wild-type plant cells, or which does not occur naturally in wild-type plant cells in the actual spatial arrangement or which is located in a site in the genome of the wild-type plant cell in which it does not naturally occur. Preferably, the foreign nucleic acid molecule is a recombinant molecule which consists of various elements whose combination or specific spatial arrangement does not occur naturally in plant cells.

In principle, a foreign nucleic acid molecule can be any desired nucleic acid molecule which brings about an increase in the activity of a protein having the activity of a glucan-water dikinase and of a protein having the activity of a starch synthase II in the plant cell or plant.

The term "recombinant nucleic acid molecule" should be understood in connection with the present invention as meaning a nucleic acid molecule which contains different nucleic acid molecules which are not naturally present in a combination as is present in a recombinant nucleic acid molecule. Thus recombinant nucleic acid molecules, for example, in addition to nucleic acid molecules which encode a protein having the activity of a glucan-water dikinase and/or a protein having the activity of a starch synthase II, can contain additional nucleic acid sequences which are not naturally present in combination with the nucleic acid molecules mentioned. The additional nucleic acid sequences mentioned, which are present in a recombinant nucleic acid molecule in combination with a nucleic acid molecule encoding protein having the activity of a glucan-water dikinase or a protein having the activity of a starch synthase II, can here be any desired sequences. They can be, for example, genomic and/or plant nucleic acid sequences. Preferably, additional nucleic acid sequences mentioned are regulatory sequences (promoters, termination signals, enhancers), particularly preferably regulatory sequences which are active in plant tissue, in particular preferably tissue-specific regulatory sequences which are active in plant tissue. Methods for the production of recombinant nucleic acid molecules are known to the person skilled in the art and comprise genetic engineering methods, such as, for example, the connection of nucleic acid molecules by ligation, genetic recombination or the de novo synthesis of nucleic acid molecules (see, for example, Sambrook et al., Molecular Cloning, a Laboratory Manual, 3rd edition (2001) Cold Spring Harbor Laboratory Press, Cold Spring Harbor, N.Y. ISBN: 0879695773, Ausubel et al., Short Protocols in Molecular Biology, John Wiley & Sons; 5th edition (2002), ISBN: 0471250929).

The term "genome" should be understood in connection with the present invention as meaning the totality of the hereditary material present in a plant cell. It is known to the person skilled in the art that in addition to the cell nucleus other compartments (e.g. plastids, mitochondria) also contain hereditary material.

In a further embodiment, the plant cells according to the invention and the plants according to the invention are characterized in that at least one foreign nucleic acid molecule encodes a protein having the activity of a glucan-water dikinase. Preferably, the foreign nucleic acid molecules encoding a protein having the activity of a glucan-water dikinase are the nucleic acid molecules already mentioned and known to the person skilled in the art from the various plant species, particularly preferably nucleic acid molecules encoding a protein having the activity of a glucan-water dikinase from potato or *Curcuma longa*, in particular preferably a protein having the activity of a glucan-water dikinase which has the amino acid sequence shown under SEQ ID NO 2 or which is encoded by the nucleic acid sequence shown in SEQ ID NO 1.

The sequences shown under SEQ ID NO 3 and SEQ ID NO 4 are hitherto unpublished. Plant cells or plants, in particular rice plant cells or rice plants, which contain a foreign nucleic acid molecule encoding a protein having the activity of a glucan-water dikinase from *Curcuma longa*, are distinguished in that they synthesize a starch which has a higher starch phosphate content than plant cells or plants which contain a foreign nucleic acid molecule encoding a protein having the activity of a glucan-water dikinase from other species (e.g. potato).

The present invention therefore also relates to nucleic acid molecules encoding a protein having the activity of a glucan-water dikinase, chosen from the group consisting of
a) nucleic acid molecules which encode a protein having the amino acid sequence shown under SEQ ID NO 4;
b) nucleic acid molecules which encode a protein whose amino acid sequence contains at least 90%, preferentially of at least 93%, preferably of at least 96% and in particular preferably of at least 99% to the amino acid sequence shown under SEQ ID NO 4;
c) nucleic acid molecules which comprise the nucleic acid sequence shown under SEQ ID NO 3 or a complementary sequence;
d) nucleic acid molecules which have an identity with the nucleic acid sequence shown under SEQ ID NO 3 of at least 90%, preferentially of at least 93%, preferably of at least 96% and in particular preferably of at least 99%, e) nucleic acid molecules which hybridize under stringent conditions with at least one strand of the nucleic acid molecules described under a) or c);
f) nucleic acid molecules whose nucleotide sequence, on account of the degeneracy of the genetic code, differs from the sequence of the nucleic acid molecules mentioned under a), or c);
g) nucleic acid molecules which are fragments, allelic variants and/or derivatives of the nucleic acid molecules mentioned under a), b), c), d), e) or f),
h) nucleic acid molecules according to a), b), c), d), e), f) or g), which are linked to regulatory elements (promoters) which initiate the transcription in plant cells or
i) nucleic acid molecules, according to h), where the promoters are tissue-specific promoters, particularly preferably promoters which initiate transcription, specifically in plant endosperm cells.

Furthermore, the present invention relates to plasmids, vectors and plant cells or plants which contain a foreign nucleic acid molecule according to the invention.

In a further embodiment, the plant cells according to the invention and the plants according to the invention are characterized in that at least one foreign nucleic acid molecule encodes a protein having the activity of a starch synthase II. Preferably, the foreign nucleic acid molecules encoding a protein having the activity of a starch synthase II are the already mentioned nucleic acid molecules known to the person skilled in the art from the various plant species, particularly preferably nucleic acid molecules encoding a protein having the activity of a starch synthase II from wheat, in particular preferably a protein having the activity of a starch synthase II which has the amino acid sequence shown under SEQ ID NO 6 or which is encoded by the nucleic acid sequence shown in SEQ ID NO 5.

In a further embodiment, the plant cells according to the invention and the plants according to the invention are characterized in that a first foreign nucleic acid molecule encodes a protein having the activity of a glucan-water dikinase and a second foreign nucleic acid molecule encodes a protein having the activity of a starch synthase II.

The foreign nucleic acid molecules introduced for the genetic modification in the plant cells or plants can be an individual nucleic acid molecule or a number of nucleic acid molecules. They can therefore be both nucleic acid molecules which contain nucleic acid sequences coding for a protein having the activity of a glucan-water dikinase and nucleic acid sequences coding for a protein having the activity of a starch synthase II, and they can be nucleic acid molecules in which the nucleic acid sequences coding for a protein having the activity of a glucan-water dikinase and the nucleic acid sequences coding for a protein having the activity of a starch synthase II are present in different nucleic acid molecules. The nucleic acid sequences coding for a protein having the activity of a glucan-water dikinase and the nucleic acid sequences coding for a protein having the activity of a starch synthase II can be simultaneously contained, for example, in a vector, plasmid or nucleic acid molecules present in linear form, or else constituents of two vectors, plasmids or linear nucleic acid molecules in each case separate from one another.

If the nucleic acid sequences coding for a protein having the activity of a glucan-water dikinase and the nucleic acid sequences coding for a protein having the activity of a starch synthase II are present in two nucleic acid molecules which are separate from one another, they can either be introduced into the genome of the plant cell or plant at the same time ("cotransformation") or else in succession, i.e. following one another chronologically ("supertransformation"). The nucleic acid molecules separate from one another can also be introduced into different individual plant cells or plants of a species. Plant cells or plants can thereby be produced in which the activity of either at least one protein having the activity of a glucan-water dikinase or else at least one protein having the activity of a starch synthase II is increased. Plants according to the invention can then be produced by subsequent crossing of the plants, in which the activity of a protein having the activity of a glucan-water dikinase is increased, with those in which the activity of a protein having the activity of a starch synthase II is increased.

Furthermore, for the introduction of a foreign nucleic acid molecule instead of a wild-type plant cell or wild-type plant, a mutant cell or a mutant which is distinguished in that it already has an increased activity of a protein having the activity of a glucan-water dikinase or an increased activity of a protein having the activity of a starch synthase II is used. The mutants can be both spontaneously (naturally) occurring mutants, and those which have been produced by the selective use of mutagens (such as, for example, chemical agents, ionizing radiation) or genetic engineering processes (e.g. T-DNA activation tagging, transposon activation tagging, in situ activation, in vivo mutagenesis).

Plant cells according to the invention or plants according to the invention can therefore also be produced by introduction of a foreign nucleic acid molecule which leads to the increase in the activity of a protein having the activity of a glucan-water dikinase in a mutant cell or a mutant which already has an increased activity of a protein having the activity of a starch synthase II. Plant cells according to the invention or plants according to the invention can also be produced by introduction of a foreign nucleic acid molecule which leads to the increase in the activity of a protein having the activity of a starch synthase II into a mutant cell or a mutant which already has an increased activity of a protein having the activity of a glucan-water dikinase. Plant cells according to the invention or plants according to the invention can also be produced by crossing a mutant, in which the activity of a protein having the activity of a glucan-water dikinase is increased, with a plant which on account of the introduction of a foreign nucleic acid molecule has an increased activity of a protein having the activity of a starch synthase II. Likewise, it is possible to produce plant cells according to the invention or plants according to the invention by crossing a mutant, in which the activity of a protein having the activity of a starch synthase II is increased, with a plant which on account of the introduction of a foreign nucleic acid molecule has an increased activity of a protein having the activity of a glucan-water dikinase.

Plants according to the invention can also be produced by crossing a mutant, in which the activity of a protein having the activity of a starch synthase II is increased, with a mutant in which the activity of a protein having the activity of a glucan-water dikinase is increased.

A large number of techniques are available for the introduction of DNA into a plant host cell. These techniques include the transformation of plant cells with T-DNA using *Agrobacterium tumefaciens* or *Agrobacterium rhizogenes* as transformation agents, the fusion of protoplasts, injection, the electroporation of DNA, the introduction of the DNA by means of the biolistic approach, and further possibilities.

The use of agrobacteria-mediated transformation of plant cells has been intensively investigated and described, inter alia, in EP 120516; Hoekema, (In: The Binary Plant Vector System Offsetdruckkerij Kanters B. V. Alblasserdam (1985), Chapter V; Fraley et al., Crit. Rev. Plant Sci. 4, 1-46) and in An et al. (1985, EMBO J. 4, 277-287). For the transformation of potato, see, for example, Rocha-Sosa et al. (1989, EMBO J. 29-33).

The transformation of monocotyledonous plants by means of vectors based on *Agrobacterium transformation* has also been described (1993, Chan et al., Plant Mol. Biol. 22, 491-506; Hiei et al., 1994, Plant J. 6, 271-282; Deng et al., 1990, Science in China 33, 28-34; Wilmink et al., 1992, Plant Cell Reports 11, 76-80; May et al., 1995, Bio/Technology 13, 486-492; Conner and Domisse, 1992, Int. J. Plant Sci. 153, 550-555; Ritchie et al., 1993, Transgenic Res. 2, 252-265). Alternative methods for the transformation of monocotyledonous plants are transformation by means of the biolistic approach (Wan and Lemaux, 1994, Plant Physiol. 104, 37-48; Vasil et al., 1993, Bio/Technology 11, 1553-1558; Ritala et al., 1994, Plant Mol. Biol. 24, 317-325; Spencer et al., 1990, Theor. Appl. Genet. 79, 625-631), protoplast transformation, the electroporation of partially permeabilized cells or the incorporation of the DNA by means of glass fibers. The transformation of corn, in particular, is repeatedly described in the literature (cf., for example, WO95/06128, EP0513849, EP0465875, EP0292435; Fromm et al., 1990, Biotechnology 8, 833-844; Gordon-Kamm et al., 1990, Plant Cell 2, 603-618; Koziel et al., 1993, Biotechnology 11, 194-200; Moroc et al., 1990, Theor. Appl. Genet. 80, 721-726).

The successful transformation of other cereal species has also already been described, e.g. for barley (Wan and Lemaux, see above; Ritala et al., see above; Krens et al., 1982, Nature 296, 72-74) and for wheat (Nehra et al., 1994, Plant J. 5, 285-297; Becker et al., 1994, Plant Journal 5, 299-307). All above methods are suitable in the context of the present invention.

Plant cells and plants which are genetically modified by introduction of a protein having the activity of a glucan-water dikinase and/or of a protein having the activity of a starch synthase II can be distinguished from wild-type plant cells or wild-type plants, inter alia, by virtue of the fact that they have at least one foreign nucleic acid molecule which naturally does not occur in wild-type plant cells or wild-type plants or by virtue in the fact that a molecule of this type is present integrated at a site in the genome of the plant cell according to the invention or in the genome of the plant according to the invention, in which it does not occur in wild-type plant cells or wild-type plants, i.e. in another genomic environment. Furthermore, such plant cells according to the invention and plants according to the invention can be distinguished from wild-type plant cells or wild-type plants by virtue of the fact that they contain at least one copy of the foreign nucleic acid molecule stably integrated into their genome, optionally additionally to naturally occurring copies of a molecule of this type in the wild-type plant cells or wild-type plants. If the foreign nucleic acid molecule(s) introduced into the plant cells according to the invention or plants according to the invention is (are) additional copies to molecules already occurring naturally in the wild-type plant cells or wild-type plants, the plant cells according to the invention and the plants according to the invention can be distinguished from wild-type plant cells or wild-type plants in particular by virtue of the fact that this (these) additional copy (copies) is (are) located at sites in the genome at which they do not occur in wild-type plant cells or wild-type plants. This can be verified, for example, with the aid of a Southern blot analysis.

Furthermore, the plant cells according to the invention and the plants according to the invention can be distinguished from wild-type plant cells or wild-type plants preferably by at least one of the following features: if an introduced foreign nucleic acid molecule is heterologous with respect to the plant cell or plants, the plant cells according to the invention or plants according to the invention contain transcripts of the nucleic acid molecules introduced. These can be detected, for example, by means of Northern blot analysis or by RT-PCR (Reverse Transcription Polymerase Chain Reaction). Preferably, the plant cells according to the invention and the plants according to the invention contain a protein which is encoded by an introduced nucleic acid molecule. This can be detected, for example, by immunological methods, in particular by a Western blot analysis.

If an introduced foreign nucleic acid molecule is homologous with respect to the plant cell or plants, the plant cells according to the invention and the plants according to the invention can be distinguished from wild-type plant cells or wild-type plants, for example, on account of the additional expression of the introduced foreign nucleic acid molecules. The plant cells according to the invention and the plants according to the invention preferably contain transcripts of the foreign nucleic acid molecules. This can be detected, for example, by Northern blot analysis or with the aid of the "quantitative" RT-PCR.

The plants according to the invention can in principle be plants of any desired plant species, i.e. both monocotyledonous and dicotyledonous plants. Preferably, they are useful plants, i.e. plants which are cultivated by humans for purposes of nutrition or for technical, in particular industrial, purposes.

In a further embodiment, the plant according to the invention is a starch-storing plant.

The term "starch-storing plant" in connection with the present invention means all plants having plant parts which contain a storage starch, such as, for example, corn, rice, wheat, rye, oats, barley, manioc, potato, sago, taro, mung bean, peas, *sorghum*, sweet potato.

In a preferred embodiment, the present invention relates to starch-storing monocotyledonous plants according to the invention, in particular preferably plants of the (systematic) family Poaceae. Particularly preferably, these are rice, corn or wheat plants.

The term "wheat plant" in connection with the present invention means plant species of the genus *Triticum* or plants which are produced from crossings with plants of the genus *Triticum*, particularly plant species of the genus *Triticum* cultivated for commercial purposes in agriculture, or plants which are produced from crossings with plants of the genus *Triticum; Triticum aestivum* is preferred in particular.

The term "corn plant" in connection with the present invention means plant species of the genus *Zea*, particularly plant species of the genus *Zea* cultivated for commercial purposes in agriculture, particularly preferably *Zea mais*.

The term "rice plants" in connection with the present invention means plant species of the genus *Oryza*, particularly plant species of the genus *Oryza* cultivated for commercial purposes in agriculture, particularly preferably *Oryza sativa*.

In a further embodiment, the plant cells according to the invention and the plants according to the invention are transgenic plant cells or transgenic plants.

Plant cells according to the invention and plants according to the invention synthesize a modified starch in comparison to starch isolated from wild-type plant cells or wild-type plants which are not genetically modified.

A further subject of the present invention therefore relates to plant cells according to the invention or plants according to the invention which synthesize a modified starch in comparison to starch isolated from the corresponding wild-type plant cells which are not genetically modified or isolated from corresponding wild-type plants which are not genetically modified.

The invention further relates to genetically modified plants which contain plant cells according to the invention. Such plants can be produced from plant cells according to the invention by regeneration.

The present invention also relates to propagative material of plants according to the invention, comprising a plant cell according to the invention.

The term "propagative material" here comprises any constituents of the plants which are suitable for the production of descendants in a vegetative or sexual manner. For vegetative propagation, for example, cuttings, callus cultures, rhizomes or tubers are suitable. Other propagative material comprises, for example, fruit, seeds, seedlings, protoplasts, cell cultures, etc. Particularly preferably, the propagative material is endosperm-containing seeds (grains).

In a further embodiment, the present invention relates to harvestable plant parts of plants according to the invention, such as fruit, storage roots, roots, flowers, buds, shoots or stems, preferably seeds, granules or tubers, these harvestable parts containing plant cells according to the invention.

Starch which is synthesized from plant cells according to the invention or from plants according to the invention is distinguished, in comparison to starch isolated from corresponding wild-type plant cells which are not genetically modified or in comparison to starch isolated from corresponding wild-type plants which are not genetically modified, in particular in that it has an increased hot water swelling power.

Furthermore, the present invention also relates to a process for the production of a genetically modified plant, wherein a) a plant cell is genetically modified, the genetic modification comprising the following steps i and ii in any desired sequence, individually or simultaneously
  i) introduction of a genetic modification into the plant cell, the genetic modification leading to the increase in the activity of a protein having the activity of a starch synthase II, in comparison to corresponding wild-type plant cells which are not genetically modified,
  ii) introduction of a genetic modification into the plant cell, the genetic modification leading to the increase in the activity of a protein having the activity of a glucan-water dikinase, in comparison to corresponding wild-type plant cells which are not genetically modified
b) a plant is regenerated from plant cells of step a);
c) optionally further plants are produced with the aid of the plants according to step b)

where plant cells are optionally isolated from plants according to step b) or c) and process steps a) to c) are repeated until a plant has been produced which contains a foreign nucleic acid molecule encoding a protein having the activity of a starch synthase II and a foreign nucleic acid molecule encoding a protein having the activity of a glucan-water dikinase.

In a preferred embodiment, the process according to the invention for the preparation of a genetically modified plant comprises the following steps:

a) a plant cell is genetically modified, the genetic modification comprising the following steps i and ii in any desired sequence or any desired combinations of the following steps i and ii being carried out individually or simultaneously
  i) introduction of a genetic modification into the plant cell, the genetic modification leading to the increase in the activity of a protein having the activity of a starch synthase II, in comparison to corresponding wild-type plant cells which are not genetically modified
  ii) introduction of a genetic modification into the plant cell, the genetic modification leading to the increase in the activity of a protein having the activity of a glucan-water dikinase, in comparison to corresponding wild-type plant cells which are not genetically modified
b) a plant is regenerated from plant cells comprising the genetic modification according to the steps
  i) a) i
  ii) a) ii
  iii) a) i and a) ii,
c) in plant cells of plants according to step
  i) b) i a genetic modification according to step a) ii,
  ii) b) ii a genetic modification according to step a) i,
  is introduced and a plant is regenerated
d) optionally further plants are produced with the aid of the plants obtained according to one of steps b) iii or c) i or c) ii.

It applies for the genetic modifications introduced into the plant cell according to step a) that they are in principle any type of modification which leads to the increase in the activity of a protein having the enzymatic activity of a starch synthase II and/or which leads to the increase in the activity of a protein having the enzymatic activity of a glucan-water dikinase.

The regeneration of the plants according to step B) and optionally step c) of the process according to the invention can be carried out according to the methods known to the person skilled in the art (described, for example, in "Plant Cell Culture Protocols", 1999, edt. by R. D. Hall, Humana Press, ISBN 0-89603-549-2).

The production of further plants (depending on processes according to step c) or step d)) of the process according to the invention can be carried out, for example, by vegetative propagation (for example by means of seedlings, tubers or by means of callus culture and regeneration of whole plants) or by sexual propagation. Sexual propagation preferably takes place here in a controlled manner, i.e. selected plants having certain properties are crossed with one another and propagated. The choice preferably takes place here in such a way that the further plants (which are produced according to processes according to step c) or step d) comprise the modifications introduced in the preceding steps.

In processes according to the invention for the production of genetically modified plants, the genetic modifications for the production of the genetically modified plant cells according to the invention can be carried out simultaneously or in steps following one another. It is unimportant here whether, for successive genetic modifications which lead to an increased activity of a protein having the enzymatic activity of a starch synthase II, the same method is used as for the genetic modification which leads to an increased activity of a protein having the enzymatic activity of a glucan-water dikinase.

In a preferred embodiment of the process according to the invention for the production of a genetically modified plant, a process step b)-1 follows step b) in which plants are selected which have an increased activity of a protein having the activity of a starch synthase II according to step a) i and/or which have an increased activity of a protein having the activity of a glucan water dikinase according to step a) ii. The selected plants are then used for the further process steps.

Preferably, plants are selected here which contain the genetic modification according to step a) i and have an increase in the activity of a protein having the activity of a starch synthase II, which is increased at least 6-fold, preferably at least 7-fold, particularly preferably at least 8-fold, in particular preferably at least 9-fold and very particularly preferably at least 10-fold, in comparison to corresponding genetically unmodified wild-type plants.

Preferably, plants are selected here which contain the genetic modification according to step a) ii and which synthesize a starch which has a starch phosphate content which is increased at least 4-fold, particularly preferably at least 5-fold, in particular preferably at least 6-fold, in comparison to corresponding genetically unmodified wild-type plants.

In a further embodiment of the process according to the invention for the production of a genetically modified plant, the genetic modification consists in the introduction of at least one foreign nucleic acid molecule into the genome of the plant cell, the presence or the expression of the foreign nucleic acid molecule/nucleic acid molecules leading to an increased activity of a protein having the enzymatic activity of a starch synthase II and/or to an increased activity of a protein having the enzymatic activity of a glucan-water dikinase in the cell.

In a further embodiment of the process according to the invention for the production of a genetically modified plant, the genetic modification consists in the introduction of at least one foreign nucleic acid molecule into the genome of the plant cell, the foreign nucleic acid molecule/nucleic acid molecules comprising a sequence encoding a protein having the enzymatic activity of a starch synthase II and/or a protein having the enzymatic activity of a glucan-water dikinase.

In a further embodiment of the process according to the invention for the production of a genetically modified plant according to the invention, at least one foreign nucleic acid molecule encodes a protein having the enzymatic activity of a glucan-water dikinase from potato, wheat, rice, corn, soybean, citrus, *Curcuma* or *Arabidopsis*.

Preferably, at least one foreign nucleic acid molecule encodes a protein having the enzymatic activity of a glucan-water dikinase from *Curcuma longa* or potato, particularly preferably from potato and in particular preferably a protein which has the amino acid sequence shown under SEQ ID NO 6 or is encoded by the nucleic acid sequence shown under SEQ ID NO 5. References for proteins encoding nucleic acid sequences and having the enzymatic activity of a glucan-water dikinase from the plants mentioned are already indicated further above.

In a further embodiment of the process according to the invention for the production of a genetically modified plant according to the invention, at least one foreign nucleic acid molecule encodes a protein having the enzymatic activity of a starch synthase II from barley, *Aegilops*, rice, corn, manioc, bean, potato, pea, sweet potato, *Arabidopsis*, taro, *Ostreococcus* or *Chlamydomonas*. Preferably, at least one foreign nucleic acid molecule encodes a protein having the enzymatic activity of a starch synthase II from wheat. References for the proteins encoding the nucleic acid sequences mentioned having the enzymatic activity of a starch synthase II from the plants mentioned are already indicated further above.

As already described above for foreign nucleic acid molecules incorporated into a plant cell or plant for genetic modification, step a) of the process according to the invention for the production of a genetically modified plant can involve an individual nucleic acid molecule or a number of nucleic acid molecules. The foreign nucleic acid molecules encoding a protein having the enzymatic activity of a starch synthase II or encoding a protein having the enzymatic activity of a glucan-water dikinase can thus be present together on a single nucleic acid molecule or they can be present on separate nucleic acid molecules. If the nucleic acid molecules encoding a protein having the enzymatic activity of a starch synthase II and encoding a protein having the activity of a glucan-water dikinase are present on separate nucleic acid molecules, these nucleic acid molecules can be introduced into a plant cell simultaneously or in successive steps.

Furthermore, for the introduction of a foreign nucleic acid molecule during the implementation of processes according to the invention, Instead of a wild-type plant cell or wild-type plant, a mutant cell or a mutant which is distinguished in that it already has an increased activity of a protein having the enzymatic activity of a starch synthase II or an increased activity of a protein having the enzymatic activity of a glucan-water dikinase can be used. The statements made further above on the use of mutants for the production of plant cells or plants according to the invention are to be used correspondingly here.

In a preferred embodiment, the present invention relates to processes according to the invention for the production of a genetically modified plant, in which the nucleic acid molecule encoding a protein having the enzymatic activity of a starch synthase II is selected from the group consisting of
a) nucleic acid molecules which encode a protein having the amino acid sequence under SEQ ID NO 6;
b) nucleic acid molecules which encode a protein having the activity of a starch synthase II, the amino acid sequence of which has at least 70%, preferentially at least 80%, preferably at least 90%, particularly preferably at least 95% and most preferably of at least 98% to the amino acid sequence shown under SEQ ID NO 6;
c) nucleic acid molecules which comprise the nucleic acid sequence shown under SEQ ID NO 5 or a complementary sequence;
d) nucleic acid molecules which have an identity of at least 70%, preferentially of at least 80%, preferably of at least 90%, in particular preferably of at least 95% and most preferably of at least 98% to the nucleic acid sequences described under c),
e) nucleic acid molecules which hybridize under stringent conditions with at least one strand of the nucleic acid molecules described under a) or c);
f) nucleic acid molecules whose nucleotide sequence differs from the sequence of the nucleic acid molecules mentioned under a) or c) on account of the degeneracy of the genetic code;
g) nucleic acid molecules which are fragments, allelic variants and/or derivatives of the nucleic acid molecules mentioned under a), b), c), d), e) or f),
h) nucleic acid molecules encoding a protein having the activity of a starch synthase II, where the nucleic acid sequences encoding a protein having the activity of a starch synthase II are linked to regulatory elements (promoters) which initiate transcription in plant cells or
i) nucleic acid molecules, according to h), where the promoters are tissue-specific promoters, particularly preferably promoters which initiate transcription, specifically in plant endosperm cells.

In a further preferred embodiment, the present invention relates to processes according to the invention for the production of a genetically modified plant, in which the nucleic acid molecule encoding a protein having the enzymatic activity of a glucan-water dikinase is selected from the group consisting of
a) nucleic acid molecules which encode a protein having the amino acid sequence shown under SEQ ID NO 2 or SEQ ID NO 4;
b) nucleic acid molecules which encode a protein which has the activity of a glucan-water dikinase and whose sequence has an identity of at least 70%, preferentially of at least 80%, preferably of at least 90%, in particular preferably of at least 95% and most preferably of at least 98% to the amino acid sequence shown under SEQ ID NO 2 or SEQ ID NO 4;
c) nucleic acid molecules which comprise the nucleic acid sequence shown under SEQ ID NO 1 or SEQ ID NO 3 or a complementary sequence;
d) nucleic acid molecules which have an identity of at least 70%, preferentially of at least 80%, preferably of at least 90%, in particular preferably of at least 95% and most preferably of at least 98% to the nucleic acid sequences described under c),
e) nucleic acid molecules which hybridize under stringent conditions with at least one strand of the nucleic acid molecules described under a) or c);
f) nucleic acid molecules whose nucleotide sequence differs from the sequence of the nucleic acid molecules mentioned under a) or c) on account of the degeneracy of the genetic code;
g) nucleic acid molecules which are fragments, allelic variants and/or derivatives of the nucleic acid molecules mentioned under a), b), c), d), e) or f),
h) nucleic acid molecules encoding a protein having the activity of a glucan-water dikinase, where the nucleic acid sequences encoding a protein having the activity of a glucan-water dikinase are linked to regulatory elements (promoters) which initiate transcription in plant cells or
i) nucleic acid molecules, according to h), where the promoters are tissue-specific promoters, particularly preferably promoters which initiate transcription, specifically in plant endosperm cells.

The term "identity" should be understood in connection with the present invention as meaning the number of identical amino acids/nucleotides (identity) with other proteins/nucleic acids, expressed in percent. Preferably, the identity concerning a protein having the activity of a starch synthase II is determined by comparisons of the amino acid sequence indicated under SEQ ID NO 6 and the identity concerning a nucleic acid molecule encoding a protein having the activity of a starch synthase II is determined by comparisons of the nucleic acid sequence indicated under SEQ ID NO 5 and the identity concerning a protein having the activity of a glucan-water dikinase is determined by comparisons of the amino acid sequence indicated under SEQ ID NO 2 or SEQ ID NO 4 or the identity concerning a nucleic acid molecule encoding a protein having the activity of a glucan-water dikinase is determined by comparisons of the nucleic acid sequence indicated under SEQ ID NO 1 or SEQ ID NO 3 to other proteins/nucleic acids with the aid of computer programs. If sequences which are being compared to one another have different lengths, the identity is to be determined such that the number of amino acids/nucleotides which the shorter sequence has in common with the longer sequence determines the percentage proportion of the identity. Preferably, the identity is determined by means of the computer program ClustalW which is known and available to the public (Thompson et al., Nucleic Acids Research 22 (1994), 4673-4680). ClustalW is made publicly available by Julie Thompson and Toby Gibson, European Molecular Biology Laboratory, Meyerhofstrasse 1, D 69117 Heidelberg, Germany. ClustalW can likewise be downloaded from various Internet sites, inter alia at the IGBMC (Institut de Genetique et de Biologie Moleculaire et Cellulaire, B. P. 163, 67404 Ilikirch Cedex, France; available on the world wide web at ftp-igbmc.u-strasbg.fr/pub/) and at the EBI (available on the world wide web at ftp.ebi.ac.uk/pub/software/) and at all mirrored Internet sites of the EBI (European Bioinformatics Institute, Wellcome Trust Genome Campus, Hinxton, Cambridge CB 10 1SD, UK).

Preferably, the ClustalW computer program of version 1.8 is used in order to determine the identity between proteins described in the context of the present invention and other proteins. The following parameters are to be set here: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

Preferably, the ClustalW computer program of version 1.8 is used in order to determine the identity between, for example, the nucleotide sequence of the nucleic acid molecules described in the context of the present invention and the nucleotide sequence of other nucleic acid molecules. The following parameters are to be set here: KTUPLE=2, TOPDIAGS=4, PAIRGAP=5, DNAMATRIX:IUB, GAPOPEN=10, GAPEXT=5, MAXDIV=40, TRANSITIONS: unweighted.

Identity further means that functional and/or structural equivalence exists between the nucleic acid molecules in question or the proteins encoded by them. The nucleic acid molecules which are homologous to the molecules described above and are derivatives of these molecules are usually variations of these molecules which are modifications which exert the same biological function. They can be either naturally occurring variations here, for example sequences of other species, or mutations, where these mutations can have occurred naturally or have been introduced by selective mutagenesis. Further, the variations can be synthetically prepared sequences. In the case of the allelic variants, they can be both naturally occurring variants and variants which are prepared synthetically or produced by recombinant DNA techniques. A special form of derivatives are, for example, nucleic acid molecules which on account of the degeneracy of the genetic code differ from nucleic acid molecules described in the context of the present invention.

The term "hybridization" in the context of the present invention means hybridization under conventional hybridization conditions, preferentially under stringent conditions, as described, for example, in Sambrook et al., Molecular Cloning, A Laboratory Manual, 3rd edition (2001) Cold Spring Harbor Laboratory Press, Cold Spring Harbor, N.Y. ISBN: 0879695773). Particularly preferably, "to hybridize" means hybridization under the following conditions:
hybridization Buffer:
2×SSC; 10×Denhardt solution (Ficoll 400+PEG+BSA; ratio 1:1:1); 0.1% SDS; 5 mM EDTA; 50 mM $Na_2HPO4$; 250 µg/ml of herring sperm DNA; 50 µg/ml of tRNA; or 25 M sodium phosphate buffer pH 7.2; 1 mM EDTA; 7% SDS
hybridization temperature:
T=65 to 68° C.
wash buffer: 0.1×SSC; 0.1% SDS
wash temperature: T=65 to 68° C.

Nucleic acid molecules which hybridize with the molecules mentioned can be isolated, for example, from genomic or from cDNA libraries. The identification and isolation of such nucleic acid molecules can be carried out here using the nucleic acid molecules mentioned or parts of these molecules or the reverse complements of these molecules, e.g. by means of hybridization according to standard processes or by amplification by means of PCR.

As a hybridization probe for the isolation of a nucleic acid sequence encoding a protein having the activity of a starch synthase II or having the activity of a glucan-water dikinase, it is possible to use, for example, nucleic acid molecules which exactly contain the or essentially contain the nucleotide sequence indicated under SEQ ID NO 5 (starch synthase II) or under SEQ ID NO 1 or SEQ ID NO 3 (glucan-water dikinase) or parts of these sequences. The fragments used as a hybridization probe can be synthetic fragments or oligonucleotides which were produced with the aid of the customary synthesis techniques and whose sequence essentially agrees with that of a nucleic acid molecule described in the context of the present invention. If genes which hybridize with the nucleic acid sequences described in the context of the present invention have been identified and isolated, a determination of the sequence and an analysis of the properties of the proteins encoded by this sequence should be carried out in order to determine whether they are proteins which have the activity of a starch synthase II or the activity of a glucan-water dikinase.

The molecules hybridizing with the nucleic acid molecules described in the context of the present invention in particular include fragments, derivatives and allelic variants of the nucleic acid molecules mentioned. The term "derivative" in connection with the present invention means that the sequences of these molecules differ from the sequences of the nucleic acid molecules described above in one or more positions and have a high degree of identity to these sequences. The differences to the nucleic acid molecules described above can result here, for example, by deletion, addition, substitution, insertion or recombination.

For the expression of nucleic acid molecules according to the invention which encode a protein having the activity of a starch synthase II and/or a protein having the activity of a glucan-water dikinase, these are preferably linked to regulatory DNA sequences which guarantee transcription in plant cells. These in particular include promoters. Generally, any promoters active in plant cells are suitable for expression.

The promoter can be chosen here such that the expression takes place constitutively or only in a certain tissue, at a certain time in the plant development or at a time determined by external influences. Both with respect to the plant and with respect to the nucleic acid molecule, the promoter can be homologous or heterologous.

Suitable promoters are, for example, the promoter of the 35S RNA of the cauliflower mosaic virus and the ubiquitin promoter from corn, the promoter of the actin-1 gene from rice (McElroy et al., 1990, Plant Cell 2(2), 163-171), the histone promoter from maize (WO 99 34005) for constitutive expression, the Patatingen promoter B33 (Rocha-Sosa et al., EMBO J. 8 (1989), 23-29) for tuber-specific expression in potatoes or a promoter which ensures expression only in photosynthetically active tissues, e.g. the ST-LS1 promoter (Stockhaus et al., Proc. Natl. Acad. Sci. USA 84 (1987), 7943-7947; Stockhaus et al., EMBO J. 8 (1989) 2445-2451) or for an endosperm-specific expression the HMG promoter from wheat, the USP promoter, the phaseolin promoter, promoters of zein genes from corn (Pedersen et al., Cell 29 (1982), 1015-1026; Quatroccio et al., Plant Mol. Biol. 15 (1990), 81-93), a glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218), a globulin promoter (Nakase et al., 1996, Gene 170(2), 223-226), a prolamine promoter (Qu and Takaiwa, 2004, Plant Biotechnology Journal 2(2), 113-125) or a Shrunken-1 promoter (Werr et al., EMBO J. 4 (1985), 1373-1380). However, promoters can also be used which are only activated at a time determined by external influences (see, for example, WO 9307279). Also of interest can be promoters of heat-shock proteins which allow simple induction. Furthermore, seed-specific promoters can be used, such as, for example, the USP promoter from *Vicia faba*, which guarantees seed-specific expression in *Vicia faba* and other plants (Fiedler et al., Plant Mol. Biol. 22 (1993), 669-679; Bäumlein et al., Mol. Gen. Genet. 225 (1991), 459-467).

Furthermore, a termination sequence (polyadenylation signal) can be present which serves for the addition of a poly-A tail to the transcript. The poly-A tail is attributed a function in the stabilization of the transcripts. Such elements are described in the literature (cf. Gielen et al., EMBO J. 8 (1989), 23-29) and are arbitrarily replaceable.

Intron sequences between the promoter and the encoding region can also be present. Intron sequences of this type can lead to stability of expression and to increased expression in plants (Callis et al., 1987 Genes Devel. 1, 1183-1200; Luehrsen and Walbot, 1991, Mol. Gen. Genet. 225, 81-93; Rethmeier et al., 1997; Plant Journal. 12(4): 895-899; Rose and Beliakoff, 2000, Plant Physiol. 122 (2), 535-542; Vasil et al., 1989, Plant Physiol. 91, 1575-1579; Xu et al., 2003, Science in China Series C Vol. 46 No. 6, 561-569). Suitable intron sequences are, for example, the first intron of the sh1 gene from corn, the first intron of the poly-ubiquitin gene 1 from corn, the first intron of the EPSPS gene from rice, the first intron of the actin-1 gene from rice (McElroy et al., 1990, Plant Cell 2(2), 163-171) or one of the two first introns of the PAT1 gene from *Arabidopsis*.

A further embodiment of the present invention relates to a process for the production of a genetically modified plant according to the invention, wherein
a) a plant cell is genetically modified, the genetic modification leading to the increase in the activity of a protein having the activity of a starch synthase II in comparison to corresponding wild-type plant cells which are not genetically modified;
b) a plant is regenerated from plant cells of step a);
c) optionally further plants are produced with the aid of the plants according to step b) and
d) plants obtained according to step b) or c) are crossed with a plant which has an increase in the activity of a protein having the activity of a glucan-water dikinase, in comparison to corresponding wild-type plant cells which are not genetically modified.

A further embodiment of the present invention relates to a process for the production of a genetically modified plant according to the invention, in wherein
a) a plant cell is genetically modified, the genetic modification leading to the increase in the enzymatic activity of a protein having the activity of a glucan-water dikinase in comparison to corresponding wild-type plant cells which are not genetically modified;
b) a plant is regenerated from plant cells of step a);
c) optionally further plants are produced with the aid of the plant according to step b) and
d) plants obtained according to step b) or c) are crossed with a plant which has an increase in the enzymatic activity of a protein having the activity of a starch synthase II, in comparison to corresponding wild-type plant cells which are not genetically modified.

In the two last-mentioned processes for the production of a genetically modified plant, the plants according to step a) can be genetically modified as already described above. The regeneration of plants according to step b) and the production of further plants according to step c) were likewise already shown further above.

A plant which is crossed according to step d) of the two last-mentioned embodiments with plants or descendants of the plants obtained from step b) or c) can be any plant which has an increased activity of a protein having the activity of a starch synthase II or an increased activity of a protein having the activity of a glucan-water dikinase, in comparison to corresponding wild-type plants. The increase in the activity of a protein having the activity of a starch synthase II or of a protein having the activity of a glucan-water dikinase can be produced here by any modification which leads to an increase in the activity of the proteins in question in the corresponding plants. These plants can be mutants or plants modified by means of genetic engineering methods. The mutants can be both spontaneously (naturally) occurring mutants, and also those which have been produced by the selective use of mutagens (such as, for example, chemical agents, ionizing radiation) or genetic engineering processes (e.g. transposon activation tagging, T-DNA activation tagging, in vivo mutagenesis).

Preferably, the plants produced by genetic engineering processes are mutants produced by means of insertion mutagenesis, particularly preferably genetically modified plants which express a foreign nucleic acid molecule, in particular preferably genetically modified plants in which the foreign nucleic acid molecule encodes a protein having the activity of a starch synthase II or a protein having the activity of a glucan-water dikinase.

Preferably, for the crossing in the two last-mentioned processes according to the invention, plants are used which have an activity of a protein having the activity of a starch synthase II, which is increased by at least 6-fold, preferably by at least 7-fold, particularly preferably by at least 8-fold, in particular preferably by at least 9-fold and very particularly preferably by at least 10-fold, in comparison to corresponding genetically unmodified wild-type plants.

Concerning plants which have an increased activity of a protein having the activity of a glucan-water dikinase, for the crossing in the two last-mentioned processes according to the invention plants are preferably used which synthesize a starch which has a starch phosphate content which is increased at least 4-fold, particularly preferably at least 5-fold, in particular preferably at least 6-fold, in comparison to corresponding genetically unmodified wild-type plants.

In a preferred embodiment, processes according to the invention for the production of a genetically modified plant are used for the production of plants according to the invention or of plants which have properties of plants according to the invention.

The present invention also relates to the plants obtainable by processes according to the invention.

It has surprisingly been found that plant cells according to the invention and plants according to the invention which have an increased activity of a protein having the activity of a starch synthase II and an increased activity of a protein having the activity of a glucan-water dikinase synthesize a modified starch. In particular, the fact that starch synthesized by plant cells according to the invention or plants according to the invention has an increased hot water swelling power was surprising. The increased hot water swelling power of starches isolable from plant cells according to the invention and plants according to the invention imparts properties to the starches which make them better suited for certain applications than conventional starches. If starch is employed, for example, as a thickening agent, the increased hot water swelling power of the starch leads to distinctly less starch having to be employed in order to achieve an identical thickening power. This has the result that, for example, the calorie content of foods thickened with starch is reduced.

A further subject of the present invention relates to modified starch which has an increased hot water swelling power. Particularly preferably, the hot water swelling power of modified starch according to the invention is increased by at least the factor 2, in particular by at least the factor 3 and very particularly preferably by at least the factor 4, in comparison to starch isolated from corresponding wild-type plant cells which are not genetically modified or isolated from corresponding wild-type plants which are not genetically modified.

Methods for the determination of the hot water swelling power are known to the person skilled in the art and described in the literature (e.g. Leach et al., 1959, Cereal Chemistry 36, 534-544). A method to be used preferably in connection with the present invention for the determination of the hot water swelling power is described under General Methods, item 1.

Preferably, the present invention relates to modified starch which has a hot water swelling power of at least 110 g/g, preferably of at least 115 g/g, particularly preferably of at least 120 g/g and in particular preferably of at least 125 g/g. Preferably, the modified starch has a hot water swelling power of at most 350 g/g, particularly preferably of at most 300 g/g, in particular preferably of at most 250 g/g and especially preferably of at most 200 g/g.

A further subject of the present invention relates to modified starch isolated from a monocotyledonous plant cell or from a monocotyledonous plant, which has a hot water swelling power of at least 60 g/g, preferably of at least 75 g/g, particularly preferably of at least 90 g/g, in particular preferably of at least 105 g/g and especially preferably of at least 120 g/g. Preferably, the modified starch isolated from a monocotyledonous plant cell or monocotyledonous plant has a hot water swelling power of at most 250 g/g, particularly preferably of at most 200 g/g, in particular preferably of at most 175 g/g and especially preferably of at most 150 g/g.

A further subject of the present invention relates to modified starch isolated from rice plant cells or rice plants, which has a hot water swelling power of at least 65 g g/g, preferably of at least 80 g/g, particularly preferably of at least 100 g/g, in particular preferably of at least 115 g/g and especially preferably of at least 125 g/g. Preferably, the modified starch isolated from a rice plant cell or rice plant has a hot water swelling power of at most 250 g/g, particularly preferably of at most 200 g/g, in particular preferably of at most 175 g/g and especially preferably of at most 150 g/g.

A further preferred subject of the present invention relates to modified starch isolated from corn plant cells or corn plants, which has a hot water swelling power of at least 40 g/g, preferably of at least 42 g/g, more preferably of at least 45 g/g and most preferably of at least 55 g/g.

A further preferred subject of the present invention relates to modified starch isolated from wheat plant cells or wheat plants, which has a hot water swelling power of at least 35 g/g, preferably of at least 50 g/g.

Starch synthesized from genetically modified plant cells according to the invention or genetically modified plants according to the invention preferably has an increased starch phosphate content. The starch phosphate content of starch isolated from plant cells according to the invention or plants according to the invention is distinctly higher here than the starch phosphate content which would be expected after crossing from the sum of the phosphate content of the parent plants in question.

A preferred subject of the present invention therefore relates to modified starch according to the invention which has an increased starch phosphate content, in comparison to starch isolated from corresponding wild-type plant cells which are not genetically modified or corresponding wild-type plants which are not genetically modified. Preferably, the starch phosphate content of starch according to the invention is increased at least 10-fold, particularly preferably at least 15-fold, in particular preferably at least 20-fold and very particularly preferably at least 25-fold, in comparison to starch isolated from corresponding wild-type plant cells which are not genetically modified, or isolated from corresponding wild-type plants which are not genetically modified.

Preferably, modified starch according to the invention has at least 10-fold more, particularly preferably at least 15-fold more, in particular preferably at least 20-fold more and very particularly preferably at least 25-fold more starch phosphate in the C6 position of the glucose molecules of the starch than starch isolated from corresponding wild-type plant cells or isolated from corresponding wild-type plants.

The amount of the starch phosphate bonded in the C6 position of the glucose molecules can be determined using the methods known to the person skilled in the art, such as, for example, photometrically by means of a coupled enzymatic test or by means of $^{31}$P-NMR according to the method described in Kasemusuwan and Jane (1996, Cereal Chemistry 73, 702-707). Preferably, in connection with the present invention the amount of starch phosphate bonded in the C6 position of the glucose molecules is determined using the method described under General Methods, item 2.

A further preferred subject of the present invention relates to starch modified according to the invention, which has been isolated from a monocotyledonous plant cell or from a monocotyledonous plant and has a starch phosphate content bonded in the C6 position of the glucose molecules of the starch of at least 11 nmol per mg of starch, particularly preferably of at least 12 nmol per mg of starch. In particular, this modified starch according to the invention is preferably corn, rice or wheat starch.

In a further embodiment of the present invention, the modified starches according to the invention are native starches.

The term "native starch" in connection with the present invention means that the starch is isolated from plants according to the invention, harvestable plant parts according to the invention, starch-storing parts according to the invention or propagation material of plants according to the invention according to methods known to the person skilled in the art.

The present invention also relates to modified starch according to the invention, obtainable from plant cells according to the invention or plants according to the invention, from propagation material according to the invention or from harvestable plant parts according to the invention, or obtainable from plants which have been produced using a process according to the invention for the production of a genetically modified plant.

The present invention also relates to plant cells or plants which synthesize a modified starch according to the invention.

The present invention further relates to a process for the production of a modified starch, comprising the step of extraction of the starch from a plant cell according to the invention or a plant according to the invention, from propagation material according to the invention of a plant of this type and/or from harvestable plant parts of such a plant according to the invention, preferably from starch-storing parts of such a plant according to the invention. Preferably, a process of this type also comprises the step of the harvesting of the cultivated plants or plant parts and/or of the propagation material of these plants before the extraction of the starch and particularly preferably, furthermore the step of the cultivation of plants according to the invention before harvesting.

Processes for the extraction of the starch from plants or from the starch-storing parts of plants are known to the person skilled in the art. Furthermore, processes for the extraction of the starch from various starch-storing plants are described, for example, in Starch: Chemistry and Technology (ed.: Whistler, BeMiller and Paschall (1994), 2nd edition, Academic Press Inc. London Ltd; ISBN 0-12-746270-8; see, for example, chapter XII, page 412-468: Corn and Sorghum Starches: Production; by Watson; chapter XIII, page 469-479: Tapioca, Arrowroot and Sago Starches: Production; by Corbishley and Miller; chapter XIV, page 479-490; Potato Starch: Production and Uses; by Mitch; chapter XV, page 491 to 506; Wheat Starch: Production, Modification and Uses; by Knight and Oson; and chapter XVI, page 507 to 528: Rice Starch: Production and Uses; by Rohmer and Klem; Corn Starch: Eckhoff et al., Cereal Chem. 73 (1996), 54-57, the extraction of corn starch on the industrial scale is usually achieved by "wet milling".). Devices which are commonly used in processes for the extraction of starch from plant material are separators, decanters, hydrocyclones, spray dryers and fluidized bed dryers.

The term "starch-storing parts" should be understood in connection with the present invention as meaning those parts of a plant in which starch, unlike transitory leaf starch, is stored as a depot for the perennation of longer time periods. Preferred starch-storing plant parts are, for example, tubers, storage roots and grains, grains comprising an endosperm are particularly preferred, grains comprising an endosperm from corn, rice or wheat plants are in particular preferred.

In a preferred embodiment, processes according to the invention for the production of a modified starch are used for the production of a starch according to the invention.

The present invention likewise relates to modified starch, obtainable by a process according to the invention for the production of modified starch.

The present invention furthermore relates to the use of plant cells according to the invention or plants according to the invention for the production of a modified starch.

It is known to the person skilled in the art that the properties of starch can be altered, for example, by thermal, chemical, enzymatic or mechanical derivatization. Derivatized starches are particularly suitable for various applications in the food and/or non-food area. The starches according to the invention are better suited as a starting substance for the production of derivatized starches than conventional starches, since they have a higher content of reactive functional groups, for example, due to the higher content of starch phosphate. Furthermore, the derivatizations can be carried out at higher temperatures on account of the increased hot water swelling power of starches according to the invention, without significantly destroying the starch granule structure in the course of this.

The present invention therefore also relates to processes for the production of a derivatized starch, in which modified starch according to the invention is subsequently derivatized.

The term "derivatized starch" should be understood in connection with the present invention as meaning a modified starch according to the invention, whose properties after isolation from plant cells have been altered with the aid of chemical, enzymatic, thermal or mechanical processes.

In a further embodiment of the present invention, the derivatized starch according to the invention is starch treated with heat and/or with acid.

In a further embodiment, the derivatized starches are starch ethers, in particular starch alkyl ethers, O-allyl ethers, hydroxyalkyl ethers, O-carboxylmethyl ethers, nitrogen-containing starch ethers, phosphate-containing starch ethers or sulfur-containing starch ethers.

In a further embodiment, the derivatized starches are crosslinked starches.

In a further embodiment, the derivatized starches are starch graft polymers.

In a further embodiment, the derivatized starches are oxidized starches.

In a further embodiment, the derivatized starches are starch esters, in particular starch esters which have been introduced into the starch using organic acids. The derivatized starches are particularly preferably "phosphate", "nitrate", "sulfate", "xanthate", "acetate" or "citrate" starches.

The derivatized starches according to the invention are suitable for various uses in the pharmaceutical industry, and in the food and/or non-food field. Methods for the production of derivatized starches according to the invention are known to the person skilled in the art and adequately described in the general literature. A summary of the production of derivatized starches is found, for example, in Orthoefer (in Corn, Chemistry and Technology, 1987, eds. Watson and Ramstad, chapter 16, 479-499).

The present invention likewise relates to derivatized starch obtainable by the process according to the invention for the production of a derivatized starch.

The present invention further relates to the use of modified starches according to the invention for the production of derivatized starch.

Starch-storing parts of plants are often processed to give flours. Examples of parts of plants from which flours can be produced are, for example, tubers from potato plants and grains from grain plants. For the production of flours from cereal plants, the endosperm-containing grains of these plants are ground and sieved. Starch is a main constituent of the endosperm. In other plants which contain no endosperm, but other starch-storing parts, such as, for example, tubers or roots, flour is often produced by comminuting, drying and subsequent grinding of the storage organs in question. The starch of the endosperm or contained in starch-storing parts of plants is an essential part of the flour which is produced from the plant parts in question. The properties of flours are therefore also influenced by the starch present in the flour in question. Plant cells according to the invention and plants according to the invention synthesize an altered starch in comparison to corresponding wild-type plant cells which are not genetically modified or wild-type plants which are not genetically modified. Flours produced from plant cells according to the invention, plants according to the invention, propagation material according to the invention or harvestable parts according to the invention therefore have altered properties. The properties of flours can also be influenced by mixing starch with flours or by mixing flours having different properties.

A further subject of the present invention therefore relates to flours comprising a starch according to the invention.

A further subject of the present invention relates to flours which can be produced from plant cells according to the invention, plants according to the invention, starch-storing parts of plants according to the invention, from propagation material according to the invention or from harvestable plant parts according to the invention. Preferred starch-storing parts of plants according to the invention for the production of flours are tubers, storage roots and grains containing an endosperm. In connection with the present invention, grains from plants of the (systematic) family Poaceae are particularly preferred, grains from corn, rice or wheat plants are in particular preferred.

The term "flour" should be understood in connection with the present invention as meaning a powder obtained by grinding plant parts. Optionally, plant parts are dried before grinding and comminuted and/or sieved after grinding.

Flours according to the invention are distinguished on the basis of the starch according to the invention present in them, by virtue of the fact that they have an altered phosphate content and/or an increased hot water swelling power. This is desired, for example, in the processing of flours in the food industry for many applications, in particular in the production of baked goods.

A preferred subject of the present invention relates to flours produced from grains of a monocotyledonous plant, which have a hot water swelling power of at least 28 g/g, preferably of at least 33 g/g, particularly preferably of at least 38 g/g and in particular preferably of at least 43 g/g.

The determination of the hot water swelling power of flours is carried out here analogously to the method already described for the determination of the hot water swelling power of starch, with the difference that flours are employed here instead of starch. A preferred method for the determination of the hot water swelling power of flours is described under General Methods, item 1.

A further subject of the present invention is a process for the production of flours, comprising the step of the grinding of plant cells according to the invention, plants according to the invention, of parts of plants according to the invention, starch-storing parts of plants according to the invention, propagation material according to the invention or harvestable material according to the invention.

Flours can be produced by grinding starch-storing parts of plants according to the invention. It is known to the person skilled in the art how he produces flours. Preferably, a process for the production of flours also includes the step of the harvesting of the cultivated plants or plant parts and/or of the propagation material or of the starch-storing parts of these plants before grinding and particularly preferably furthermore the step of the cultivation of plants according to the invention before harvesting.

In a further embodiment of the present invention, the process for the production of flours includes a processing of plants according to the invention, of starch-storing parts of plants according to the invention, of propagation material according to the invention or of a harvestable material according to the invention before grinding.

The processing here can be, for example, a heat treatment and/or a drying. The heat treatment followed by drying of the heat-treated material is used, for example, in the production of flours from storage roots or tubers such as, for example, from potato tubers before grinding takes place. The comminution of plants according to the invention, of starch-storing parts of plants according to the invention, of propagation material according to the invention or of harvestable material according to the invention before grinding can likewise be processing within the meaning of the present invention. The removal of plant tissue, such as, for example, of chaff from the grains, before grinding, is also processing before grinding within the meaning of the present invention.

In a further embodiment of the present invention, the process for the production of flours includes processing of the grist after grinding.

The grist can here be sieved, for example, after grinding in order, for example, to produce various types of flours.

A further subject of the present invention is the use of genetically modified plant parts according to the invention, plants according to the invention, of parts of plants according to the invention, starch-storing parts of plants according to the invention, propagation material according to the invention or harvestable material according to the invention for the production of flours.

Description of the Sequences

SEQ ID NO 1: Nucleic acid sequence encoding a protein having the activity of a glucan-water dikinase from *Solanum tuberosum*.

SEQ ID NO 2: Amino acid sequence of the protein encoded by SEQ ID NO 1 having the activity of a glucan-water dikinase from *Solanum tuberosum*.

SEQ ID NO 3: Nucleic acid sequence encoding a protein having the activity of a glucan-water dikinase from *Curcuma longa*.

SEQ ID NO 4: Amino acid sequence of the protein encoded by SEQ ID NO 3 having the activity of a glucan-water dikinase from *Curcuma longa*.

SEQ ID NO 5: Nucleic acid sequence encoding a protein having the activity of a starch synthase II from *Triticum aestivum*.

SEQ ID NO: 6: Amino acid sequence of the protein encoded by SEQ ID NO: 5, having the activity of a starch synthase II from *Triticum aestivum*.

GENERAL METHODS

Figure 1:
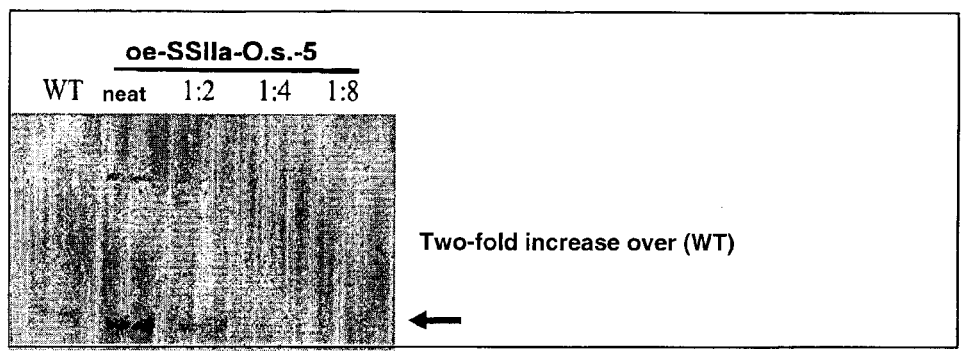
FIG. 1 shows zymograms for the determination of the activity of proteins having the activity of a starch synthase II in comparison to the wild-type. Total protein extracts of immature grains (15 days after beginning of flowering) of wild-type plants (WT) and those of three genetically modified plants (oe-SSII-O.s.-5, oe-SSII-O.s.-12, oe-SSII-O.s.-19) produced independently of one another from transformation using the expression vector AH32-191 were used. In the tracks WT and pur (undiluted), equal amounts of protein of the respective extracts are in each case applied. The protein extracts of the genetically modified plants were diluted sequentially (1:2, 1:4, 1:6, 1:8, 1:10, 1:20 or 1:100) and these dilutions were likewise separated from one another electrophoretically. By comparison of the intensity of the specific products synthesized by a protein having the activity of a starch synthase II present in the zymograms after staining with Lugol's solution (marked by an arrow) of protein extracts from wild-type plants with the intensity of the bands of protein extracts from genetically altered plants in question, the increase in the activity of a starch synthase II compared to wild-type plants can be determined. Equal intensities mean equal activities here.
Figure 1:
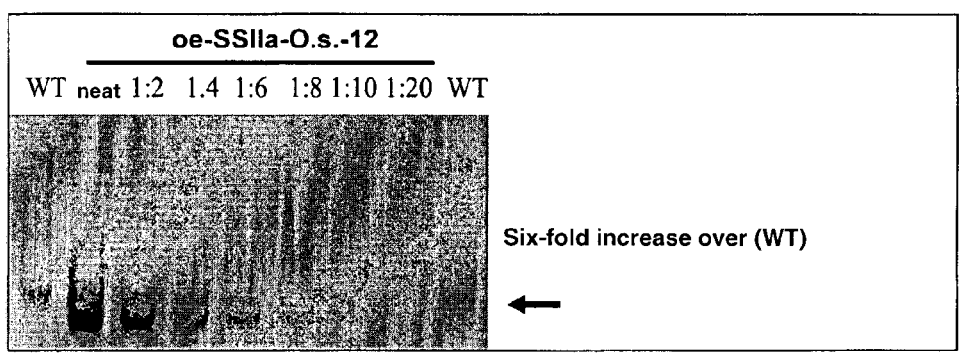
Figure 1:
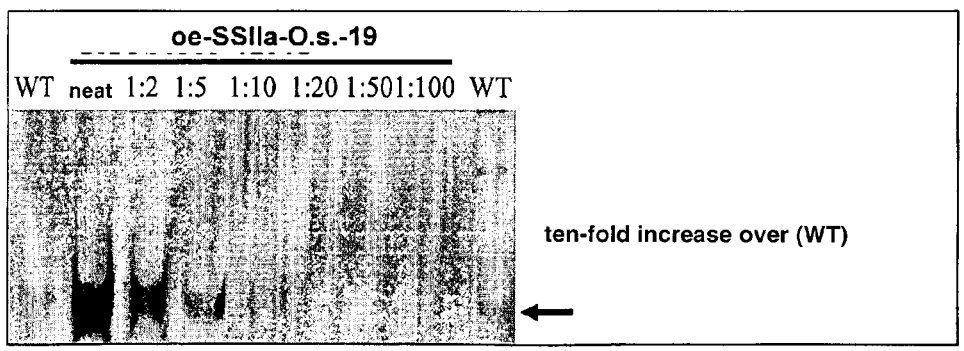

Methods are described below which can be used for carrying out the processes according to the invention. These methods are actual embodiments of the present invention, but do not restrict the present invention to these methods. It is known to the person skilled in the art that he can carry out the invention in identical manner by modification of the described methods and/or by replacing individual parts of methods by alternative parts of methods. The contents of all cited publications are additionally included in the description of the application by reference.

1. Determination of the Hot Water Swelling Power (SP)

100 mg of sample (starch or flour) are suspended in 6 ml of water and subsequently swollen at 92.5° C. for 20 minutes. During the incubation of the sample at 92.5° C., the suspension is repeatedly mixed (for the first 2 minutes continuously, after 3, 4, 5,10, 15 or 25 minutes) by careful rotation of the sample containers by 360°. After incubation at 92.5° C. for a total of 30 minutes, the suspension is cooled in ice water for about 1 minute before incubation at 25° C. for 5 minutes is carried out. After centrifugation (room temperature, 1000×g, 15 minutes), the supernatant obtained is carefully drawn off from the gelatinous sediment and the weight of the sediment is determined. The hot water swelling power is calculated according to the following formula:

$$SP = \text{(weight of the gelatinous sediment)} / \text{(weight of the sample weighed in (flour or starch))}$$

2. Determination of the Contents of Starch Phosphate a) Determination of the Phosphate Content in the C6 Position of the Glucose Molecules In starch, the positions C2, C3 and C6 of the glucose units can be phosphorylated. For the determination of the C6 P content of the starch or of the flour (modified according to Nielsen et al., 1994, Plant Physiol. 105: 111-117), 50 mg of rice/maize flour or rice/maize starch were hydrolyzed at 95° C. in 500 µl of 0.7 M HCl for 4 h with continuous shaking. Subsequently, the batches were centrifuged at 15,500×g for 10 min and the supernatants were purified from suspended matter and turbidity by means of a filter membrane (0.45 µm). 20 µl of the clear hydrolyzate were mixed with 180 µl of imidazole buffer (300 mM imidazole, pH 7.4; 7.5 mM $MgCl_2$, 1 mM EDTA and 0.4 mM NADP) and the samples were measured at 340 nm in a photometer. After determination of the base absorption, an enzyme reaction was started by addition of 2 units each of glucose 6-phosphate dehydrogenase (from *Leuconostoc mesenteroides*, Boehringer Mannheim). The measured change (OD) is based on an equimolar reaction of glucose 6-phosphate and NADP to give 6-phosphogluconate and NADPH, the formation of the NADPH being detected at the abovementioned wavelength. The reaction was monitored until reaching an endpoint. The content of glucose 6-phosphate in the hydrolyzate can be calculated from the result of this measurement:

nmol of glucose 6-phosphate/mg $FW$ =

$$= \frac{OD \times \text{measured volume (200 µl)} \times \text{volume of hydrolyzate (500 µl)}}{\text{Extinction coefficient} \times \text{volume of measured sample (20 µl)} \times \text{mg of weighed sample (50 mg)}}$$

In order not to obtain erroneous results due to incomplete hydrolysis of the starch in the material weighed (flour or starch), the degree of hydrolysis was subsequently determined. For this, 10 µl of hydrolyzate was taken from the respective hydrolyzates measured with respect to glucose 6-phosphate, neutralized with 10 µl of 0.7 M NaOH, brought to a final volume of 2 ml with water and diluted 1:100 with water. 4 µl of this dilution were treated with 196 µl of measuring buffer (100 mM imidazole pH 6.9; 5 mM MgCl$_2$, 1 mM ATP, 0.4 mM NADP) and used for the photometric determination of the glucose content. After determination of the base absorption at 340 nm, the reaction was monitored in the photometer (340 nm) by addition of 2 µl of enzyme mix (hexokinase 1:10; glucose 6-phosphate dehydrogenase from yeast 1:10; in measuring buffer) until reaching the endpoint. The measurement principle corresponds to the first reaction. From the measurements obtained, the amount of glucose can be calculated for the respective sample:

mmol of glucose/g $FW$ =

$$= \frac{OD \times \text{measured volume (200 µl)} \times \text{volume of hydrolyzate (500 µl)} \times \text{total volume of dilution (2 ml)}}{\text{Extinction coefficient} \times \text{volume of measured sample (20 µl)} \times \text{volume employed for dilution (10 µl)} \times \text{mg of weighed sample (50 mg)}}$$

The amount of glucose of the individual samples detected corresponds here to the proportion of starch which is available for the C6 phosphate determination. For simplification, the glucose content is converted to starch content in the further calculation.

Starch content (%) =

$$= \frac{\text{Glucose content (mmol g } FW\text{)} \times \text{molecular weight of glucose in starch (162 g/mol)} \times \text{conversion factor (\% = 100)}}{\text{Conversion factor (mmol to mol = 1000)}}$$

Subsequently, the result of the glucose 6-phosphate measurement is related to the starch content of the corresponding sample in order to express the content of glucose 6-phosphate per mg of hydrolyzed starch:

nmol of $Glc$ 6-$P$/mg of starch =

$$= \frac{\text{nmol of glucose 6-phosphate/mg of weighed sample} \times 100}{\text{Starch content} \left( \frac{\text{mg of starch}}{100 \text{ mg of weighed sample}} \right)}$$

Other than with reference to the amount of glucose 6-phosphate in the weighed weight of the sample (flour or starch), by this manner of calculation the amount of glucose 6-phosphate is only related to the part of the starch which was completely hydrolyzed to glucose.

b) Determination of the Total Phosphate Content

The determination of the total phosphate content was carried out according to the method of Ames (Methods in Enzymology VIII, (1966), 115-118).

About 50 mg of starch are treated with 30 µl of ethanolic magnesium nitrate solution and the mixture is incinerated in a muffle furnace at 500° C. for three hours. The residue is treated with 300 µl of 0.5 M HCl and incubated at 60° C. for 30 min. Subsequently, an aliquot is made up to 300 µl with 0.5 M HCl, added to a mixture of 100 µl of 10% strength ascorbic acid and 600 µl of 0.42% ammonium molybdate in 2M sulfuric acid and incubated at 45° C. for 20 min.

3. Transformation of Rice Plants

Rice plants were transformed according to the method described by Hiei et al. (1994, Plant Journal 6(2), 271-282).

4. Transformation of Wheat Plants

Wheat plants were transformed according to the method described by Becker et al. (1994, Plant Journal 5, 299-307).

5. Transformation of Corn Plants

Immature embryos of corn plants of the line A188 were transformed according to the method described by Ishida et al. (1996, Nature Biotechnology 14, 745-750).

6. Processing of Rice Grains and Production of Rice Flours

For the production of adequate amounts of investigation material, rice plants were cultivated in a greenhouse and harvested after reaching complete maturity. For further drying, the mature rice grains were stored at 37° C. for 3-7 days.

Subsequently, the grains were freed from the husks by means of a dehusker (Laboratory Paddy sheller, Grainman, Miami, Fla., USA) and the brown rice obtained was processed by polishing for 1 minute (Pearlest Rice Polisher, Kett, Villa Park, Calif., USA) to give white rice. For investigations of the grain composition and the starch properties, the white grains were ground to give "rice flour" by means of a laboratory mill (Cyclotec, Sample mill, Foss, Denmark).

7. Extraction of Rice Starch from Rice Flour

The extraction of rice starch from rice flour was carried out following the method described in Wang and Wang (2004; Journal of Cereal Science 39: 291-296). About 10 g of rice flour were incubated at room temperature with 40 ml of 0.05% (w/v) NaOH for 16-18 hours on a shaker. Subsequently, the suspension was transferred to a Waring blender for the completion of the digestion and thoroughly mixed for 15 seconds at low speed and subsequently for 45 seconds at high speed. For the separation of larger constituents (e.g. cell wall), the suspension was passed successively through sieves having a mesh width of 125 µm and 63 µm. After centrifugation at 1500 rpm for 15 minutes (Microfuge 3.OR; Heraeus), the supernatant was poured off and the protein layer lying on the surface of the precipitate was removed using a spatula. The resulting precipitate was resuspended again in 0.05% (w/v) NaOH and the process described above was repeated. Subsequently, the precipitate was resuspended in water and the pH of the suspension was adjusted to 6.5 to 7 using HCl.

The rice starch obtained was washed with water a total of three times, each washing step comprising a sedimentation (centrifugation at 1500 rpm, 15 min, RT), discarding of the supernatant and the resuspension of the precipitate in fresh water. Before the last washing step, the pH was checked again and optionally adjusted to pH 7 using HCl. The precipitate of the last washing step was resuspended in acetone, sedimented and the supernatant was discarded. After resuspending the precipitate again in acetone, the suspension was poured into a petri dish and dried under the hood at room temperature for at least 18 hours.

In a last step, the rice starch thus obtained was converted by grinding in a mortar to a fine powder, which can be employed directly for further investigations.

8. Analysis of the Expression Level of a Protein by Means of Northern Blot

The expression of a nucleic acid which encodes a protein was investigated by means of Northern blot analysis. For this, three immature rice grains were harvested (about 15 days after flowering) for each independent plant obtained by means of transformation and frozen in liquid nitrogen. For homogenization, the frozen rice grains in a 96-hole microtiter plate were comminuted using a 4.5 mm steel sphere in a Retsch mill (model MM300) for 30 seconds at a frequency of 30 hertz. Subsequently, the RNA was isolated by means of a Promega RNA extraction kit according to the instructions of the manufacturer (SV 96 Total RNA Isolation System, order no. Z3505, Promega, Mannheim). The concentration of the RNA in the individual samples was determined by photometric determination of the absorption at 260 nm.

Per sample, 2 μg of RNA in each case were brought to a uniform volume and treated with an identical volume of RNA sample buffer (65% (v/v) formamide, 8% formaldehyde, 13% (v/v) gel buffer (see above), 50 μg/ml ethidium bromide). After heating (10 min, 65° C.) and immediate cooling on ice, the RNA was separated on a 1.2% (w/v) agarose gel (20 mM MOPS pH 8.0, 5 mM Na acetate, 1 mM EDTA, 6% (v/v) formaldehyde) using RNA eluting buffer (20 mM MOPS pH 8.0, 5 mM Na acetate, 1 mM EDTA) at a constant current strength of 50-80 mA for about 2 hours. Subsequently, the RNA was transferred to a Hybond-N membrane by means of a diffusion blot using 10×SSC (1.5 M NaCl, 150 mM Na citrate pH 7.0) and immobilized on the membrane by means of UV irradiation.

For the hybridization of the Northern blot for the detection of the expression of a nucleic acid molecule which encodes a protein having the activity of a starch synthase II, an about 1 kb SpeI/BspHI fragment of the plasmid AH32-191 (bp 4568-5686), which comprises the 5' region of the cDNA, encoding a protein having the activity of a starch synthase II from wheat, was used. The radiolabeling of the DNA fragment was carried out by means of the Random primed DNA labelling kit of Roche (order no. 1004 760) using 32P-alpha-dCTP according to the instructions of the manufacturer.

The nylon membrane comprising the transferred RNA was incubated for four hours at 60° C. with gentle shaking in a water bath containing hybridization buffer (250 mM Na phosphate buffer pH 7.2, 1 mM EDTA, 6% (w/v) SDS, 1% (w/v) BSA) before the radiolabeled DNA was added to the hybridization buffer. After incubation for 16 hours, the hybridization buffer was removed and the membrane was washed successively once with 3×SSC and once with 2×SSC (see above) at 60° C. with gentle shaking in a water bath for the removal of nonspecifically bound DNA molecules.

For the detection of labeled RNA, an autoradiography of the nylon membrane was carried out on an X-ray film at −70° C. for one to three days.

9. Determination of the Activity of a Protein Having the Activity of a Starch Synthase II by Means of Activity Gel (Zymogram)

The detection of the activity of proteins having the activity of a starch synthase in immature rice grains was carried out by means of activity gels (zymograms), in which protein extracts are separated in a polyacrylamide gel under native conditions and subsequently incubated with appropriate substrates. The resulting reaction product (alpha-glucan) was stained in the gel by means of Lugol's solution.

Individual immature rice grains (about 15 days after flowering) were frozen in liquid nitrogen and homogenized in 150-200 μl of cold extraction buffer (50 mM tris/HCl pH 7.6, 2.5 mM EDTA, 2 mM DTT, 4 mM PMSF, 0.1% (w/v) glycogen, 10% (v/v) glycerol). After centrifugation (15 min, 13,000 g, 4° C.), the clear supernatant was transferred to a fresh reaction vessel and an aliquot of the extract was used for the determination of the protein content according to Bradford (1976, Anal Biochem 72: 248-254).

The separation of the protein extracts was carried out by means of continuous 7.5% polyacrylamide gel (7.5% acrylamide:bisacrylamide 37.5:1; 25 mM tris/HCl pH 7.6, 192 mM glycine, 0.1% (w/v) APS, 0.05% (v/v) TEMED) using singly concentrated eluting buffer (25 mM tris/HCl, 192 mM glycine). For each sample, amounts corresponding to 15 μg of protein were applied and the electrophoresis was carried out at 4° C. for 2 to 2.5 hours. Subsequently, the gels were incubated overnight at room temperature in 15 ml of incubation buffer (0.5 mM sodium citrate pH 7.0, 25 mM potassium acetate, 2 mM EDTA, 2 mM DTT, 0.1% (w/v) amylopectin, 50 mM tricine/NaOH pH 8.5, 1 mM ADP-glucose) with continuous shaking. The staining of the starch formed was carried out by means of Lugol's solution.

In order to determine by how many fold the activity of a protein having the activity of a starch synthase II is increased in comparison to corresponding wild-type plants which are not genetically modified, protein extracts of the genetically modified lines were in each case sequentially diluted and separated electrophoretically according to the method described above. The further steps were carried out as already described above. After staining the zymograms with Lugol's solution, a visual comparison of the intensity of the stained products produced by a protein having the activity of a starch synthase II (marked by an arrow in FIG. 1) for the various dilutions of the protein extracts of the genetically modified plants with the products of the undiluted wild-type protein extracts in question was carried out. Since the intensity of the staining of the products correlates directly with the activity of a protein having the activity of a starch synthase II, bands of the products having equal intensities have the same activity. If the bands of the products of a protein having the activity of a starch synthase II in the diluted protein extract have the same intensity as the band of the products of corresponding, undiluted protein extract from wild-type plants in question, the dilution factor corresponds to the degree of increase in the activity in the genetically modified plants in question (for this compare FIG. 1).

10. Production of Plants by Means of Rice Embryos (Embryo Rescue)

Seeds are separated from the panicle and the chaff is removed. The endosperm is separated from the embryo using a scalpel and used for appropriate analyses. To improve the wettability, the embryo is treated briefly with 70% ethanol and subsequently incubated for 20 minutes in a solution comprising 10% NaOCl and a drop of commercially available detergent for sterilization.

Subsequently, the sterilization solution is removed as completely as possible and the embryo is washed with sterile demineralized water once for one minute and subsequently twice for 10 minutes in each case. The seeds are laid out in petri dishes on medium solidified using agar comprising a quarter of the salt concentration of MS medium (Murashige-Skoog medium) and 4% sucrose. Subsequently, the petri dishes are sealed with parafilm and incubated at 23° C. in the dark. After germination (about 5-7 days after laying out the embryos), the petri dishes are transferred to the light. If the hypocotyls of the seedlings have reached a length of about 2 cm, the plants are transferred to glass pots comprising MS medium solidified using agar containing 2% sucrose. After adequate root formation, the plants can be potted in soil.

11. Processing of Maize Kernels

For production of sufficient material maize plants were grown under greenhouse conditions. Fully ripe maize ears were harvested and stored at 37° C. for 3-7 days for further drying before the kernels were removed from the ears.

12. Extraction of Maize Starch

Maize starch was extracted according to the wet milling method described by the "Corn Refiners Association" (available on the world wide web at corn.org). 10-50 g maize kernels were incubated in an excess of sulphurous acid for 3 days at 50° C. to leave the protein matrix. Afterwards the kernels were washed with water and briefly dried. Milling of the kernels was done in an ultracentrifugation-mill (retsch, Germany, ZM100) with a sieve having a mesh width of 2 mm. The milled material was transferred to a glass beaker and incubated for at least 30 minutes in 20% NaCl-solution leading to sedimentation of the starch granules and a floating of the lipid-bodies in the upper phase. The upper phase comprising the germs was decanted and the sediment was again suspended in the remaining solution. In the following a further purification of the starch granules was achieved by various sieving steps. A 500 μm sieve (DIN 4188) followed by a 200 μm sieve (DIN 4188) and a 125 μm sieve (ISO 3310-1) were used, whereby the sieves were washed with 20% NaCl (2-3 l) by use of an atomizer until the droplets under the sieve did not contain starch granules any more. The starch received was sedimented over night at room temperature and the supernatant was decanted in a way that about 5 mm of supernatant over the sedimented starch remained. Afterwards the starch was transferred to centrifuge tubes and sedimented again for 10 minutes at 3500 rpm in a Heraeus Variofuge. After centrifugation the starch-protein layer on top of the sediment (often to be recognized by having a different colour) was removed with a spatula and discarded. The starch obtained was again suspended several times with 0.2 M sodium-acetate, pH 4.6, centrifuged (5 minutes, remaining parameters see above) and each time the starch-protein layer on top of the sediment was removed as described above. In the following the starch obtained was digested in a solution comprising 0.2 M sodium-acetate, pH 4.6, 1% bromelaine and 1% pesin for 1 hour under constant rotation followed by centrifugation (3000 rpm, other parameters see above). The starch-protein layer on top of the sediment was again removed as described above, the obtained sediment suspended in water and centrifuged again before the protein layer on top of the sediment was removed as described above. This washing step was in total repeated 5 times before the starch obtained was suspended in 80% ethanol and centrifuged (3000 rpm, other parameters see above). This step was repeated 4 times. Finally the starch obtained was washed once in acetone to remove the lipids. Afterwards the starch was dried at room temperature.

13. Cultivation of Maize Plants

Plant material *Zea mays*, variety A188
Cultivation Conditions in the Greenhouse:
Soil:
   80% white peat
   20% brown peat
   100 kg/m³ glass sand
   40 kg/m³ clay
   structure: fine
   pH 5.3-6.1
   basic fertilizer: 2 kg/m³ 12–12–17 (+2) and 100 g/m³ Radigen (Therafor GmbH, Isrlohn, Germany)
Pots: 10 liter container
Density: max. 6 plants/m²
Fertilization:
   1 TAB Plantosan 4 g (20–10–15+6) at 4 leave stage
   1 TAB Plantosan (see above) after additional 3 weeks
Temperature: day 22° C. to 25° C./night 16° C.
Light: 18 hours, 350-400 μEinstein/s/m
Humidity: 50% rel

EXAMPLES

1. Preparation of the Plant Expression Wector AH32-191, which Comprises a Coding Sequence for a Protein Having the Activity of a Starch Synthase II The complete coding sequence of the protein having the activity of a starch synthase II from wheat (T.a.-SSII) was excised from the plasmid pCF31 (described in WO 97 45545 under the name pTaSS1) by means of the restriction endonucleases Ec/136/I and Xho I and cloned into the plasmid IR103-123 (described in WO 05 030941) cleaved using the restriction endonucleases Eco RV and Xho I. The expression vector obtained was named AH32-191. The plant expression vector IR103-123 serves for the endosperm-specific expression of the target gene under the control of the globulin promoter from rice. The plant expression vector IR103-123 additionally contains the bar gene under the control of the CaMV35S promoter, which was used as a selection marker for the transformation of plants.

2. Production of Rice Plants which have an Increased Activity of a Protein Having the Activity of a Starch Synthase II Rice plants (variety M202) were transformed by means of *Agrobacterium* comprising the plasmid AH32-191, using the method described in Hiei et al. (1994, Plant Journal 6(2), 271-282). The plants obtained were given the name oe-SSII-O.s.-X, where X designates independent plants produced from the transformation.

3. Production of Rice Plants which have an Increased Activity of a Protein Having the Activity of a Glucan-Water Dikinase Rice plants (variety M202) were transformed by means of *Agrobacterium* comprising the plasmid pML82 (described in WO 05 095619), using the method described in Hiei et al. (1994, Plant Journal 6(2), 271-282). The plants obtained were given the name oe-GWD-O.s.-X, where X designates independent plants produced from the transformation.

4. Analysis of the Rice Plants which were Transformed Using the Expression Vector AH32-191

Rice plants produced from the transformation with the expression vector AH32-191 (TO plants) of the lines having the name oe-SSII-O.s.-X were cultivated in soil in a greenhouse. RNA was isolated from immature grains (T1 seeds) of various lines having the name oe-SSII-O.s.-X and a Northern blot analysis was carried out according to the method described under General Methods, item 8. It was possible to identify a number of lines which had an increased expression of a protein having the activity of a starch synthase II from wheat in comparison to corresponding genetically unmodified wild-type plants (see exemplary representation in FIG. 2)

Figure 2:
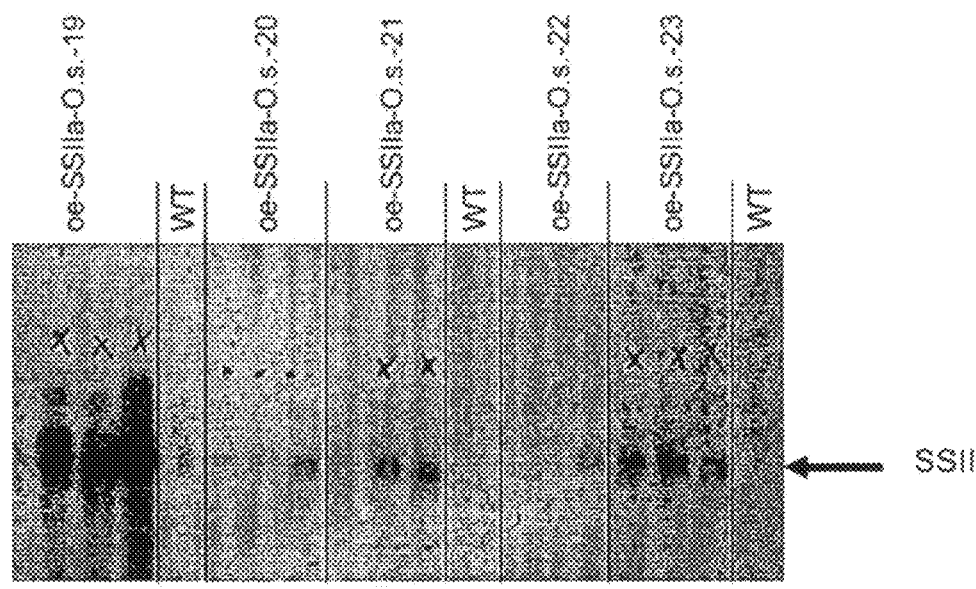
FIG. 2 shows the autoradiogram of a Northern Blot Analysis of immature T1 seeds of the rice lines oe-SSII-O.s.-19, oe-SSII-O.s.-20, oe-SSII-O.s.-21, oe-SSII-O.s.-22, oe-SSII-O.s.-23 in comparison to wild-type plants (WT) which were not genetically modified. For this, RNA was extracted from three seeds in each case of lines produced independently of the transformation using the expression vector AH32-191 and analyzed according to the method described under General Methods, item 8. The band hybridized using a labeled nucleic acid probe coding for a protein having the activity of a starch synthase II from wheat is marked by SSII.
Figure 3:
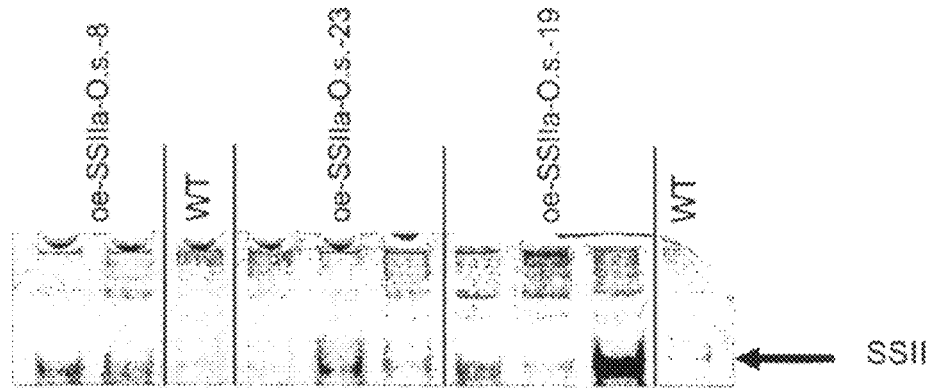
FIG. 3 shows a zymogram of protein extracts of immature T1 seeds of the rice lines oe-SSII-O.s.-8, oe-SSII-O.s.-19, oe-SSII-O.s.-23 in comparison to seeds of wild-type plants (WT) which were not genetically modified after staining with Lugol's solution. Per line, protein extracts of two (oe-SSII-O.s.-8) or three (oe-SSII-O.s.-19, oe-SSII-O.s.-23) different grains were analyzed. Analysis by means of zymogram was carried out here according to the method described under General Methods, item 9. The band in the zymogram which is specific for a protein having the activity of a starch synthase II is marked by SSII.

An increased activity of a protein having the activity of a starch synthase II in immature T1 seeds of various lines oe-SSII-O.s.-X was additionally detected by means of zymogram (see exemplary representation in FIGS. 1 and 2). The analysis by means of zymogram was carried out according to the method described under general methods, item 9.

5. Analysis of the Rice Plants which were Transformed Using the Expression Vector pML82

Rice plants produced from the transformation with the expression vector pML82 (T0 plants) of the lines having the name oe-GWD-O.s.-X were cultivated in soil in a greenhouse. Flour was produced from individual, mature grains (T1 seeds) of various lines having the name oe-GWD-O.s.-X. For this, individual grains were finely pulverized and the ground material was subsequently comminuted in a ball mill (Retsch, model MM300) for 30 seconds at a frequency of 30 hertz. Subsequently, a determination of the starch phosphate content in the C6 position of glucose molecules of the flour was carried out according to the method described under General Methods, item 2.

The following results were obtained for selected plants:

TABLE 1

Contents of phosphate bonded in the C6 position of the glucose molecules in flours, produced from individual T1 seeds of different lines having the name oe-GWD-O.s.-X in comparison to flours produced from seeds of corresponding wild-type plants (WT) of the variety M202, which were not genetically modified.

| Name of the plant | nmol of C6 phosphate per mg of fresh weight of the seeds |
|---|---|
| oe-GWD-O.s.-2 | 1.68 |
| oe-GWD-O.s.-4 | 1.70 |
| oe-GWD-O.s.-9 | 1.47 |
| WT | 0.30 |

As is evident from Table 1, it was possible using the expression vector pML82 to identify independent lines produced from the transformation, which in comparison to corresponding wild-type plants which were not genetically modified had an increased content of phosphate bonded in the C6 position of the glucose molecules in flours. Since it is known that plant cells which have an increased expression of a protein having the activity of a glucan-water dikinase synthesize a starch which has a higher starch phosphate content in comparison to corresponding genetically unmodified wild-type plants (see, for example, WO 02 34923), the increase in the phosphate content in lines having the name oe-GWD-O.s.-X is to be attributed to an increased activity of the protein having the activity of a glucan-water dikinase.

6. Production of Plants which have an Increased Activity of a Protein Having the Activity of a Starch Synthase II and an Increased Activity of a Protein Having the Activity of a Glucan-Water Dikinase 30 T1 seeds in each case of plants of various lines having the name oe-SSII-O.s.-X or of the lines oe-GWD-O.s.-X were again cultivated in a greenhouse and the plants in question were sprayed with a solution comprising 0.5% Basta® (Bayer CropScience). Approximately a quarter of the treated plants of the lines oe-SSII-O.s.-19, oe-GWD-O.s.-2, oe-GWD-O.s.-4 and oe-GWD-O.s.-9 reacted sensitively to the treatment with Basta®, which allowed it to be concluded that they contained no bar gene mediating resistance to Basta® and the T-DNA of the expression vectors was integrated at a site in the genome or at sites in the genome which lie so tightly together that they do not segregate. T2 seeds of T1 plants of these lines which were resistant to the treatment with Basta® were again laid out in the greenhouse and a treatment with Basta® was carried out as just described. Subsequently, the same treatment with Basta® was carried out with T3 plants of these lines: It was possible here to identify various T3 plants of the lines oe-GWD-O.s.-19, oe-GWD-O.s.-2, oe-GWD-O.s.-4 and oe-GWD-O.s.-9 in which all plants were resistant to Basta®. This allowed it to be concluded that T2 plants from which the T3 seeds in question originated were homozygous for the integrated T-DNA. T2 seeds of homozygous plants of the line oe-SSII-O.s.-19, oe-GWD-O.s.-2, oe-GWD-O.s.-4 and oe-GWD-O.s.-9 were again laid out and various plants of the line oe-SSII-O.s.-19 were in each case dusted with pollen of the lines oe-GWD-O.s.-2, oe-GWD-O.s.-4 and oe-GWD-O.s.-9. The crossing descendants resulting therefrom were designated by oe-SSII/GWD-O.s.-1 (oe-SSII-O.s.-19 X oe-GWD-O.s.-2), oe-SSII/GWD-O.s.-2 (oe-SSII-O.s.-19 X oe-GWD-O.s.-4) and oe-SSII/GWD-O.s.-3 (oe-SSII-O.s.-19 X oe-GWD-O.s.-9).

7. Analysis of Plants which have an Increased Activity of a Protein Having the Activity of a Starch Synthase II and an Increased Activity of a Protein Having the Activity of a Glucan-Water Dikinase Of the lines oe-SSII/GWD-O.s.-1, oe-SSII/GWD-O.s.-2, oe-SSII/GWD-O.s.-3 produced from crossings and homozygous parent plants (oe-SSII-O.s.-19, oe-GWD-O.s.-2, oe-GWD-O.s.-4 and oe-GWD-O.s.-9), individual F1 seeds were in each case harvested, and the embryos were separated and stored at room temperature. Flour, obtained from the remaining endosperm of the respective individual F1 seeds, was investigated using the method described under General Methods, item 6 for the content of phosphate bound in the C6 position of the glucose molecules. The following results were obtained.

TABLE 2

Contents of phosphate bonded in the C6 position of the glucose molecules in flours, produced from individual F1 seeds of lines having the name oe-SSII/GWD-O.s.-X, in comparison to flours produced from individual seeds of corresponding wild-type plants of the variety M202 (WT) which were not genetically modified. The content of phosphate bonded in the C6 position of the glucose molecules in flours produced from individual homozygous seeds of the parent lines is likewise shown.

| Name of the plant | No. of the F1 seed | nmol of C6 phosphate per mg of starch |
|---|---|---|
| oe-SSII/GWD-O.s.-1 | 1 | 6.5 |
| | 2 | 2.8 |
| | 3 | 2.6 |
| | 4 | 2.5 |
| | 5 | 2.6 |
| oe-SSII/GWD-O.s.-2 | 1 | 7.9 |
| | 2 | 7.2 |
| | 3 | 7.1 |
| | 4 | 8.4 |
| | 5 | 6.9 |
| oe-SSII/GWD-O.s.-3 | 1 | 6.7 |
| | 2 | 6.0 |
| | 3 | 7.7 |
| | 4 | 7.5 |
| | 5 | 7.0 |
| oe-SSII-O.s.-19 (mother) | 1 | 1.5 |
| | 2 | 1.4 |
| oe-GWD-O.s.-2 (father 1) | 1 | 3.6 |
| oe-GWD-O.s.-4 (father 2) | 1 | 3.5 |
| oe-GWD-O.s.-9 (father 3) | 1 | 4.1 |

TABLE 2-continued

Contents of phosphate bonded in the C6 position of the glucose molecules in flours, produced from individual F1 seeds of lines having the name oe-SSII/GWD-O.s.-X, in comparison to flours produced from individual seeds of corresponding wild-type plants of the variety M202 (WT) which were not genetically modified. The content of phosphate bonded in the C6 position of the glucose molecules in flours produced from individual homozygous seeds of the parent lines is likewise shown.

| Name of the plant | No. of the F1 seed | nmol of C6 phosphate per mg of starch |
|---|---|---|
| WT | 1 | 0.5 |
|    | 2 | 0.5 |

Embryos of seeds of the lines oe-SSII/GWD-O.s.-X, whose flours had a content of phosphate bonded in the C6 position of the glucose molecules of at least 6.0 nmol of C6 phosphate per mg of starch, were germinated by means of the method described under General Methods item 10 and subsequently cultivated in a greenhouse for the production of F2 seeds. For the identification of the descendants which were homozygous for the two integrated T DNAs, mediating an increased activity of a protein having the activity of a starch synthase II or mediating an increased activity of a protein having the activity of a glucan-water dikinase, the process just described for F1 seeds was repeated with F2 seeds. Subsequently, in turn embryos of seeds whose flours had a content of phosphate bonded in the C6 position of the glucose molecules of at least 6.0 nmol of C6 phosphate per mg of fresh weight of the seed were germinated and cultivated in a greenhouse for the production of F3 seeds. The following results were obtained for individual F3 seeds, originating from an F2 plant in each case:

TABLE 3

Content of phosphate bonded in the C6 position of the glucose molecules in flours, produced from individual F3 seeds of lines having the name oe-SSII/GWD-O.s.-X; which were prepared by crossing the parent lines oe-SSII-O.s.-19 (mother) with plants of the lines oe-GWD-O.s.-X (father), in comparison to flours produced from individual seeds of corresponding wild-type plants of the variety M202 (WT) which were not genetically modified. The content of phosphate bonded in the C6 position of the glucose molecules in flours produced from individual homozygous seeds of the individual parent lines is likewise shown.

| Name of the plant | No. of the F3 seed | nmol of C6 phosphate per mg of starch |
|---|---|---|
| oe-SSII/GWD-O.s.-1 | 1 | 9.7 |
|  | 2 | 9.7 |
|  | 3 | 10.0 |
|  | 4 | 9.7 |
|  | 5 | 9.8 |
|  | 6 | 9.1 |
|  | 7 | 8.4 |
|  | 8 | 9.7 |
|  | 9 | 9.9 |
|  | 10 | 10.0 |
|  | 11 | 9.8 |
|  | 12 | 9.8 |
| oe-SSII/GWD-O.s.-2 | 1 | 10.4 |
|  | 2 | 9.8 |
|  | 3 | 10.9 |
|  | 4 | 10.1 |
|  | 5 | 11.2 |
|  | 6 | 10.0 |
|  | 7 | 11.0 |
|  | 8 | 9.7 |
|  | 9 | 10.4 |
|  | 10 | 10.5 |
|  | 11 | 11.9 |
|  | 12 | 10.6 |
| oe-SSII/GWD-O.s.-3 | 1 | 12.5 |
|  | 2 | 11.5 |
|  | 3 | 11.3 |
|  | 4 | 11.4 |
|  | 5 | 11.0 |
|  | 6 | 11.6 |
|  | 7 | 11.5 |
|  | 8 | 11.5 |
|  | 9 | 12.1 |
|  | 10 | 10.0 |
|  | 11 | 11.5 |
|  | 12 | 10.6 |
| oe-SSII-O.s.-19 (mother) | 1 | 1.5 |
|  | 2 | 1.7 |
|  | 3 | 2.2 |
|  | 4 | 1.9 |
| oe-GWD-O.s.-9 (father 3) | 1 | 3.3 |
|  | 2 | 2.9 |
|  | 3 | 3.3 |
|  | 4 | 3.3 |
| WT | 1 | 0.5 |
|  | 2 | 0.9 |

The fact that the content of phosphate bonded in the C6 position of the glucose molecules in flours produced from individual F3 seeds which in each case originated from an F2 plant of the lines in question was approximately identical indicated the fact that the F2 plants in question are homozygous for the two integrated T-DNAs. F3 seeds of F2 plants of the lines oe-SSII/GWD-O.s.-1, oe-SSII/GWD-O.s.-2, oe-SSII/GWD-O.s.-3, which were homozygous for the two integrated T DNAs mediating an increased activity of a protein having the activity of a starch synthase II or mediating an increased activity of a protein having the activity of a glucan-water dikinase, were processed to give flours according to the method described under General Methods item 6. Starch was isolated from a part of this flour according to the method described under General Methods item 7. Subsequently, the content of phosphate bonded in the C6 position of the glucose molecules was determined in flours and starch. The following results were obtained:

TABLE 4

Content of phosphate bonded in the C6 position of the glucose molecules in flours or starch, produced from seeds of homozygous plants of lines having the name oe-SSII/GWD-O.s.-X; which were produced by crossing, in comparison to flours or starch produced from seeds of the parent lines oe-SSII-O.s.-19 (mother) and oe-GWD-O.s.-X (father) or wild-type plants of the variety M202 (WT).

| Name of the plant | nmol of C6 phosphate per mg of starch | nmol of C6 phosphate per mg of starch |
|---|---|---|
| oe-SSII/GWD-O.s.-1 | 12.9 | 11.5 |
| oe-SSII/GWD-O.s.-2 | 13.4 | 12.6 |
| oe-SSII/GWD-O.s.-3 | 13.0 | 12.4 |

TABLE 4-continued

Content of phosphate bonded in the C6 position of the glucose molecules in flours or starch, produced from seeds of homozygous plants of lines having the name oe-SSII/GWD-O.s.-X; which were produced by crossing, in comparison to flours or starch produced from seeds of the parent lines oe-SSII-O.s.-19 (mother) and oe-GWD-O.s.-X (father) or wild-type plants of the variety M202 (WT).

| Name of the plant | nmol of C6 phosphate per mg of starch | nmol of C6 phosphate per mg of starch |
|---|---|---|
| oe-SSII-O.s.-19 (mother) | 1.5 | 1.2 |
| oe-GWD-O.s.-2 (father 1) | 3.9 | 3.3 |
| oe-GWD-O.s.-4 (father 2) | 3.9 | 3.5 |
| oe-GWD-O.s.-9 (father 3) | 3.9 | 3.5 |
| WT | 1.1 | 0.4 |

The determination of the hot water swelling power of flours or starches produced from F3 seeds of the lines oe-SSII/GWD-O.s.-X with respect to the T-DNA integrations of homozygous plants of the lines oe-SSII-O.s.-19 and oe-GWD-O.s.-X and of wild-type plants was carried out according to the method described under General Methods item 1. For the lines oe-SSII/GWD-O.s.-X, differing from the method described under General Methods item 1, twice the amount of water based on the amount of flour or starch was employed here since when using the amount of water indicated under General Methods item 1 with these lines no separation of the swollen substance from the aqueous supernatant was discernible. The following results were obtained:

TABLE 5

Hot water swelling power of flours or starch produced from seeds of homozygous plants of lines having the name oe-SSII/GWD-O.s.-X; which were produced by crossing, in comparison to flours or starch produced from seeds of the parent lines oe-SSII-O.s.-19 (mother) and oe-GWD-O.s.-X (father) or wild-type plants of the variety M202 (WT).

| Name of the plant | Swelling power of flour [g/g] | Swelling power of flour [g/g] |
|---|---|---|
| oe-SSIIGWD-O.s.-1 | 42.8 | 95.2 |
| oe-SSIIGWD-O.s.-2 | 41.1 | 128.3 |
| oe-SSIIGWD-O.s.-3 | 34.1 | 91.4 |
| oe-SSII-O.s.-19 (mother) | 22.6 | 36.2 |
| oe-GWD-O.s.-2 (father 1) | 20.1 | 30.8 |
| oe-GWD-O.s.-4 (father 2) | 20.0 | 36.5 |
| oe-GWD-O.s.-9 (father 3) | 17.4 | 34.0 |
| WT | 16.3 | 27.7 |

Figure 4:
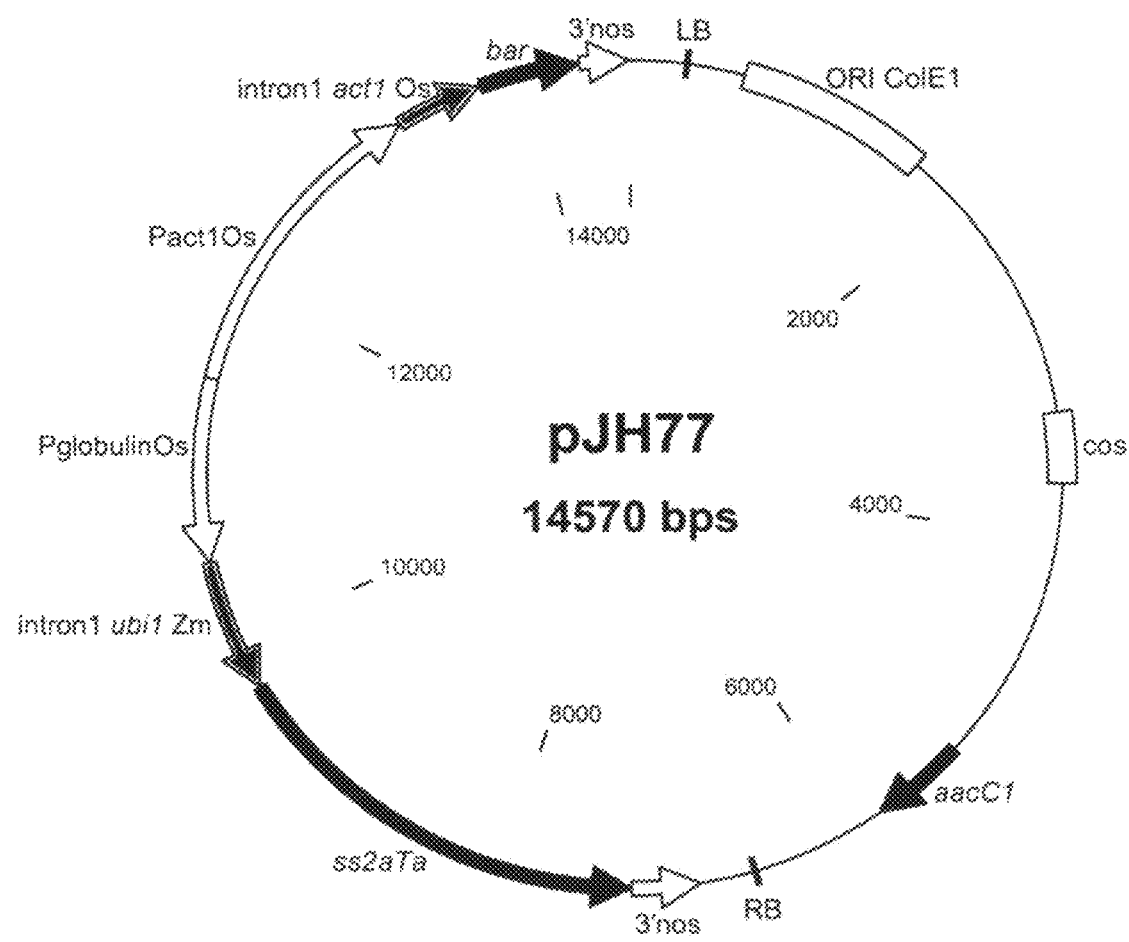
FIG. 4 shows a map of plasmid pJH77.

8. Preparation of the Plant Expression Vector pJH77, which Comprises a Coding Sequence for a Protein Having the Activity of a Starch Synthase II The complete coding sequence of the protein having the activity of a starch synthase II from wheat (T.a.-SSII) was subcloned. The plasmid obtained was designated pJH77 (see FIG. 4) and does comprise the following functional elements:

TABLE 6

Genetic elements of the plasmid pJH77.

| Nt Positions | Orientation | Origin |
|---|---|---|
| 6600-6623 | | RB: right border T-DNA from *Agrobacterium tumefaciens* (Zambryski, 1988) |
| 6624-6909 | | Remaining TL-DNA of pTiAch5, flanking the right border (Gielen et al., 1984) |

TABLE 6-continued

Genetic elements of the plasmid pJH77.

| Nt Positions | Orientation | Origin |
|---|---|---|
| 6910-7285 | counter clockwise | 3'nos: sequence comprising the 3'-untranslated region of the nopalinsynthase-gene from the T-DNA of plasmid pTiT37 (Depicker et al., 1982) |
| 7286-9685 | counter clockwise | ss2aTa: coding sequence of the protein having the activity of a starch synthase II from wheat (T.a.-SSII) from *Triticum aestivum* (wheat) (SEQ ID No. 5) |
| 9686-10437 | counter clockwise | intron1 ubi1 Zm: first Intron of the ubiquitin-1 gene (ubi1) from *Zea mays* (Christensen et al., 1992). |
| 10438-11478 | counter clockwise | PglobulinOs: sequence comprising the promoter region of the globulin-1 gene from *Oryza sativa* (rice) (Hwang et al. (2002)) |
| 11479-13261 | clockwise | Pact1Os: sequence comprising the promoter region of the actin-1 gene from *Oryza sativa* (rice) (Mc Elroy et al., 1990). |
| 13262-13739 | clockwise | intron1 act1 Os: first intron of the actin-1 gene from *Oryza sativa* (rice) (Mc Elroy et al., 1990). |
| 13740-14291 | clockwise | bar: coding seqwuence of the phosphinothricin acetyltransferase gene of *Streptomyces hygroscopicus* (Thompson et al. (1987)) |
| 14292-14561 | clockwise | 3'nos: sequence comprising the 3'-untranslated region of the nopalinsynthase gene of the T-DNA of plasmid pTiT37 (Depicker et al., 1982) |
| 14562-296 | | Remaining TL-DNA of pTiAch5, flanking the left border (Gielen et al., 1984) (Gielen et al., 1984) |
| 297-320 | | LB: left border T-DNA from *Agrobacterium tumefaciens* (Zambryski, 1988) |

TABLE 7

References cited in Table 6.

Christensen A. H., Sharrock R. A., Quail P. H. (1992). Maize polyubiquitin genes: structure, thermal pertubation of expression and transcript splicing, and promoter activity following transfer to protoplasts by electroporation. Plant Molecular Biology, 18, 675-689.
Depicker A., Stachel S., Dhaese P., Zambryski P., Goodman H. M. (1982). Nopaline synthase: transcript mapping and DNA sequence. Journal of Molecular and Applied Genetics, 1, 561-573.
Gielen J.; De Beuckeleer M.; Seurinck J.; Deboeck F.; De Greve H.; Lemmers M.; Van Montagu M.; Schell J. (1984). Isolation of an efficient actin promoter for use in rice transformation. The EMBO journal, 3, 835-846
Hwang Y.-S., Yang D., McCullar C., Wu L., Chen L., Pham P., Nandi S., Huang N. (2002). Analysis of the rice-endosperm-specific globulin promoter in transformed rice cells. Plant Cell Rep 20, 842-847.
Leroux B., Pelissier B., Lebrun M. (1996). Chimeric herbicide resistance gene. U.S. Pat. No. 5,559,024 (24 Sep. 1996), RHONE POULENC AGROCHIMIE (FR).
Mc Elroy D., Zhang W., Cao J., Wu R. (1990). Isolation of an efficient actin promoter for use in rice transformation. The Plant Cell, 2, 163-171.
Thompson C. J., Rao Movva N., Tizard R., Crameri R., Davies J., Lauwereys M., Botterman J. (1987). Characterization of the herbicide resistance gene bar from *Streptomyces hygroscopicus*. The EMBO Journal, 6, 2519-2523.
Zambryski P. (1988). Basic processes underlying *Agrobacterium*-mediated DNA transfer to plant cells. Annual Review of Genetics, 22, 1-30.

9. Production and Identification of Maize Plants which have an Increased Activity of a Protein Having the Activity of a Starch Synthase II Maize plants (variety A188) were transformed with plasmid pJH77 according to the method described under General Methods, item 5. The plants obtained were given the name JH77-X, where X designates independent plants produced from the transformation. Plants originating from the transformation with the plasmid JH77 (T0 plants) were grown in the greenhouse and pollinated with pollen from wildtype plants (variety A188).

Figure 5:
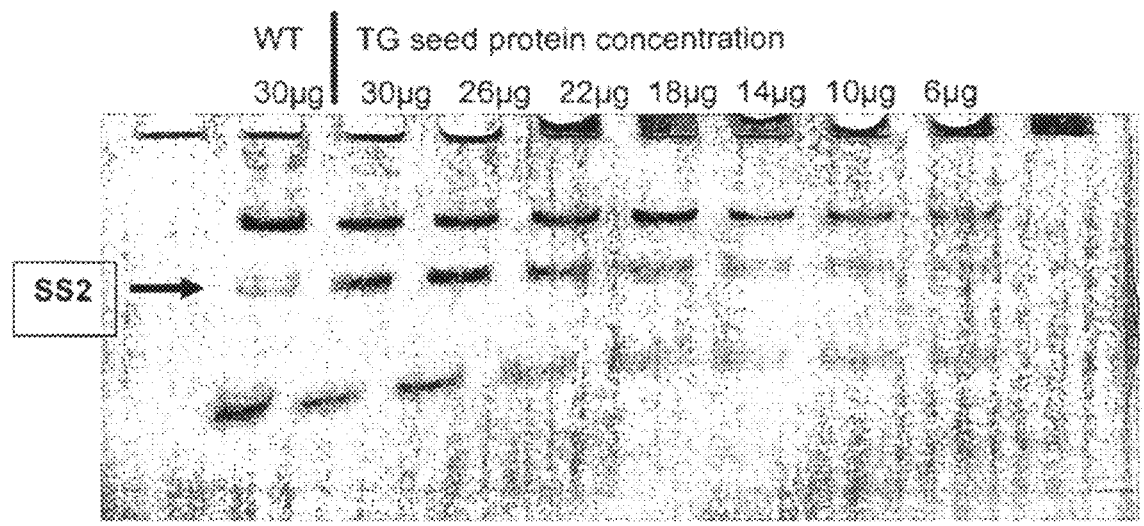
FIG. 5 shows a zymogram of protein extracts from immature maize kernels of wildtype plants (WT) and from a transgenic line (TG) having an increased activity of a protein having the activity of a starch synthase II (SS2). Indicated is the protein amount supplied.
Figure 6:
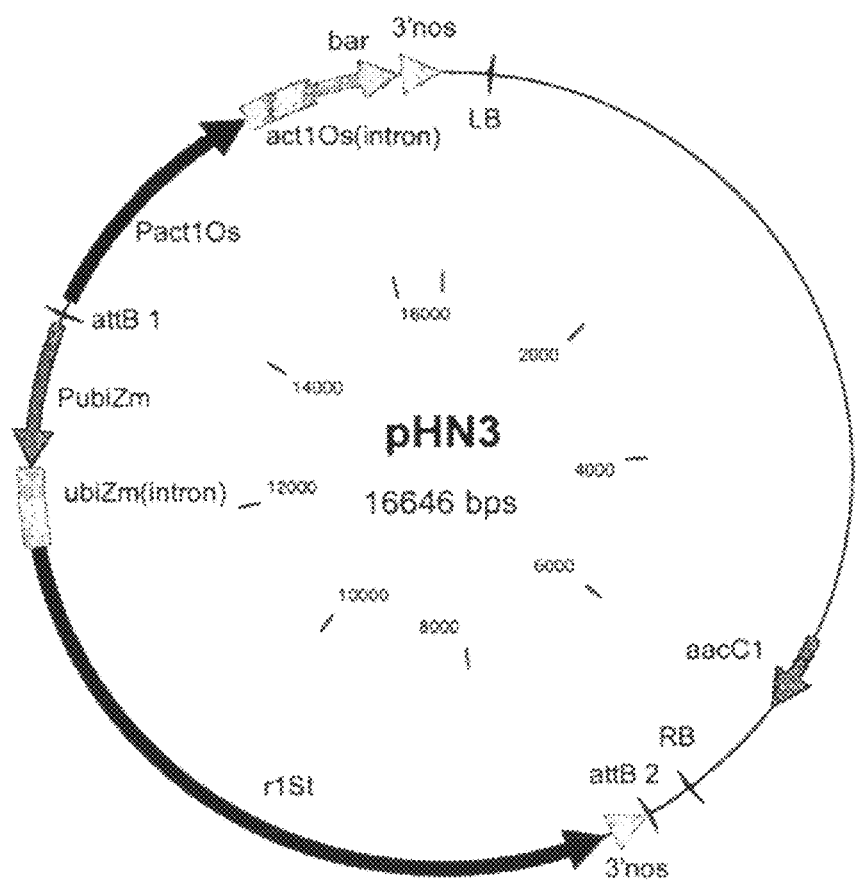
FIG. 6 shows a map of plasmid pHN3.

Protein was extracted from single unripe (ca. 15 days after pollination) kernels (T1 kernels) from independent plants obtained after transformation with the plasmid pJH77 and crosspollination with wildtype as well as from non-transformed wildtype plants (A188). The respective protein extracts of various plants were analyzed in zymograms according to the method described under General Methods, item 9. For quantification of the increase in activity of the protein having the activity of an SS II, protein extracts from transgenic lines were sequentially diluted. The result of such an analysis is exemplified by FIG. 5. Several plants showed an increase of activity of the protein having the activity of a starch synthase II of a factor between 3 and 5 in comparison to wildtype plants (A188).

10. Preparation of the Plant Expression Vector pHN3, which Comprises a Coding Sequence for a Protein Having the Activity of a Glucan-Water Dikinase The vector pHN3 (FIG. 7) is derived from pRPA-BL150-Aα2 (EP0337899). The vector backbone contains the following genetic elements:

TABLE 8

Genetic elements of the plasmid pHN3.

| Nt Positions | Orientation | Origin |
| --- | --- | --- |
| 6600-6623 | | RB: right border repeat from the T-DNA of *Agrobacterium tumefaciens* (Zambryski, 1988) |
| 6624-6909 | | TL-DNA of pTiAch5 (Gielen et al., 1984) |
| 6910-6934 | | attB2: variant of the recognition sequence attB of *Escherichia coli* (Hartley et al., 2000) |
| 6935-7254 | counter clockwise | 3'nos: sequence including the 3' untranslated region of the nopaline synthase gene from the T-DNA of pTiT37 (Depicker et al., 1982) |
| 7255-11984 | counter clockwise | r1St: coding sequence of the r1 gene of *Solanum tuberosum* (Lorberth et al., 1998) |
| 11985-12504 | counter clockwise | ubi1Zm(intron): first intron of the ubiquitin-1 gene of *Zea mays* (corn) (Christensen et al., 1992) |
| 12505-13537 | counter clockwise | PubiZm: sequence including the promotor region of the ubiquitin-1 gene of *Zea mays* (corn) as described by Christensen et al., 1992 |
| 13538-13562 | | attB1: variant of the recognition sequence attB of *Escherichia coli* (Hartley et al., 2000) |
| 13563-15337 | clockwise | Pact1Os: sequence including the promotor region of the actin 1 gene of *Oryza sativa* (McElroy et al., 1990) |
| 15338-15815 | clockwise | act1Os(intron): sequence including the intron of the actin 1 gene of *Oryza sativa* (McElroy et al., 1990) |
| 15816-16367 | clockwise | bar: the coding sequence of the phosphinothricin acetyltransferase gene of *Streptomyces hygroscopicus* as described by Thompson et al. (1987) |
| 16368-16638 | clockwise | 3'nos: sequence including the 3' untranslated region of the nopaline synthase gene from the T-DNA of pTiT37 (Depicker et al., 1982) |
| 16639-296 | | TL-DNA of pTiAch5 (Gielen et al., 1984) |
| 297-320 | | LB: left border repeat from the T-DNA of *Agrobacterium tumefaciens* (Zambryski, 1988) |

TABLE 9

References cited in Table 8.

Bolivar, F., Rodriguez, R. L., Greene, P. J., Betlach, M. C., Heyneker, H. L., Boyer, H. W., Crosa, J., Falkow, S. (1977).
Construction and characterization of new cloning vehicles. II. A multipurpose cloning system. Gene, 2, 95-113.
Christensen, A. H., Sharrock, R. A., Quail, P. H. (1992).
Maize polyubiquitin genes: structure, thermal perturbation of expression and transcript splicing, and promoter activity following transfer to protoplasts by electroporation. Plant Mol. Biol. 18 (4), 675-689.

TABLE 9-continued

References cited in Table 8.

Depicker, A., Stachel, S., Dhaese, P., Zambryski, P., Goodman, H. M. (1982). Nopaline synthase: transcript mapping and DNA sequence. Journal of Molecular and Applied Genetics, 1, 561-573.
Gielen, J., De Beuckeleer, M., Seurinck, J., Deboeck, F., De Greve, H., Lemmers, M., Van Montagu, M., Schell, J. (1984). The complete nucleotide sequence of the TL-DNA of the *Agrobacterium tumefaciens* plasmid pTiAch5. The EMBO Journal, 3, 835-846.
Hartley J., Temple G., Brasch M. (2000). DNA cloning using in vitro site-specific recombination. Genome Research, 10, 1788-1795.
Lorberth R, Ritte G, Willmitzer L, Kossmann J (1998). Inhibition of a starch-granule-bound protein leads to modified starch and repression of cold sweetening. Nature Biotechnology 16, 473-477.
McElroy, D., Zhang, W., Cao, J., Wu, R. (1990).
Isolation of an efficient actin promoter for use in rice transformation. Plant Cell 2 (2), 163-171.
Rhone Poulenc Agro EP0337899 B1
Thompson, C. J., Rao Movva, N., Tizard, R., Crameri, R., Davies, J., Lauwereys, M., Bottermann, J. (1987). Characterization of the herbicide resistance gene bar from *Streptomyces hygroscopicus*. EMBO J., 6, 2519-2523.
Wohlleben W, Arnold W, Bissonnette L, Pelletier A, Tanguay A, Roy PH, Gamboa GC, Barry GF, Aubert E, Davies J, (1989). On the evolution of Tn21-like multiresistance transposons: sequence analysis of the gene (aacC1) for gentamicin acetyltransferase-3-I(AAC(3)-I), another member of the Tn21-based expression cassette. Mol Gen Genet. 217(2-3), 202-208.
Zambryski P. (1988). Basic processes underlying *Agrobacterium*-mediated DNA transfer to plant cells. Ann. Rev. Genet. 22: 1-30.

11. Production and Identification of Maize Plants which have an Increased Activity of a Protein Having the Activity of a Glucan-Water Dikinase

*Zea mays* plants (variety A188) were transformed with the plasmid pHN3 according to the method described under General Methods, item 5. The plants obtained were given the name HN3-X, where X designates independent plants produced from the transformation.

Plants originating from the transformation with the plasmid pHN3 (T0 plants) were grown in the greenhouse and pollinated with pollen from wildtype plants (variety A188). Plants of the resulting T1 generation were grown in the greenhouse and sprayed in the three-leaf stage with a solution containing 0.5% BASTA®. Only those groups of T1 plants for which ca. 25% of the 30 cultivated plants in each case died off after spraying with the BASTA®. solution were followed further, because these plants are those for which the integration of the related T-DNA of the plasmid pHN3 is present in a single locus in the genome. Genomic DNA was isolated from leaf material from the ca. 75% of the plants that survived the spraying with BASTA®. solution and investigated in each case for the number of copies present in case by means of INVADER® technology (Pielberg et al. 2003, Genome Res.; 13, 2171-2177). The T1 plants within a group of offspring of a T0 plant that showed a signal approximately twice as strong as the remaining offspring of the same T0 plant in an analysis by means of INVADER® technology are homozygous with respect to the locus at which the T-DNA of the plasmid is integrated. If approximately 30% of the offspring of a T0 plant that survived the treatment with BASTA®. solution show a signal approximately twice as strong in the analysis by means of Invader technology, in comparison with the remaining ca. 70% of the offspring of the same T0 plant, then this is a further indication that the integration of the T-DNA is at a single locus.

The starch phosphate content was determined according to the method described under General Methods, item 2a) in starch isolated from kernels harvested from plants selected like just described. Starch, isolated from line HN3-101 did have a starch phosphate content in C6 position of 4.6 nmol per mg starch.

12. Production and Identification of Maize Plants which have an Increased Activity of a Protein Having the Activity of a Starch Synthase II and an Increased Activity of a Protein Having the Activity of a Glucan-Water Dikinase Several independent lines (JH77-X) showing different degrees in increase in the activity of a protein having the activity of a starch synthase II were used for crossing with plants from line HN3-101, which was homozygous in respect to the integration of the T-DNA from plasmid pHN3. The plants designated HN3-101 were used as pollen donor (male crossing partner and plants of the lines JH77-X were used as female crossing partner. F1 plants originating from these crossings were grown in the green house, DNA was extracted from leaves. Various F1 plants could be selected with the aid of PCR which did carry both transgenes. Various F2 plants from each of these plants were grown in the greenhouse and genomic DNA was isolated from leaf material and investigated in each case for the number of copies present for both of the transgenes by means of INVADER® technology (Pielberg et al. 2003, Genome Res.; 13, 2171-2177). The F2 plants within a group of offspring of a F1 plant that showed a signal approximately twice as strong as the remaining offspring of the same F1 plant in an analysis by means of INVADER® technology are to be seen to be homozygous with respect to the respective loci at which the T-DNAs of both the plasmids is integrated.

The following table shows the origin of plants which have been selected as just described:

TABLE 10

Origin of plants which were obtained after crossing plants from the line HN3-101 and JH77-X.

| Male crossing partner | Female crossing partner | Designated name of selected F2 plant |
|---|---|---|
| HN3-101 | JH77-01903 | Cross-13 |
| HN3-101 | JH77-02101 | Cross-49 |

13. Analysis of Starch from Plants Having an Increased Activity of a Protein Having the Activity of a Starch Syntahse II and an Alpha-Glucan-Water Dikinase Ripe ears from the paints designated Cross-13 and Cross-49 were harvested, further dryed as described under General Methods, item 11. Strach was extracted from the kernels as described under General Methods, item 12. Starch Phosphate content in these starches was analysed according to the method described under General Methods, item 2a) and hot water swelling power was analysed as described under General Methods, item 1. The following results were obtained:

TABLE 11

Starch phosphate content and swelling power of starch isolated from plants having an increased activity of a protein having the activity of a starch synthase II (JH77-01903, JH77-02101), an increased activity of a protein having the activity of a alpha-glucan-water dukinase (HN3-101) or from plants having an increased activity of both proteins (Cross-13, Cross-49) in comparison to wildtype plants (A188-105, A188-114).

| Name of the plant | nmol of C6 phosphate per mg of starch | Swelling power of starch [g/g] |
|---|---|---|
| A188-105 | 0.34 | 28.2 |
| A188-114 | 0.13 | 30.8 |
| JH77-01903 | 0.16 | 22.0 |
| JH77-02101 | 0.16 | 22.2 |
| HN3-101 | 4.70 | 42.3 |
| Cross-13 | 6.49 | 48.6 |
| Cross-49 | 5.97 | 47.4 |

The invention claimed is:

1. A genetically modified plant cell comprising a foreign nucleic acid encoding a protein having the activity of a starch synthase II and a foreign nucleic acid encoding a protein having the activity of a glucan-water dikinase, wherein said starch synthase II activity and said glucan-water dikinase activity is increased in comparison to genetically unmodified wild-type plant cells.

2. The genetically modified plant cell of claim 1, wherein said cell which synthesizes a modified starch in comparison to starch isolated from corresponding wild-type plant cells which are not genetically modified.

3. The genetically modified plant cell of claim 2, wherein the modified starch has a hot water swelling power of at least 110 g/g.

4. A plant comprising the genetically modified plant cell of claim 3.

5. The genetically modified plant cell of claim 2, wherein the modified starch has a hot water swelling power of at least 120 g/g.

6. A plant comprising the genetically modified plant cell of claim 5.

7. The genetically modified plant cell of claim 2, wherein plant cell is a corn plant cell and the modified starch from said corn plant cell has a hot water swelling power of at least 45 g/g.

8. A plant comprising the genetically modified plant cell of claim 7.

9. The genetically modified plant cell of claim 2, wherein the modified starch has a phosphate content that is increased at least 10-fold compared to starch isolated from corresponding wild-type plant cells.

10. The genetically modified plant cell of claim 2, wherein the modified starch has at least 10-fold more starch phosphate in the C6 position of the glucose molecules of the starch than starch isolated from corresponding wild-type plant cells.

11. The genetically modified plant cell of claim 1, wherein said cell synthesizes a starch having an increased hot water swelling power in comparison to starch synthesized by corresponding wild-type plant cells.

12. The genetically modified plant cell of claim 11, wherein the starch has a hot water swelling power that is increased by at least a factor of two compared to starch from a corresponding wild-type plant cell.

13. A plant comprising the genetically modified plant cell of claim 12.

14. The genetically modified plant cell of claim 11, wherein the starch has a hot water swelling power is increased by at least a factor of four compared to starch from a corresponding wild-type plant cell.

15. A plant comprising the genetically modified plant cell of claim 14.

16. A plant comprising the genetically modified plant cell of claim 1.

17. Propagation material of the plant of claim 16, wherein said propagation material comprises said nucleic acid encoding a protein having the activity of a starch synthase II and said nucleic acid encoding a protein having the activity of a glucan-water dikinase.

18. A process for the production of flours comprising grinding of a plant of claim 16.

19. A process for the production of a modified starch comprising extracting starch from the plant of claim 16.

20. The plant of claim 16, wherein the activity of starch synthase II is increased at least 6-fold compared to corresponding genetically unmodified wild-type plant cells.

21. A process for the production of a modified starch comprising extracting starch from the genetically modified plant cell of claim 1, wherein the modified starch has a hot water swelling power of at least 110 g/g.

22. The genetically modified plant cell of claim 1, wherein said foreign nucleic acid molecule encoding a protein having the enzymatic activity of a glucan-water dikinase comprises:
   a) a nucleic acid molecule that encodes a protein comprising the amino acid sequence of SEQ. ID. NO.: 2 or SEQ. ID. NO.: 4;
   b) a nucleic acid molecule that encodes a protein having glucan-water dikinase activity and has an amino acid sequence with at least 95% sequence identity to the amino acid sequence of SEQ. ID. NO.: 2 or SEQ. ID. NO.: 4;
   c) a nucleic acid molecule comprising the nucleic acid sequence of SEQ. ID. NO.: 1 or SEQ. ID. NO.: 3 or a complementary sequence thereof;
   d) a nucleic acid molecule having a sequence identity of at least 95% to the nucleic acid sequences described under c);
   e) a nucleic acid molecule that hybridizes under stringent conditions with at least one strand of the nucleic acid molecules described under a) or c), wherein the stringent conditions are hybridization buffer: 2×SSC, 10×Denhardt solution (Ficoll 400+PEG+BSA; ratio 1:1:1), 0.1% SDS; 5 mM EDTA, 50 mM $Na_2HPO4$, 250 μg/ml of herring sperm DNA, 50 μg/ml of tRNA, or 25 M sodium phosphate buffer pH 7.2; 1 mM EDTA; 7% SDS; hybridization temperature: T=65 to 68° C.; wash buffer: 0.1×SSC; 0.1% SDS; wash temperature: T=65 to 68° C.;
   f) a nucleic acid molecule whose nucleotide sequence differs from the sequence of the nucleic acid molecules mentioned under c) because of the degeneracy of the genetic code; or
   g) fragments, allelic variants, and/or derivatives of the nucleic acid molecules mentioned under a), b), c), d), e) or f), wherein said fragments, allelic variants, and/or derivatives encode a protein having glucan-water dikinase activity.

23. The genetically modified plant cell of claim 22, wherein said foreign nucleic acid molecule encoding a protein having the enzymatic activity of a starch synthase II comprises:
   a) a nucleic acid molecule encoding a protein comprising the amino acid sequence of SEQ. ID. NO.: 6;
   b) a nucleic acid molecule encoding a protein having starch synthase II activity and has an amino acid sequence with at least 95% sequence identity to the amino acid sequence of SEQ. ID. NO.: 6;
   c) a nucleic acid molecule comprising the nucleic acid sequence of SEQ. ID. NO.: 5 or a complementary sequence thereof;
   d) a nucleic acid molecule having a sequence identity of at least 95% to the nucleic acid sequences described under c);
   e) a nucleic acid molecule that hybridizes under stringent conditions with at least one strand of the nucleic acid molecules described under a) or c), wherein the stringent conditions are hybridization buffer: 2×SSC, 10×Denhardt solution (Ficoll 400+PEG+BSA; ratio 1:1:1), 0.1% SDS; 5 mM EDTA, 50 mM Na2HPO4, 250 μg/ml of herring sperm DNA, 50 μg/ml of tRNA, or 25 M sodium phosphate buffer pH 7.2; 1 mM EDTA; 7% SDS; hybridization temperature: T=65 to 68° C.; wash buffer: 0.1×SSC; 0.1% SDS; wash temperature: T=65 to 68° C.;

f) a nucleic acid molecule whose nucleotide sequence differs from the sequence of the nucleic acid molecules mentioned under c) because of the degeneracy of the genetic code; or
g) fragments, allelic variants, and/or derivatives of the nucleic acid molecules mentioned under a), b), c), d), e) or f), wherein said fragments, allelic variants, and/or derivatives encode a protein having starch synthase II activity.

24. A plant comprising the genetically modified plant cell of claim 23.

25. Propagation material of the plant of claim 24.

26. The genetically modified plant cell of claim 1, wherein said foreign nucleic acid molecule encoding a protein having the enzymatic activity of a starch synthase II comprises:
a) a nucleic acid molecule encoding a protein comprising the amino acid sequence of SEQ. ID. NO.: 6;
b) a nucleic acid molecule encoding a protein having starch synthase II activity and has an amino acid sequence with at least 95% sequence identity to the amino acid sequence of SEQ. ID. NO.: 6;
c) a nucleic acid molecule comprising the nucleic acid sequence of SEQ. ID. NO.: 5 or a complementary sequence thereof;
d) a nucleic acid molecule having a sequence identity of at least 95% to the nucleic acid sequences described under c);
e) a nucleic acid molecule that hybridizes under stringent conditions with at least one strand of the nucleic acid molecules described under a) or c), wherein the stringent conditions are hybridization buffer: 2×SSC, 10×Denhardt solution (Ficoll 400+PEG+BSA; ratio 1:1:1), 0.1% SDS; 5 mM EDTA, 50 mM $Na_2HPO_4$, 250 µg/ml of herring sperm DNA, 50 µg/ml of tRNA, or 25 M sodium phosphate buffer pH 7.2; 1 mM EDTA; 7% SDS; hybridization temperature: T=65 to 68° C.; wash buffer: 0.1×SSC; 0.1% SDS; wash temperature: T=65 to 68° C.;
f) a nucleic acid molecule whose nucleotide sequence differs from the sequence of the nucleic acid molecules mentioned under c) because of the degeneracy of the genetic code; or
g) fragments, allelic variants, and/or derivatives of the nucleic acid molecules mentioned under a), b), c), d), e) or f), wherein said fragments, allelic variants, and/or derivatives encode a protein having starch synthase II activity.

27. The genetically modified plant cell of claim 1, wherein said foreign nucleic acid molecule encoding a protein having the enzymatic activity of a glucan-water dikinase comprises:
a nucleic acid molecule that encodes a protein comprising the amino acid sequence of SEQ. ID. NO.: 2 or SEQ. ID. NO.: 4.

28. The genetically modified plant cell of claim 1, wherein said foreign nucleic acid molecule encoding a protein having the enzymatic activity of a glucan-water dikinase comprises:
a nucleic acid molecule that encodes a protein having glucan-water dikinase activity and has an amino acid sequence with at least 95% sequence identity to the amino acid sequence of SEQ. ID. NO.: 2 or SEQ. ID. NO.: 4.

29. The genetically modified plant cell of claim 1, wherein said foreign nucleic acid molecule encoding a protein having the enzymatic activity of a glucan-water dikinase comprises:
a nucleic acid molecule that hybridizes under stringent conditions with at least one strand of (i) a nucleic acid molecule that encodes a protein comprising the amino acid sequence of SEQ. ID. NO.: 2 or SEQ. ID. NO.: 4; or (ii) a nucleic acid molecule comprising the nucleic acid sequence of SEQ. ID. NO.: 1 or SEQ. ID. NO.: 3 or a complementary sequence thereof, wherein the stringent conditions are hybridization buffer: 2×SSC, 10×Denhardt solution (Ficoll 400+PEG+BSA; ratio 1:1:1), 0.1% SDS; 5 mM EDTA, 50 mM $Na_2HPO_4$, 250 µg/ml of herring sperm DNA, 50 µg/ml of tRNA, or 25 M sodium phosphate buffer pH 7.2; 1 mM EDTA; 7% SDS; hybridization temperature: T=65 to 68° C.; wash buffer: 0.1×SSC; 0.1% SDS; wash temperature: T=65 to 68° C.

30. The genetically modified plant cell of claim 1, wherein said foreign nucleic acid molecule encoding a protein having the enzymatic activity of a starch synthase II comprises:
a nucleic acid molecule encoding a protein comprising the amino acid sequence of SEQ. ID. NO.: 6.

31. The genetically modified plant cell of claim 1, wherein said foreign nucleic acid molecule encoding a protein having the enzymatic activity of a starch synthase II comprises:
a nucleic acid molecule encoding a protein having starch synthase II activity and has an amino acid sequence with at least 95% sequence identity to the amino acid sequence of SEQ. ID. NO.: 6.

32. The genetically modified plant cell of claim 1, wherein said foreign nucleic acid molecule encoding a protein having the enzymatic activity of a starch synthase II comprises:
a nucleic acid molecule that hybridizes under stringent conditions with at least one strand of (i) a nucleic acid molecule encoding a protein comprising the amino acid sequence of SEQ. ID. NO.: 6; or (ii) a nucleic acid molecule comprising the nucleic acid sequence of SEQ. ID. NO.: 5 or a complementary sequence thereof, wherein the stringent conditions are hybridization buffer: 2×SSC, 10×Denhardt solution (Ficoll 400+PEG+BSA; ratio 1:1:1), 0.1% SDS; 5 mM EDTA, 50 mM $Na_2HPO_4$, 250 µg/ml of herring sperm DNA, 50 µg/ml of tRNA, or 25 M sodium phosphate buffer pH 7.2; 1 mM EDTA; 7% SDS; hybridization temperature: T=65 to 68° C.; wash buffer: 0.1×SSC; 0.1% SDS; wash temperature: T=65 to 68° C.

33. A process for the production of a genetically modified plant comprising;
a) performing steps i and ii in any desired sequence, individually or simultaneously
(i) introducing a nucleic acid encoding a protein having the activity of a starch synthase II into a plant cell;
(ii) introducing a nucleic acid encoding a protein having the activity of a glucan-water dikinase into a plant cell,
wherein said starch synthase II activity and said glucan-water dikinase is increased in comparison to corresponding wild-type plant cells which are not genetically modified;
b) regenerating a plant from the plant cell of step (a);
c) optionally producing further plants using the plant according to step (b), where plant cells are optionally isolated from plants according to step (b) or (c) and process steps (a) to (c) are repeated until a plant has been produced having an increased activity of a protein having the activity of a starch synthase II and an increased activity of a protein having the activity of a glucan-water dikinase.

* * * * *

UNITED STATES PATENT AND TRADEMARK OFFICE
CERTIFICATE OF CORRECTION

| | | |
|---|---|---|
| PATENT NO. | : 8,304,606 B2 | Page 1 of 1 |
| APPLICATION NO. | : 12/376713 | |
| DATED | : November 6, 2012 | |
| INVENTOR(S) | : Frohberg | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 457 days.

Signed and Sealed this
Thirteenth Day of August, 2013

Teresa Stanek Rea
*Acting Director of the United States Patent and Trademark Office*

SEQUENCE LISTING

```
<160> NUMBER OF SEQ ID NOS: 6

<210> SEQ ID NO 1
<211> LENGTH: 4851
<212> TYPE: DNA
<213> ORGANISM: Solanum tuberosum
<220> FEATURE:
<221> NAME/KEY: transit_peptide
<222> LOCATION: (1)..(77)
<220> FEATURE:
<221> NAME/KEY: CDS
<222> LOCATION: (105)..(4499)
<300> PUBLICATION INFORMATION:
<308> DATABASE ACCESSION NUMBER: EMBL / Y09533
<309> DATABASE ENTRY DATE: 1998-07-30
<313> RELEVANT RESIDUES IN SEQ ID NO: (1)..(4499)

<400> SEQUENCE: 1
catcttcatc gaatttctcg aagcttcttc gctaatttcc tggtttcttc actcaaaatc        60
gacgtttcta gctgaacttg agtgaattaa gccagtggga ggat atg agt aat tcc       116
                                              Met Ser Asn Ser
                                                1 tta ggg aat aac ttg ctg tac cag gga ttc cta acc tca aca gtg ttg       164
Leu Gly Asn Asn Leu Leu Tyr Gln Gly Phe Leu Thr Ser Thr Val Leu
```

```
                 5                    10                   15                   20 gaa cat aaa agt aga atc agt cct cct tgt gtt gga ggc aat tct ttg      212
Glu His Lys Ser Arg Ile Ser Pro Pro Cys Val Gly Gly Asn Ser Leu
             25                  30                  35 ttt caa caa caa gtg atc tcg aaa tca cct tta tca act gag ttt cga      260
Phe Gln Gln Gln Val Ile Ser Lys Ser Pro Leu Ser Thr Glu Phe Arg
    40                  45                  50 ggt aac agg tta aag gtg cag aaa aag aaa ata cct atg gaa aag aag      308
Gly Asn Arg Leu Lys Val Gln Lys Lys Lys Ile Pro Met Glu Lys Lys
        55                  60                  65 cgt gct ttt tct agt tct cct cat gct gta ctt acc act gat acc tct      356
Arg Ala Phe Ser Ser Ser Pro His Ala Val Leu Thr Thr Asp Thr Ser
            70                  75                  80 tct gag cta gca gaa aag ttc agt cta ggg ggg aat att gag cta cag      404
Ser Glu Leu Ala Glu Lys Phe Ser Leu Gly Gly Asn Ile Glu Leu Gln
85                  90                  95                 100 gtt gat gtt agg cct ccc act tca ggt gat gtg tcc ttt gtg gat ttt      452
Val Asp Val Arg Pro Pro Thr Ser Gly Asp Val Ser Phe Val Asp Phe
                105                 110                 115 caa gta aca aat ggt agt gat aaa ctg ttt ttg cac tgg ggg gca gta      500
Gln Val Thr Asn Gly Ser Asp Lys Leu Phe Leu His Trp Gly Ala Val
            120                 125                 130 aaa ttc ggg aaa gaa aca tgg tct ctt ccg aat gat cgt cca gat ggg      548
Lys Phe Gly Lys Glu Thr Trp Ser Leu Pro Asn Asp Arg Pro Asp Gly
        135                 140                 145 acc aaa gtg tac aag aac aaa gca ctt aga act cca ttt gtt aaa tct      596
Thr Lys Val Tyr Lys Asn Lys Ala Leu Arg Thr Pro Phe Val Lys Ser
    150                 155                 160 ggc tct aac tcc atc ctg aga ctg gag ata cga gac act gct atc gaa      644
Gly Ser Asn Ser Ile Leu Arg Leu Glu Ile Arg Asp Thr Ala Ile Glu
165                 170                 175                 180 gct att gag ttt ctc ata tac gat gaa gcc cac gat aaa tgg ata aag      692
Ala Ile Glu Phe Leu Ile Tyr Asp Glu Ala His Asp Lys Trp Ile Lys
                185                 190                 195 aat aat ggt ggt aat ttt cgt gtc aaa ttg tca aga aaa gag ata cga      740
Asn Asn Gly Gly Asn Phe Arg Val Lys Leu Ser Arg Lys Glu Ile Arg
            200                 205                 210 ggc cca gat gtt tct gtt cct gag gag ctt gta cag atc caa tca tat      788
Gly Pro Asp Val Ser Val Pro Glu Glu Leu Val Gln Ile Gln Ser Tyr
        215                 220                 225 ttg agg tgg gag agg aag gga aaa cag aat tac ccc cct gag aaa gag      836
Leu Arg Trp Glu Arg Lys Gly Lys Gln Asn Tyr Pro Pro Glu Lys Glu
    230                 235                 240 aag gag gaa tat gag gct gct cga act gtg cta cag gag gaa ata gct      884
Lys Glu Glu Tyr Glu Ala Ala Arg Thr Val Leu Gln Glu Glu Ile Ala
245                 250                 255                 260 cgt ggt gct tcc ata cag gac att cga gca agg cta aca aaa act aat      932
Arg Gly Ala Ser Ile Gln Asp Ile Arg Ala Arg Leu Thr Lys Thr Asn
                265                 270                 275 gat aaa agt caa agc aaa gaa gag cct ctt cat gta aca aag agt gat      980
Asp Lys Ser Gln Ser Lys Glu Glu Pro Leu His Val Thr Lys Ser Asp
            280                 285                 290 ata cct gat gac ctt gcc caa gca caa gct tac att agg tgg gag aaa     1028
Ile Pro Asp Asp Leu Ala Gln Ala Gln Ala Tyr Ile Arg Trp Glu Lys
        295                 300                 305 gca gga aag ccg aac tat cct cca gaa aag caa att gaa gaa ctc gaa     1076
Ala Gly Lys Pro Asn Tyr Pro Pro Glu Lys Gln Ile Glu Glu Leu Glu
    310                 315                 320 gaa gca aga aga gaa ttg caa ctt gag ctt gag aaa ggc att acc ctt     1124
Glu Ala Arg Arg Glu Leu Gln Leu Glu Leu Glu Lys Gly Ile Thr Leu
```

```
                     325                 330                 335                 340
gat gag ttg cgg aaa acg att aca aaa ggg gag ata aaa act aag gtg          1172
Asp Glu Leu Arg Lys Thr Ile Thr Lys Gly Glu Ile Lys Thr Lys Val
                345                 350                 355 gaa aag cac ctg aaa aga agt tct ttt gcc gtt gaa aga atc caa aga          1220
Glu Lys His Leu Lys Arg Ser Ser Phe Ala Val Glu Arg Ile Gln Arg
                360                 365                 370 aag aag aga gac ttt ggg cat ctt att aat aag tat act tcc agt cct          1268
Lys Lys Arg Asp Phe Gly His Leu Ile Asn Lys Tyr Thr Ser Ser Pro
                375                 380                 385 gca gta caa gta caa aag gtc ttg gaa gaa cca cca gcc tta tct aaa          1316
Ala Val Gln Val Gln Lys Val Leu Glu Glu Pro Pro Ala Leu Ser Lys
                390                 395                 400 att aag ctg tat gcc aag gag aag gag gag cag att gat gat ccg atc          1364
Ile Lys Leu Tyr Ala Lys Glu Lys Glu Glu Gln Ile Asp Asp Pro Ile
405                 410                 415                 420 cta aat aaa aag atc ttt aag gtc gat gat ggg gag cta ctg gta ctg          1412
Leu Asn Lys Lys Ile Phe Lys Val Asp Asp Gly Glu Leu Leu Val Leu
                425                 430                 435 gta gca aag tcc tct ggg aag aca aaa gta cat cta gct aca gat ctg          1460
Val Ala Lys Ser Ser Gly Lys Thr Lys Val His Leu Ala Thr Asp Leu
                440                 445                 450 aat cag cca att act ctt cac tgg gca tta tcc aaa agt cct gga gag          1508
Asn Gln Pro Ile Thr Leu His Trp Ala Leu Ser Lys Ser Pro Gly Glu
                455                 460                 465 tgg atg gta cca cct tca agc ata ttg cct cct ggg tca att att tta          1556
Trp Met Val Pro Pro Ser Ser Ile Leu Pro Pro Gly Ser Ile Ile Leu
                470                 475                 480 gac aag gct gcc gaa aca cct ttt tca gcc agt tct tct gat ggt cta          1604
Asp Lys Ala Ala Glu Thr Pro Phe Ser Ala Ser Ser Ser Asp Gly Leu
485                 490                 495                 500 act tct aag gta caa tct ttg gat ata gta att gaa gat ggc aat ttt          1652
Thr Ser Lys Val Gln Ser Leu Asp Ile Val Ile Glu Asp Gly Asn Phe
                505                 510                 515 gtg ggg atg cca ttt gtt ctt ttg tct ggt gaa aaa tgg att aag aac          1700
Val Gly Met Pro Phe Val Leu Leu Ser Gly Glu Lys Trp Ile Lys Asn
                520                 525                 530 caa ggg tcg gat ttc tat gtt ggc ttc agt gct gca tcc aaa tta gca          1748
Gln Gly Ser Asp Phe Tyr Val Gly Phe Ser Ala Ala Ser Lys Leu Ala
                535                 540                 545 ctc aag gct gct ggg gat ggc agt gga act gca aag tct tta ctg gat          1796
Leu Lys Ala Ala Gly Asp Gly Ser Gly Thr Ala Lys Ser Leu Leu Asp
                550                 555                 560 aaa ata gca gat atg gaa agt gag gct cag aag tca ttt atg cac cgg          1844
Lys Ile Ala Asp Met Glu Ser Glu Ala Gln Lys Ser Phe Met His Arg
565                 570                 575                 580 ttt aat att gca gct gac ttg ata gaa gat gcc act agt gct ggt gaa          1892
Phe Asn Ile Ala Ala Asp Leu Ile Glu Asp Ala Thr Ser Ala Gly Glu
                585                 590                 595 ctt ggt ttt gct gga att ctt gta tgg atg agg ttc atg gct aca agg          1940
Leu Gly Phe Ala Gly Ile Leu Val Trp Met Arg Phe Met Ala Thr Arg
                600                 605                 610 caa ctg ata tgg aac aaa aac tat aac gta aaa cca cgt gaa ata agc          1988
Gln Leu Ile Trp Asn Lys Asn Tyr Asn Val Lys Pro Arg Glu Ile Ser
                615                 620                 625 aag gct cag gac aga ctt aca gac ttg ttg cag aat gct ttc acc agt          2036
Lys Ala Gln Asp Arg Leu Thr Asp Leu Leu Gln Asn Ala Phe Thr Ser
                630                 635                 640 cac cct cag tac cgt gaa att ttg cgg atg att atg tca act gtt gga          2084
His Pro Gln Tyr Arg Glu Ile Leu Arg Met Ile Met Ser Thr Val Gly
```

-continued

```
            645                 650                 655                 660
cgt gga ggt gaa ggg gat gta gga cag cga att agg gat gaa att ttg         2132
Arg Gly Gly Glu Gly Asp Val Gly Gln Arg Ile Arg Asp Glu Ile Leu
                    665                 670                 675 gtc atc cag agg aac aat gac tgc aag ggt ggt atg atg caa gaa tgg         2180
Val Ile Gln Arg Asn Asn Asp Cys Lys Gly Gly Met Met Gln Glu Trp
                680                 685                 690 cat cag aaa ttg cat aat aat act agt cct gat gat gtt gtg atc tgt         2228
His Gln Lys Leu His Asn Asn Thr Ser Pro Asp Asp Val Val Ile Cys
            695                 700                 705 cag gca tta att gac tac atc aag agt gat ttt gat ctt ggt gtt tat         2276
Gln Ala Leu Ile Asp Tyr Ile Lys Ser Asp Phe Asp Leu Gly Val Tyr
        710                 715                 720 tgg aaa acc ctg aat gag aac gga ata aca aaa gag cgt ctt ttg agt         2324
Trp Lys Thr Leu Asn Glu Asn Gly Ile Thr Lys Glu Arg Leu Leu Ser
725                 730                 735                 740 tat gac cgt gct atc cat tct gaa cca aat ttt aga gga gat caa aag         2372
Tyr Asp Arg Ala Ile His Ser Glu Pro Asn Phe Arg Gly Asp Gln Lys
                745                 750                 755 ggt ggt ctt ttg cgt gat tta ggt cac tat atg aga aca ttg aag gca         2420
Gly Gly Leu Leu Arg Asp Leu Gly His Tyr Met Arg Thr Leu Lys Ala
                760                 765                 770 gtt cat tca ggt gca gat ctt gag tct gct att gca aac tgc atg ggc         2468
Val His Ser Gly Ala Asp Leu Glu Ser Ala Ile Ala Asn Cys Met Gly
            775                 780                 785 tac aaa act gag gga gaa ggc ttt atg gtt gga gtc cag ata aat cct         2516
Tyr Lys Thr Glu Gly Glu Gly Phe Met Val Gly Val Gln Ile Asn Pro
        790                 795                 800 gta tca ggc ttg cca tct ggc ttt cag gac ctc ctc cat ttt gtc tta         2564
Val Ser Gly Leu Pro Ser Gly Phe Gln Asp Leu Leu His Phe Val Leu
805                 810                 815                 820 gac cat gtg gaa gat aaa aat gtg gaa act ctt ctt gag aga ttg cta         2612
Asp His Val Glu Asp Lys Asn Val Glu Thr Leu Leu Glu Arg Leu Leu
                825                 830                 835 gag gct cgt gag gag ctt agg ccc ttg ctt ctc aaa cca aac aac cgt         2660
Glu Ala Arg Glu Glu Leu Arg Pro Leu Leu Leu Lys Pro Asn Asn Arg
                840                 845                 850 cta aag gat ctg ctg ttt ttg gac ata gca ctt gat tct aca gtt aga         2708
Leu Lys Asp Leu Leu Phe Leu Asp Ile Ala Leu Asp Ser Thr Val Arg
            855                 860                 865 aca gca gta gaa agg gga tat gaa gaa ttg aac aac gct aat cct gag         2756
Thr Ala Val Glu Arg Gly Tyr Glu Glu Leu Asn Asn Ala Asn Pro Glu
        870                 875                 880 aaa atc atg tac ttc atc tcc ctc gtt ctt gaa aat ctc gca ctc tct         2804
Lys Ile Met Tyr Phe Ile Ser Leu Val Leu Glu Asn Leu Ala Leu Ser
885                 890                 895                 900 gtg gac gat aat gaa gat ctt gtt tat tgc ttg aag gga tgg aat caa         2852
Val Asp Asp Asn Glu Asp Leu Val Tyr Cys Leu Lys Gly Trp Asn Gln
                905                 910                 915 gct ctt tca atg tcc aat ggt ggg gac aac cat tgg gct tta ttt gca         2900
Ala Leu Ser Met Ser Asn Gly Gly Asp Asn His Trp Ala Leu Phe Ala
                920                 925                 930 aaa gct gtg ctt gac aga acc cgt ctt gca ctt gca agc aag gca gag         2948
Lys Ala Val Leu Asp Arg Thr Arg Leu Ala Leu Ala Ser Lys Ala Glu
            935                 940                 945 tgg tac cat cac tta ttg cag cca tct gcc gaa tat cta gga tca ata         2996
Trp Tyr His His Leu Leu Gln Pro Ser Ala Glu Tyr Leu Gly Ser Ile
        950                 955                 960 ctt ggg gtg gac caa tgg gct ttg aac ata ttt act gaa gaa att ata         3044
Leu Gly Val Asp Gln Trp Ala Leu Asn Ile Phe Thr Glu Glu Ile Ile
```

-continued

```
                965                 970                 975                 980
cgt gct gga tca gca gct tca tta tcc tct ctt ctt aat aga ctc gat      3092
Arg Ala Gly Ser Ala Ala Ser Leu Ser Ser Leu Leu Asn Arg Leu Asp
                    985                 990                 995 ccc gtg ctt cgg aaa act gca aat cta gga agt tgg cag att atc          3137
Pro Val Leu Arg Lys Thr Ala Asn Leu Gly Ser Trp Gln Ile Ile
        1000                1005                1010 agt cca gtt gaa gcc gtt gga tat gtt gtc gtt gtg gat gag ttg          3182
Ser Pro Val Glu Ala Val Gly Tyr Val Val Val Val Asp Glu Leu
        1015                1020                1025 ctt tca gtt cag aat gaa atc tac gag aag ccc acg atc tta gta          3227
Leu Ser Val Gln Asn Glu Ile Tyr Glu Lys Pro Thr Ile Leu Val
        1030                1035                1040 gca aaa tct gtt aaa gga gag gag gaa att cct gat ggt gct gtt          3272
Ala Lys Ser Val Lys Gly Glu Glu Glu Ile Pro Asp Gly Ala Val
        1045                1050                1055 gcc ctg ata aca cca gac atg cca gat gtt ctt tca cat gtt tct          3317
Ala Leu Ile Thr Pro Asp Met Pro Asp Val Leu Ser His Val Ser
        1060                1065                1070 gtt cga gct aga aat ggg aag gtt tgc ttt gct aca tgc ttt gat          3362
Val Arg Ala Arg Asn Gly Lys Val Cys Phe Ala Thr Cys Phe Asp
        1075                1080                1085 ccc aat ata ttg gct gac ctc caa gca aag gaa gga agg att ttg          3407
Pro Asn Ile Leu Ala Asp Leu Gln Ala Lys Glu Gly Arg Ile Leu
        1090                1095                1100 ctc tta aag cct aca cct tca gac ata atc tat agt gag gtg aat          3452
Leu Leu Lys Pro Thr Pro Ser Asp Ile Ile Tyr Ser Glu Val Asn
        1105                1110                1115 gag att gag ctc caa agt tca agt aac ttg gta gaa gct gaa act          3497
Glu Ile Glu Leu Gln Ser Ser Ser Asn Leu Val Glu Ala Glu Thr
        1120                1125                1130 tca gca aca ctt aga ttg gtg aaa aag caa ttt ggt ggt tgt tac          3542
Ser Ala Thr Leu Arg Leu Val Lys Lys Gln Phe Gly Gly Cys Tyr
        1135                1140                1145 gca ata tca gca gat gaa ttc aca agt gaa atg gtt gga gct aaa          3587
Ala Ile Ser Ala Asp Glu Phe Thr Ser Glu Met Val Gly Ala Lys
        1150                1155                1160 tca cgt aat att gca tat ctg aaa gga aaa gtg cct tcc tcg gtg          3632
Ser Arg Asn Ile Ala Tyr Leu Lys Gly Lys Val Pro Ser Ser Val
        1165                1170                1175 gga att cct acg tca gta gct ctt cca ttt gga gtc ttt gag aaa          3677
Gly Ile Pro Thr Ser Val Ala Leu Pro Phe Gly Val Phe Glu Lys
        1180                1185                1190 gta ctt tca gac gac ata aat cag gga gtg gca aaa gag ttg caa          3722
Val Leu Ser Asp Asp Ile Asn Gln Gly Val Ala Lys Glu Leu Gln
        1195                1200                1205 att ctg atg aaa aaa cta tct gaa gga gac ttc agc gct ctt ggt          3767
Ile Leu Met Lys Lys Leu Ser Glu Gly Asp Phe Ser Ala Leu Gly
        1210                1215                1220 gaa att cgc aca acg gtt tta gat ctt tca gca cca gct caa ttg          3812
Glu Ile Arg Thr Thr Val Leu Asp Leu Ser Ala Pro Ala Gln Leu
        1225                1230                1235 gtc aaa gag ctg aag gag aag atg cag ggt tct ggc atg cct tgg          3857
Val Lys Glu Leu Lys Glu Lys Met Gln Gly Ser Gly Met Pro Trp
        1240                1245                1250 cct ggt gat gaa ggt cca aag cgg tgg gaa caa gca tgg atg gcc          3902
Pro Gly Asp Glu Gly Pro Lys Arg Trp Glu Gln Ala Trp Met Ala
        1255                1260                1265 ata aaa aag gtg tgg gct tca aaa tgg aat gag aga gca tac ttc          3947
Ile Lys Lys Val Trp Ala Ser Lys Trp Asn Glu Arg Ala Tyr Phe
```

-continued

```
                        1270                        1275                        1280
agc  aca  agg  aag  gtg  aaa  ctg  gat  cat  gac  tat  ctg  tgc  atg  gct            3992
Ser  Thr  Arg  Lys  Val  Lys  Leu  Asp  His  Asp  Tyr  Leu  Cys  Met  Ala
               1285                        1290                        1295 gtc  ctt  gtt  caa  gaa  ata  ata  aat  gct  gat  tat  gca  ttt  gtc  att            4037
Val  Leu  Val  Gln  Glu  Ile  Ile  Asn  Ala  Asp  Tyr  Ala  Phe  Val  Ile
               1300                        1305                        1310 cac  aca  acc  aac  cca  tct  tcc  gga  gac  gac  tca  gaa  ata  tat  gcc            4082
His  Thr  Thr  Asn  Pro  Ser  Ser  Gly  Asp  Asp  Ser  Glu  Ile  Tyr  Ala
               1315                        1320                        1325 gag  gtg  gtc  agg  ggc  ctt  ggg  gaa  aca  ctt  gtt  gga  gct  tat  cca            4127
Glu  Val  Val  Arg  Gly  Leu  Gly  Glu  Thr  Leu  Val  Gly  Ala  Tyr  Pro
               1330                        1335                        1340 gga  cgt  gct  ttg  agt  ttt  atc  tgc  aag  aaa  aag  gat  ctc  aac  tct            4172
Gly  Arg  Ala  Leu  Ser  Phe  Ile  Cys  Lys  Lys  Lys  Asp  Leu  Asn  Ser
               1345                        1350                        1355 cct  caa  gtg  tta  ggt  tac  cca  agc  aaa  ccg  atc  ggc  ctt  ttc  ata            4217
Pro  Gln  Val  Leu  Gly  Tyr  Pro  Ser  Lys  Pro  Ile  Gly  Leu  Phe  Ile
               1360                        1365                        1370 aaa  aga  tct  atc  atc  ttc  cga  tct  gat  tcc  aat  ggg  gaa  gat  ttg            4262
Lys  Arg  Ser  Ile  Ile  Phe  Arg  Ser  Asp  Ser  Asn  Gly  Glu  Asp  Leu
               1375                        1380                        1385 gaa  ggt  tat  gcc  ggt  gct  ggc  ctc  tac  gac  agt  gta  cca  atg  gat            4307
Glu  Gly  Tyr  Ala  Gly  Ala  Gly  Leu  Tyr  Asp  Ser  Val  Pro  Met  Asp
               1390                        1395                        1400 gag  gag  gaa  aaa  gtt  gta  att  gat  tac  tct  tcc  gac  cca  ttg  ata            4352
Glu  Glu  Glu  Lys  Val  Val  Ile  Asp  Tyr  Ser  Ser  Asp  Pro  Leu  Ile
               1405                        1410                        1415 act  gat  ggt  aac  ttc  cgc  cag  aca  atc  ctg  tcc  aac  att  gct  cgt            4397
Thr  Asp  Gly  Asn  Phe  Arg  Gln  Thr  Ile  Leu  Ser  Asn  Ile  Ala  Arg
               1420                        1425                        1430 gct  gga  cat  gct  atc  gag  gag  cta  tat  ggc  tct  cct  caa  gac  att            4442
Ala  Gly  His  Ala  Ile  Glu  Glu  Leu  Tyr  Gly  Ser  Pro  Gln  Asp  Ile
               1435                        1440                        1445 gag  ggt  gta  gtg  agg  gat  gga  aag  att  tat  gtc  gtt  cag  aca  aga            4487
Glu  Gly  Val  Val  Arg  Asp  Gly  Lys  Ile  Tyr  Val  Val  Gln  Thr  Arg
               1450                        1455                        1460 cca  cag  atg  tga  ttatattctc gttgtatgtt gttcagagaa gaccacagat                      4539
Pro  Gln  Met gtgatcatat tctcattgta tcagatctgt gaccacttac ctgataccct ccatgaagtt                     4599
acctgtatga ttatacgtga tccaaagcca tcacatcatg ttcaccttca gctattggag                     4659
gagaagtgag aagtaggaat tgcaatatga ggaataataa gaaaaacttt gtaaaagcta                     4719
aattagctgg gtatgatata gggagaaatg tgtaaacatt gtactatata tagtatatac                     4779
acacgcatta tgtattgcat tatgcactga ataatatcgc agcatcaaag aagaaatcct                     4839
ttgggtggtt tc                                                                        4851
```

<210> SEQ ID NO 2
<211> LENGTH: 1464
<212> TYPE: PRT
<213> ORGANISM: Solanum tuberosum

<400> SEQUENCE: 2

```
Met Ser Asn Ser Leu Gly Asn Asn Leu Leu Tyr Gln Gly Phe Leu Thr
1               5                   10                  15

Ser Thr Val Leu Glu His Lys Ser Arg Ile Ser Pro Pro Cys Val Gly
            20                  25                  30

Gly Asn Ser Leu Phe Gln Gln Gln Val Ile Ser Lys Ser Pro Leu Ser
```

-continued

```
                35                  40                  45
Thr Glu Phe Arg Gly Asn Arg Leu Lys Val Gln Lys Lys Ile Pro
 50                  55                  60
Met Glu Lys Lys Arg Ala Phe Ser Ser Pro His Ala Val Leu Thr
 65                  70                  75                  80
Thr Asp Thr Ser Ser Glu Leu Ala Glu Lys Phe Ser Leu Gly Gly Asn
                     85                  90                  95
Ile Glu Leu Gln Val Asp Val Arg Pro Thr Ser Gly Asp Val Ser
                100                 105                 110
Phe Val Asp Phe Gln Val Thr Asn Gly Ser Asp Lys Leu Phe Leu His
                115                 120                 125
Trp Gly Ala Val Lys Phe Gly Lys Glu Thr Trp Ser Leu Pro Asn Asp
130                 135                 140
Arg Pro Asp Gly Thr Lys Val Tyr Lys Asn Lys Ala Leu Arg Thr Pro
145                 150                 155                 160
Phe Val Lys Ser Gly Ser Asn Ser Ile Leu Arg Leu Glu Ile Arg Asp
                165                 170                 175
Thr Ala Ile Glu Ala Ile Glu Phe Leu Ile Tyr Asp Glu Ala His Asp
                180                 185                 190
Lys Trp Ile Lys Asn Asn Gly Gly Asn Phe Arg Val Lys Leu Ser Arg
                195                 200                 205
Lys Glu Ile Arg Gly Pro Asp Val Ser Val Pro Glu Leu Val Gln
                210                 215                 220
Ile Gln Ser Tyr Leu Arg Trp Glu Arg Lys Gly Lys Gln Asn Tyr Pro
225                 230                 235                 240
Pro Glu Lys Glu Lys Glu Glu Tyr Glu Ala Ala Arg Thr Val Leu Gln
                245                 250                 255
Glu Glu Ile Ala Arg Gly Ala Ser Ile Gln Asp Ile Arg Ala Arg Leu
                260                 265                 270
Thr Lys Thr Asn Asp Lys Ser Gln Ser Lys Glu Pro Leu His Val
                275                 280                 285
Thr Lys Ser Asp Ile Pro Asp Asp Leu Ala Gln Ala Gln Ala Tyr Ile
290                 295                 300
Arg Trp Glu Lys Ala Gly Lys Pro Asn Tyr Pro Pro Glu Lys Gln Ile
305                 310                 315                 320
Glu Glu Leu Glu Glu Ala Arg Arg Glu Leu Gln Leu Glu Leu Glu Lys
                325                 330                 335
Gly Ile Thr Leu Asp Glu Leu Arg Lys Thr Ile Thr Lys Gly Glu Ile
                340                 345                 350
Lys Thr Lys Val Glu Lys His Leu Lys Arg Ser Ser Phe Ala Val Glu
                355                 360                 365
Arg Ile Gln Arg Lys Lys Arg Asp Phe Gly His Leu Ile Asn Lys Tyr
370                 375                 380
Thr Ser Ser Pro Ala Val Gln Val Gln Lys Val Leu Glu Glu Pro Pro
385                 390                 395                 400
Ala Leu Ser Lys Ile Lys Leu Tyr Ala Lys Glu Lys Glu Gln Ile
                405                 410                 415
Asp Asp Pro Ile Leu Asn Lys Lys Ile Phe Lys Val Asp Asp Gly Glu
                420                 425                 430
Leu Leu Val Leu Val Ala Lys Ser Gly Lys Thr Lys Val His Leu
                435                 440                 445
Ala Thr Asp Leu Asn Gln Pro Ile Thr Leu His Trp Ala Leu Ser Lys
450                 455                 460
```

-continued

Ser Pro Gly Glu Trp Met Val Pro Ser Ser Ile Leu Pro Pro Gly
465                 470                 475                 480

Ser Ile Ile Leu Asp Lys Ala Ala Glu Thr Pro Phe Ser Ala Ser Ser
            485                 490                 495

Ser Asp Gly Leu Thr Ser Lys Val Gln Ser Leu Asp Ile Val Ile Glu
            500                 505                 510

Asp Gly Asn Phe Val Gly Met Pro Phe Val Leu Leu Ser Gly Glu Lys
            515                 520                 525

Trp Ile Lys Asn Gln Gly Ser Asp Phe Tyr Val Gly Phe Ser Ala Ala
530                 535                 540

Ser Lys Leu Ala Leu Lys Ala Ala Gly Asp Gly Ser Gly Thr Ala Lys
545                 550                 555                 560

Ser Leu Leu Asp Lys Ile Ala Asp Met Glu Ser Glu Ala Gln Lys Ser
            565                 570                 575

Phe Met His Arg Phe Asn Ile Ala Ala Asp Leu Ile Glu Asp Ala Thr
            580                 585                 590

Ser Ala Gly Glu Leu Gly Phe Ala Gly Ile Leu Val Trp Met Arg Phe
            595                 600                 605

Met Ala Thr Arg Gln Leu Ile Trp Asn Lys Asn Tyr Asn Val Lys Pro
610                 615                 620

Arg Glu Ile Ser Lys Ala Gln Asp Arg Leu Thr Asp Leu Leu Gln Asn
625                 630                 635                 640

Ala Phe Thr Ser His Pro Gln Tyr Arg Glu Ile Leu Arg Met Ile Met
            645                 650                 655

Ser Thr Val Gly Arg Gly Gly Glu Gly Asp Val Gly Gln Arg Ile Arg
            660                 665                 670

Asp Glu Ile Leu Val Ile Gln Arg Asn Asn Asp Cys Lys Gly Gly Met
            675                 680                 685

Met Gln Glu Trp His Gln Lys Leu His Asn Asn Thr Ser Pro Asp Asp
            690                 695                 700

Val Val Ile Cys Gln Ala Leu Ile Asp Tyr Ile Lys Ser Asp Phe Asp
705                 710                 715                 720

Leu Gly Val Tyr Trp Lys Thr Leu Asn Glu Asn Gly Ile Thr Lys Glu
            725                 730                 735

Arg Leu Leu Ser Tyr Asp Arg Ala Ile His Ser Glu Pro Asn Phe Arg
            740                 745                 750

Gly Asp Gln Lys Gly Gly Leu Leu Arg Asp Leu Gly His Tyr Met Arg
            755                 760                 765

Thr Leu Lys Ala Val His Ser Gly Ala Asp Leu Glu Ser Ala Ile Ala
            770                 775                 780

Asn Cys Met Gly Tyr Lys Thr Glu Gly Glu Gly Phe Met Val Gly Val
785                 790                 795                 800

Gln Ile Asn Pro Val Ser Gly Leu Pro Ser Gly Phe Gln Asp Leu Leu
            805                 810                 815

His Phe Val Leu Asp His Val Glu Asp Lys Asn Val Glu Thr Leu Leu
            820                 825                 830

Glu Arg Leu Leu Glu Ala Arg Glu Glu Leu Arg Pro Leu Leu Leu Lys
            835                 840                 845

Pro Asn Asn Arg Leu Lys Asp Leu Leu Phe Leu Asp Ile Ala Leu Asp
850                 855                 860

Ser Thr Val Arg Thr Ala Val Glu Arg Gly Tyr Glu Glu Leu Asn Asn
865                 870                 875                 880

Ala Asn Pro Glu Lys Ile Met Tyr Phe Ile Ser Leu Val Leu Glu Asn
            885                 890                 895

```
Leu Ala Leu Ser Val Asp Asp Asn Glu Asp Leu Val Tyr Cys Leu Lys
            900                 905                 910
Gly Trp Asn Gln Ala Leu Ser Met Ser Asn Gly Gly Asp Asn His Trp
        915                 920                 925
Ala Leu Phe Ala Lys Ala Val Leu Asp Arg Thr Arg Leu Ala Leu Ala
    930                 935                 940
Ser Lys Ala Glu Trp Tyr His His Leu Gln Pro Ser Ala Glu Tyr
945                 950                 955                 960
Leu Gly Ser Ile Leu Gly Val Asp Gln Trp Ala Leu Asn Ile Phe Thr
                965                 970                 975
Glu Glu Ile Ile Arg Ala Gly Ser Ala Ala Ser Leu Ser Ser Leu Leu
            980                 985                 990
Asn Arg Leu Asp Pro Val Leu Arg Lys Thr Ala Asn Leu Gly Ser Trp
        995                 1000                1005
Gln Ile Ile Ser Pro Val Glu Ala Val Gly Tyr Val Val Val Val
    1010                1015                1020
Asp Glu Leu Leu Ser Val Gln Asn Glu Ile Tyr Glu Lys Pro Thr
    1025                1030                1035
Ile Leu Val Ala Lys Ser Val Lys Gly Glu Glu Glu Ile Pro Asp
    1040                1045                1050
Gly Ala Val Ala Leu Ile Thr Pro Asp Met Pro Asp Val Leu Ser
    1055                1060                1065
His Val Ser Val Arg Ala Arg Asn Gly Lys Val Cys Phe Ala Thr
    1070                1075                1080
Cys Phe Asp Pro Asn Ile Leu Ala Asp Leu Gln Ala Lys Glu Gly
    1085                1090                1095
Arg Ile Leu Leu Leu Lys Pro Thr Pro Ser Asp Ile Ile Tyr Ser
    1100                1105                1110
Glu Val Asn Glu Ile Glu Leu Gln Ser Ser Ser Asn Leu Val Glu
    1115                1120                1125
Ala Glu Thr Ser Ala Thr Leu Arg Leu Val Lys Lys Gln Phe Gly
    1130                1135                1140
Gly Cys Tyr Ala Ile Ser Ala Asp Glu Phe Thr Ser Glu Met Val
    1145                1150                1155
Gly Ala Lys Ser Arg Asn Ile Ala Tyr Leu Lys Gly Lys Val Pro
    1160                1165                1170
Ser Ser Val Gly Ile Pro Thr Ser Val Ala Leu Pro Phe Gly Val
    1175                1180                1185
Phe Glu Lys Val Leu Ser Asp Asp Ile Asn Gln Gly Val Ala Lys
    1190                1195                1200
Glu Leu Gln Ile Leu Met Lys Lys Leu Ser Glu Gly Asp Phe Ser
    1205                1210                1215
Ala Leu Gly Glu Ile Arg Thr Thr Val Leu Asp Leu Ser Ala Pro
    1220                1225                1230
Ala Gln Leu Val Lys Glu Leu Lys Glu Lys Met Gln Gly Ser Gly
    1235                1240                1245
Met Pro Trp Pro Gly Asp Glu Gly Pro Lys Arg Trp Glu Gln Ala
    1250                1255                1260
Trp Met Ala Ile Lys Lys Val Trp Ala Ser Lys Trp Asn Glu Arg
    1265                1270                1275
Ala Tyr Phe Ser Thr Arg Lys Val Lys Leu Asp His Asp Tyr Leu
    1280                1285                1290
Cys Met Ala Val Leu Val Gln Glu Ile Ile Asn Ala Asp Tyr Ala
```

```
                1295                1300                1305

Phe Val Ile His Thr Thr Asn Pro Ser Ser Gly Asp Asp Ser Glu
    1310                1315                1320

Ile Tyr Ala Glu Val Val Arg Gly Leu Gly Glu Thr Leu Val Gly
    1325                1330                1335

Ala Tyr Pro Gly Arg Ala Leu Ser Phe Ile Cys Lys Lys Lys Asp
    1340                1345                1350

Leu Asn Ser Pro Gln Val Leu Gly Tyr Pro Ser Lys Pro Ile Gly
    1355                1360                1365

Leu Phe Ile Lys Arg Ser Ile Ile Phe Arg Ser Asp Ser Asn Gly
    1370                1375                1380

Glu Asp Leu Glu Gly Tyr Ala Gly Ala Gly Leu Tyr Asp Ser Val
    1385                1390                1395

Pro Met Asp Glu Glu Glu Lys Val Val Ile Asp Tyr Ser Ser Asp
    1400                1405                1410

Pro Leu Ile Thr Asp Gly Asn Phe Arg Gln Thr Ile Leu Ser Asn
    1415                1420                1425

Ile Ala Arg Ala Gly His Ala Ile Glu Glu Leu Tyr Gly Ser Pro
    1430                1435                1440

Gln Asp Ile Glu Gly Val Val Arg Asp Gly Lys Ile Tyr Val Val
    1445                1450                1455

Gln Thr Arg Pro Gln Met
    1460

<210> SEQ ID NO 3
<211> LENGTH: 4443
<212> TYPE: DNA
<213> ORGANISM: Curcuma longa
<220> FEATURE:
<221> NAME/KEY: CDS
<222> LOCATION: (1)..(4443)

<400> SEQUENCE: 3 atg aac aat tgt gtt gga cat acc tta cct cag caa gct ctg ttt cgg     48
Met Asn Asn Cys Val Gly His Thr Leu Pro Gln Gln Ala Leu Phe Arg
1               5                   10                  15 cct tct gtt gta gaa cgc cat aat aca gct tgc caa cgt tct tct gga     96
Pro Ser Val Val Glu Arg His Asn Thr Ala Cys Gln Arg Ser Ser Gly
            20                  25                  30 aac att ttg tgc act gtt cca tca gca tca aag gca gaa gat gtg cca    144
Asn Ile Leu Cys Thr Val Pro Ser Ala Ser Lys Ala Glu Asp Val Pro
        35                  40                  45 tct ctt aaa cct ttc ctt tca agt aga ttc ctg ggg aag act ccc tat    192
Ser Leu Lys Pro Phe Leu Ser Ser Arg Phe Leu Gly Lys Thr Pro Tyr
    50                  55                  60 gca gga aaa gga aac cca tta aag aaa aat tta aga aca gtt acc atg    240
Ala Gly Lys Gly Asn Pro Leu Lys Lys Asn Leu Arg Thr Val Thr Met
65                  70                  75                  80 agc cct caa gct tta ttg gca gca gat cct gct tca gag ctt gct aga    288
Ser Pro Gln Ala Leu Leu Ala Ala Asp Pro Ala Ser Glu Leu Ala Arg
                85                  90                  95 aaa ttc aag ctg gac acc aat tcc gaa ttg gag gtt act att tgt aag    336
Lys Phe Lys Leu Asp Thr Asn Ser Glu Leu Glu Val Thr Ile Cys Lys
            100                 105                 110 ccc aca tct gag tct cct atg caa att gat ttt caa gta acc aat gtc    384
Pro Thr Ser Glu Ser Pro Met Gln Ile Asp Phe Gln Val Thr Asn Val
        115                 120                 125 agt ggt tcc ttg gtg ctt cat tgg ggt gta att ctc caa aca aga aga    432
Ser Gly Ser Leu Val Leu His Trp Gly Val Ile Leu Gln Thr Arg Arg
```

-continued

```
         130                 135                 140
gaa tgg tct ctt cct tct cat tat cct gaa gga aca aaa gta tac aaa      480
Glu Trp Ser Leu Pro Ser His Tyr Pro Glu Gly Thr Lys Val Tyr Lys
145                 150                 155                 160 aat caa gct ctc aga act cct ttt act aaa gtt ggc tcg act tgt tca      528
Asn Gln Ala Leu Arg Thr Pro Phe Thr Lys Val Gly Ser Thr Cys Ser
                165                 170                 175 ctg aga tta gag att gat gat cct gaa ata gaa ata gtt gag ttt ctt      576
Leu Arg Leu Glu Ile Asp Asp Pro Glu Ile Glu Ile Val Glu Phe Leu
            180                 185                 190 ata ctg gat gag gca gaa aac aaa tgg tac aaa cat aat ggc cag aat      624
Ile Leu Asp Glu Ala Glu Asn Lys Trp Tyr Lys His Asn Gly Gln Asn
        195                 200                 205 ttt caa gtt cat ttg ttg aaa caa ggc tat caa aat caa cat gtt tca      672
Phe Gln Val His Leu Leu Lys Gln Gly Tyr Gln Asn Gln His Val Ser
    210                 215                 220 gtc tct gga aat cca aat atc att gta cct gaa gac ctt gtg cag att      720
Val Ser Gly Asn Pro Asn Ile Ile Val Pro Glu Asp Leu Val Gln Ile
225                 230                 235                 240 caa gcc ttt ctt agg tgg gaa aga aag ggt agg cag aca tat aca cct      768
Gln Ala Phe Leu Arg Trp Glu Arg Lys Gly Arg Gln Thr Tyr Thr Pro
                245                 250                 255 gat caa gaa aag gag gag tat gaa gca gct aga atg gag ctg ata gaa      816
Asp Gln Glu Lys Glu Glu Tyr Glu Ala Ala Arg Met Glu Leu Ile Glu
            260                 265                 270 gaa ata agt aga ggt atg cct gta gag gag ctt cga tcc aag ttg aca      864
Glu Ile Ser Arg Gly Met Pro Val Glu Glu Leu Arg Ser Lys Leu Thr
        275                 280                 285 gag aaa cca gaa gtc aaa tct gga agt aga gaa gag aaa acc cac aga      912
Glu Lys Pro Glu Val Lys Ser Gly Ser Arg Glu Glu Lys Thr His Arg
    290                 295                 300 gta caa agt cac aaa ggt ggg atc tca gat gat ctt gtg caa ata caa      960
Val Gln Ser His Lys Gly Gly Ile Ser Asp Asp Leu Val Gln Ile Gln
305                 310                 315                 320 gca ttc atc cga tgg gag aaa gct ggg aaa cca aac tac cct cca gag      1008
Ala Phe Ile Arg Trp Glu Lys Ala Gly Lys Pro Asn Tyr Pro Pro Glu
                325                 330                 335 aag caa ctt atg gag ttt gag gaa gca agg aaa gag ctg cag ctt gag      1056
Lys Gln Leu Met Glu Phe Glu Glu Ala Arg Lys Glu Leu Gln Leu Glu
            340                 345                 350 ttt gat aaa ggt act tct ctg gct gaa cta cgg gaa aag atc atg aag      1104
Phe Asp Lys Gly Thr Ser Leu Ala Glu Leu Arg Glu Lys Ile Met Lys
        355                 360                 365 ggg gat ata tca act aaa gtt ttg aag caa ctg aag gtt gaa aag tat      1152
Gly Asp Ile Ser Thr Lys Val Leu Lys Gln Leu Lys Val Glu Lys Tyr
    370                 375                 380 ttc agc aac aaa aga att cag cgg aag gaa agg gac atc atg gaa att      1200
Phe Ser Asn Lys Arg Ile Gln Arg Lys Glu Arg Asp Ile Met Glu Ile
385                 390                 395                 400 ttg aat aaa aaa gtt gca gaa act cta gat gaa aaa tct tct caa ata      1248
Leu Asn Lys Lys Val Ala Glu Thr Leu Asp Glu Lys Ser Ser Gln Ile
                405                 410                 415 gtc act cct cct aca gtg cta gaa ctc ttg gct aag tct ata cat gag      1296
Val Thr Pro Pro Thr Val Leu Glu Leu Leu Ala Lys Ser Ile His Glu
            420                 425                 430 cag gat ggt gaa tca gtt ctg cat cag aaa atc tat aag ctg gat aat      1344
Gln Asp Gly Glu Ser Val Leu His Gln Lys Ile Tyr Lys Leu Asp Asn
        435                 440                 445 aag aat ctt ctg gta cta gta acc aaa cct ttt gaa agg aca aaa gtt      1392
Lys Asn Leu Leu Val Leu Val Thr Lys Pro Phe Glu Arg Thr Lys Val
```

-continued

```
                   450                 455                 460
tat ttg gct aca gat caa agt gaa cca ctt att tta cac tgg gga tta    1440
Tyr Leu Ala Thr Asp Gln Ser Glu Pro Leu Ile Leu His Trp Gly Leu
465                 470                 475                 480 tca agg aaa tca aga gag tgg atg gta ccc cct aca agt tct att cct    1488
Ser Arg Lys Ser Arg Glu Trp Met Val Pro Pro Thr Ser Ser Ile Pro
                485                 490                 495 cca ggt tca gta ttg cta gaa gag tct tgt gaa acc cct ttt act aag    1536
Pro Gly Ser Val Leu Leu Glu Glu Ser Cys Glu Thr Pro Phe Thr Lys
            500                 505                 510 ggt tta atg gta gat cag tat tat cag gcc att caa ata gag att gat    1584
Gly Leu Met Val Asp Gln Tyr Tyr Gln Ala Ile Gln Ile Glu Ile Asp
        515                 520                 525 ggg ggt gat tat gct gga att ccc ttc gtt ctt cgt tca gac gat aaa    1632
Gly Gly Asp Tyr Ala Gly Ile Pro Phe Val Leu Arg Ser Asp Asp Lys
    530                 535                 540 tgg ata aag aat agt ggt ttg gac ttt tac att gag ttg gac gat aga    1680
Trp Ile Lys Asn Ser Gly Leu Asp Phe Tyr Ile Glu Leu Asp Asp Arg
545                 550                 555                 560 agt att agg aag gct cct ggt gat gga agc ggc att gca aaa tca ttg    1728
Ser Ile Arg Lys Ala Pro Gly Asp Gly Ser Gly Ile Ala Lys Ser Leu
                565                 570                 575 ctt gac aag att gct gac ctg gag acc gag gct caa aaa tct ttt atg    1776
Leu Asp Lys Ile Ala Asp Leu Glu Thr Glu Ala Gln Lys Ser Phe Met
            580                 585                 590 cac agg ttt agt att gca gca gat ctc act gag caa gct aga ggc tct    1824
His Arg Phe Ser Ile Ala Ala Asp Leu Thr Glu Gln Ala Arg Gly Ser
        595                 600                 605 ggc cat cta ggg ctt gtt ggc att ctt gtt tgg atg aga ttc atg gca    1872
Gly His Leu Gly Leu Val Gly Ile Leu Val Trp Met Arg Phe Met Ala
    610                 615                 620 atg aga caa ctc att tgg aat aaa aac tac aat gtc aag cca cgt gag    1920
Met Arg Gln Leu Ile Trp Asn Lys Asn Tyr Asn Val Lys Pro Arg Glu
625                 630                 635                 640 att agt aaa gct cag gat agg ctc aca gat ctt ctt cag gac ata tat    1968
Ile Ser Lys Ala Gln Asp Arg Leu Thr Asp Leu Leu Gln Asp Ile Tyr
                645                 650                 655 aaa gac ttc ccc cag tat aga gag atc ttg agg atg atc atg gct act    2016
Lys Asp Phe Pro Gln Tyr Arg Glu Ile Leu Arg Met Ile Met Ala Thr
            660                 665                 670 gtt ggt agg ggc ggt gaa ggt gat gtt ggt cag cgt atc cga gat gaa    2064
Val Gly Arg Gly Gly Glu Gly Asp Val Gly Gln Arg Ile Arg Asp Glu
        675                 680                 685 ata tta gtt ata cag aga aac aat gac tgc aag gga gga atg atg gag    2112
Ile Leu Val Ile Gln Arg Asn Asn Asp Cys Lys Gly Gly Met Met Glu
    690                 695                 700 gaa tgg cat cag aag cta cat aac aac act agc cca gat gat gtt gtg    2160
Glu Trp His Gln Lys Leu His Asn Asn Thr Ser Pro Asp Asp Val Val
705                 710                 715                 720 ata tgc cag gca ctt att gat tat gtt aaa agt gat ttt gac atc agt    2208
Ile Cys Gln Ala Leu Ile Asp Tyr Val Lys Ser Asp Phe Asp Ile Ser
                725                 730                 735 gtg tac tgg gac agt ttg aat aaa aat gga ata acc aag gaa cgt ttg    2256
Val Tyr Trp Asp Ser Leu Asn Lys Asn Gly Ile Thr Lys Glu Arg Leu
            740                 745                 750 ttg agc tat gat cgt gct att cat tct gaa cca agt ttc agg aga gat    2304
Leu Ser Tyr Asp Arg Ala Ile His Ser Glu Pro Ser Phe Arg Arg Asp
        755                 760                 765 cag aaa gaa ggt ctt tta cgt gat cta gga aac tac atg agg acg ttg    2352
Gln Lys Glu Gly Leu Leu Arg Asp Leu Gly Asn Tyr Met Arg Thr Leu
```

```
                770                 775                 780
aag gca gtt cac tct ggt gca gat ctc gag tct gcc att gct acg tgt    2400
Lys Ala Val His Ser Gly Ala Asp Leu Glu Ser Ala Ile Ala Thr Cys
785                 790                 795                 800 atg ggt tac aaa tct gag cgt caa ggc ttt atg gtt ggc gtt caa ata    2448
Met Gly Tyr Lys Ser Glu Arg Gln Gly Phe Met Val Gly Val Gln Ile
                    805                 810                 815 aac ccg ata ggg gga ttg cca tct gga ttc cct ggt cta atg aaa ttc    2496
Asn Pro Ile Gly Gly Leu Pro Ser Gly Phe Pro Gly Leu Met Lys Phe
                820                 825                 830 att cta aaa cat gtt gaa gat aaa aat gtg gag cct ttg ata gag ggg    2544
Ile Leu Lys His Val Glu Asp Lys Asn Val Glu Pro Leu Ile Glu Gly
            835                 840                 845 ttg ctg gag gca cga gtg gaa ctt aga cca ttg ctt ctt agc tct cat    2592
Leu Leu Glu Ala Arg Val Glu Leu Arg Pro Leu Leu Leu Ser Ser His
850                 855                 860 gaa cgg ctg aag gat ctt att ttt ttg gat atc gcc ctt gat tct act    2640
Glu Arg Leu Lys Asp Leu Ile Phe Leu Asp Ile Ala Leu Asp Ser Thr
865                 870                 875                 880 gtc agg aca gct gtt gag aga gga tat gag gaa ttg agt aat gcg gag    2688
Val Arg Thr Ala Val Glu Arg Gly Tyr Glu Glu Leu Ser Asn Ala Glu
                    885                 890                 895 cca gag aaa ctt att tac ctt att atg ctg ctg ctt gag aat ctt gca    2736
Pro Glu Lys Leu Ile Tyr Leu Ile Met Leu Leu Leu Glu Asn Leu Ala
                900                 905                 910 ttg tct aca gat gat aat gag gac ctc ata tat tgc ttg aag gga tgg    2784
Leu Ser Thr Asp Asp Asn Glu Asp Leu Ile Tyr Cys Leu Lys Gly Trp
            915                 920                 925 aaa cat tcg atg gag atg tgt aag caa aaa gat gat caa tgg gca cta    2832
Lys His Ser Met Glu Met Cys Lys Gln Lys Asp Asp Gln Trp Ala Leu
930                 935                 940 ttt gct aag tca ttt ctt gac aga acc cgt ctg gct cta tca agc aag    2880
Phe Ala Lys Ser Phe Leu Asp Arg Thr Arg Leu Ala Leu Ser Ser Lys
945                 950                 955                 960 gca gaa tac tac cat caa att ttg caa cct tca gct gaa tac ctt gga    2928
Ala Glu Tyr Tyr His Gln Ile Leu Gln Pro Ser Ala Glu Tyr Leu Gly
                    965                 970                 975 tca ttg ctt gat gtt gat gca ggg gcg gta agc ata ttc aca gaa gaa    2976
Ser Leu Leu Asp Val Asp Ala Gly Ala Val Ser Ile Phe Thr Glu Glu
                980                 985                 990 atc ata cgt gct gga tca gca gct tct tta tct gca ctt ctt cag cga    3024
Ile Ile Arg Ala Gly Ser Ala Ala Ser Leu Ser Ala Leu Leu Gln Arg
            995                 1000                1005 ctt gac cct ctt ctt cgg aaa gtt gca cat ttg gga agc tgg cag        3069
Leu Asp Pro Leu Leu Arg Lys Val Ala His Leu Gly Ser Trp Gln
    1010                1015                1020 gtc ata agc cct gtt gaa gtt gct gga tat gtt gaa att gta gaa        3114
Val Ile Ser Pro Val Glu Val Ala Gly Tyr Val Glu Ile Val Glu
    1025                1030                1035 gaa ttg ctt gct gtc cag aat aaa tca tat aca caa tca aca att        3159
Glu Leu Leu Ala Val Gln Asn Lys Ser Tyr Thr Gln Ser Thr Ile
    1040                1045                1050 ttg gtt gca aaa cat gta agg gga gaa gag gaa ata cca gat ggc        3204
Leu Val Ala Lys His Val Arg Gly Glu Glu Glu Ile Pro Asp Gly
    1055                1060                1065 aca gtt gct gtt tta aca cct gat atg cca gat gtt cta tct cat        3249
Thr Val Ala Val Leu Thr Pro Asp Met Pro Asp Val Leu Ser His
    1070                1075                1080 gtc tct gtg cga gct aga aat agc aag gta tgt ttt gct acc tgc        3294
Val Ser Val Arg Ala Arg Asn Ser Lys Val Cys Phe Ala Thr Cys
```

```
                 1085              1090              1095
ttt gat gac aat atc ctg gat gag ttt cgg aga aat gca gga aag    3339
Phe Asp Asp Asn Ile Leu Asp Glu Phe Arg Arg Asn Ala Gly Lys
1100              1105              1110 ctt ttt cat cta aag ccc aca tca gat gat att gta tat agt aaa    3384
Leu Phe His Leu Lys Pro Thr Ser Asp Asp Ile Val Tyr Ser Lys
1115              1120              1125 ata gaa aaa act gaa cct gaa gat gtg ggt cca gtt caa gct gga    3429
Ile Glu Lys Thr Glu Pro Glu Asp Val Gly Pro Val Gln Ala Gly
1130              1135              1140 gat gag caa tca ctg cca tct gtg aca ttg gtt agg aag cac ttc    3474
Asp Glu Gln Ser Leu Pro Ser Val Thr Leu Val Arg Lys His Phe
1145              1150              1155 agc ggc aag tac acc ata tca gct gaa gaa ttt acc aat gaa atg    3519
Ser Gly Lys Tyr Thr Ile Ser Ala Glu Glu Phe Thr Asn Glu Met
1160              1165              1170 gtt ggt gct aaa tca cgg aat atc tca ttt cta aaa gga aag gtt    3564
Val Gly Ala Lys Ser Arg Asn Ile Ser Phe Leu Lys Gly Lys Val
1175              1180              1185 cct tca tgg gtg ggc att ccc aca tca gtc gct cta cca ttt gga    3609
Pro Ser Trp Val Gly Ile Pro Thr Ser Val Ala Leu Pro Phe Gly
1190              1195              1200 gtt ttt gaa gaa gtt ctg tca aat gac ata aac aag gaa att gcc    3654
Val Phe Glu Glu Val Leu Ser Asn Asp Ile Asn Lys Glu Ile Ala
1205              1210              1215 agc cag ctg cag tta ctg aaa gag aag ttg gct atc gga gaa ttc    3699
Ser Gln Leu Gln Leu Leu Lys Glu Lys Leu Ala Ile Gly Glu Phe
1220              1225              1230 aat gca ctt ctc gac ata aga aag atg atc ttg cag cta gca tct    3744
Asn Ala Leu Leu Asp Ile Arg Lys Met Ile Leu Gln Leu Ala Ser
1235              1240              1245 cca att gag ttg gta caa gag cta aag gga aaa atg cag gca tca    3789
Pro Ile Glu Leu Val Gln Glu Leu Lys Gly Lys Met Gln Ala Ser
1250              1255              1260 gga atg cca tgg cct ggt gat gag ggt gaa gat cgg tgg gaa ctt    3834
Gly Met Pro Trp Pro Gly Asp Glu Gly Glu Asp Arg Trp Glu Leu
1265              1270              1275 gct tgg atg gca ata aaa aga gtt tgg gct tca aag tgg aat gag    3879
Ala Trp Met Ala Ile Lys Arg Val Trp Ala Ser Lys Trp Asn Glu
1280              1285              1290 aga gca tat ttc agc aca agg aaa gtc aag ttg gat cat gac tat    3924
Arg Ala Tyr Phe Ser Thr Arg Lys Val Lys Leu Asp His Asp Tyr
1295              1300              1305 ttg tgc atg gct gtc ttg gtt caa gaa atc att agt gct gat tat    3969
Leu Cys Met Ala Val Leu Val Gln Glu Ile Ile Ser Ala Asp Tyr
1310              1315              1320 gca ttt gtc atc cac act aca aac cca tca tct gga gac tca tct    4014
Ala Phe Val Ile His Thr Thr Asn Pro Ser Ser Gly Asp Ser Ser
1325              1330              1335 gaa ata tat gcc gag gtg gtg aaa gga ctc gga gaa act ctt gtt    4059
Glu Ile Tyr Ala Glu Val Val Lys Gly Leu Gly Glu Thr Leu Val
1340              1345              1350 gga gcc tat cca ggc cgg gca ttg agc ttc gtc tgt aat aag aac    4104
Gly Ala Tyr Pro Gly Arg Ala Leu Ser Phe Val Cys Asn Lys Asn
1355              1360              1365 aat ctg aac tcg cca aag gta ctt ggt ttc cca agc aag cct att    4149
Asn Leu Asn Ser Pro Lys Val Leu Gly Phe Pro Ser Lys Pro Ile
1370              1375              1380 ggc ctc ttc atc aaa cga tca att atc ttc aga tct gat tct aat    4194
Gly Leu Phe Ile Lys Arg Ser Ile Ile Phe Arg Ser Asp Ser Asn
```

```
                1385                1390                1395
gtt gaa gat tta gaa ggt tat gca ggt gct ggt ctt tat gac agt                4239
Gly Glu Asp Leu Glu Gly Tyr Ala Gly Ala Gly Leu Tyr Asp Ser
1400                1405                1410 gtg ccc atg gat gag gaa gag aaa gtg gta ctc gac tat gta gct                4284
Val Pro Met Asp Glu Glu Glu Lys Val Val Leu Asp Tyr Val Ala
    1415                1420                1425 gac ccg tta atc atg gat aag aac ttc cgt aat tca ctg ctc tcc                4329
Asp Pro Leu Ile Met Asp Lys Asn Phe Arg Asn Ser Leu Leu Ser
1430                1435                1440 agc att gct cga gca ggt tat gcg atc gag gag ctc tat ggc tct                4374
Ser Ile Ala Arg Ala Gly Tyr Ala Ile Glu Glu Leu Tyr Gly Ser
    1445                1450                1455 cca cag gac att gaa ggt gtt gta aag gat ggt aaa atc ttc gtc                4419
Pro Gln Asp Ile Glu Gly Val Val Lys Asp Gly Lys Ile Phe Val
1460                1465                1470 gtc caa aca aga cca cag atg tga                                            4443
Val Gln Thr Arg Pro Gln Met
    1475                1480

<210> SEQ ID NO 4
<211> LENGTH: 1480
<212> TYPE: PRT
<213> ORGANISM: Curcuma longa

<400> SEQUENCE: 4

Met Asn Asn Cys Val Gly His Thr Leu Pro Gln Gln Ala Leu Phe Arg
1               5                   10                  15

Pro Ser Val Val Glu Arg His Asn Thr Ala Cys Gln Arg Ser Ser Gly
                20                  25                  30

Asn Ile Leu Cys Thr Val Pro Ser Ala Ser Lys Ala Glu Asp Val Pro
            35                  40                  45

Ser Leu Lys Pro Phe Leu Ser Ser Arg Phe Leu Gly Lys Thr Pro Tyr
        50                  55                  60

Ala Gly Lys Gly Asn Pro Leu Lys Lys Asn Leu Arg Thr Val Thr Met
65                  70                  75                  80

Ser Pro Gln Ala Leu Leu Ala Ala Asp Pro Ala Ser Glu Leu Ala Arg
                85                  90                  95

Lys Phe Lys Leu Asp Thr Asn Ser Glu Leu Glu Val Thr Ile Cys Lys
            100                 105                 110

Pro Thr Ser Glu Ser Pro Met Gln Ile Asp Phe Gln Val Thr Asn Val
        115                 120                 125

Ser Gly Ser Leu Val Leu His Trp Gly Val Ile Leu Gln Thr Arg Arg
    130                 135                 140

Glu Trp Ser Leu Pro Ser His Tyr Pro Glu Gly Thr Lys Val Tyr Lys
145                 150                 155                 160

Asn Gln Ala Leu Arg Thr Pro Phe Thr Lys Val Gly Ser Thr Cys Ser
                165                 170                 175

Leu Arg Leu Glu Ile Asp Asp Pro Glu Ile Glu Ile Val Glu Phe Leu
            180                 185                 190

Ile Leu Asp Glu Ala Glu Asn Lys Trp Tyr Lys His Asn Gly Gln Asn
        195                 200                 205

Phe Gln Val His Leu Leu Lys Gln Gly Tyr Gln Asn Gln His Val Ser
    210                 215                 220

Val Ser Gly Asn Pro Asn Ile Ile Val Pro Glu Asp Leu Val Gln Ile
225                 230                 235                 240

Gln Ala Phe Leu Arg Trp Glu Arg Lys Gly Arg Gln Thr Tyr Thr Pro
```

```
                    245                 250                 255
Asp Gln Glu Lys Glu Glu Tyr Glu Ala Ala Arg Met Glu Leu Ile Glu
            260                 265                 270

Glu Ile Ser Arg Gly Met Pro Val Glu Leu Arg Ser Lys Leu Thr
            275                 280                 285

Glu Lys Pro Glu Val Lys Ser Gly Arg Glu Lys Thr His Arg
            290                 295                 300

Val Gln Ser His Lys Gly Gly Ile Ser Asp Asp Leu Val Gln Ile Gln
305                 310                 315                 320

Ala Phe Ile Arg Trp Glu Lys Ala Gly Lys Pro Asn Tyr Pro Pro Glu
                325                 330                 335

Lys Gln Leu Met Glu Phe Glu Ala Arg Lys Glu Leu Gln Leu Glu
            340                 345                 350

Phe Asp Lys Gly Thr Ser Leu Ala Glu Leu Arg Glu Lys Ile Met Lys
            355                 360                 365

Gly Asp Ile Ser Thr Lys Val Leu Lys Gln Leu Lys Val Glu Lys Tyr
    370                 375                 380

Phe Ser Asn Lys Arg Ile Gln Arg Lys Glu Arg Asp Ile Met Glu Ile
385                 390                 395                 400

Leu Asn Lys Lys Val Ala Glu Thr Leu Asp Glu Lys Ser Ser Gln Ile
                405                 410                 415

Val Thr Pro Pro Thr Val Leu Glu Leu Leu Ala Lys Ser Ile His Glu
                420                 425                 430

Gln Asp Gly Glu Ser Val Leu His Gln Lys Ile Tyr Lys Leu Asp Asn
            435                 440                 445

Lys Asn Leu Leu Val Leu Val Thr Lys Pro Phe Glu Arg Thr Lys Val
    450                 455                 460

Tyr Leu Ala Thr Asp Gln Ser Glu Pro Leu Ile Leu His Trp Gly Leu
465                 470                 475                 480

Ser Arg Lys Ser Arg Glu Trp Met Val Pro Thr Ser Ser Ile Pro
                485                 490                 495

Pro Gly Ser Val Leu Leu Glu Glu Ser Cys Glu Thr Pro Phe Thr Lys
            500                 505                 510

Gly Leu Met Val Asp Gln Tyr Tyr Gln Ala Ile Gln Ile Glu Ile Asp
            515                 520                 525

Gly Gly Asp Tyr Ala Gly Ile Pro Phe Val Leu Arg Ser Asp Asp Lys
            530                 535                 540

Trp Ile Lys Asn Ser Gly Leu Asp Phe Tyr Ile Glu Leu Asp Asp Arg
545                 550                 555                 560

Ser Ile Arg Lys Ala Pro Gly Asp Gly Ser Gly Ile Ala Lys Ser Leu
                565                 570                 575

Leu Asp Lys Ile Ala Asp Leu Glu Thr Glu Ala Gln Lys Ser Phe Met
            580                 585                 590

His Arg Phe Ser Ile Ala Ala Asp Leu Thr Glu Gln Ala Arg Gly Ser
            595                 600                 605

Gly His Leu Gly Leu Val Gly Ile Leu Val Trp Met Arg Phe Met Ala
    610                 615                 620

Met Arg Gln Leu Ile Trp Asn Lys Asn Tyr Asn Val Lys Pro Arg Glu
625                 630                 635                 640

Ile Ser Lys Ala Gln Asp Arg Leu Thr Asp Leu Leu Gln Asp Ile Tyr
                645                 650                 655

Lys Asp Phe Pro Gln Tyr Arg Glu Ile Leu Arg Met Ile Met Ala Thr
            660                 665                 670
```

-continued

Val Gly Arg Gly Gly Glu Gly Asp Val Gly Gln Arg Ile Arg Asp Glu
            675                 680                 685

Ile Leu Val Ile Gln Arg Asn Asn Asp Cys Lys Gly Gly Met Met Glu
    690                 695                 700

Glu Trp His Gln Lys Leu His Asn Asn Thr Ser Pro Asp Asp Val Val
705                 710                 715                 720

Ile Cys Gln Ala Leu Ile Asp Tyr Val Lys Ser Asp Phe Asp Ile Ser
            725                 730                 735

Val Tyr Trp Asp Ser Leu Asn Lys Asn Gly Ile Thr Lys Glu Arg Leu
            740                 745                 750

Leu Ser Tyr Asp Arg Ala Ile His Ser Glu Pro Ser Phe Arg Arg Asp
            755                 760                 765

Gln Lys Glu Gly Leu Leu Arg Asp Leu Gly Asn Tyr Met Arg Thr Leu
    770                 775                 780

Lys Ala Val His Ser Gly Ala Asp Leu Glu Ser Ala Ile Ala Thr Cys
785                 790                 795                 800

Met Gly Tyr Lys Ser Glu Arg Gln Gly Phe Met Val Gly Val Gln Ile
            805                 810                 815

Asn Pro Ile Gly Gly Leu Pro Ser Gly Phe Pro Gly Leu Met Lys Phe
            820                 825                 830

Ile Leu Lys His Val Glu Asp Lys Asn Val Glu Pro Leu Ile Glu Gly
            835                 840                 845

Leu Leu Glu Ala Arg Val Glu Leu Arg Pro Leu Leu Leu Ser Ser His
    850                 855                 860

Glu Arg Leu Lys Asp Leu Ile Phe Leu Asp Ile Ala Leu Asp Ser Thr
865                 870                 875                 880

Val Arg Thr Ala Val Glu Arg Gly Tyr Glu Glu Leu Ser Asn Ala Glu
            885                 890                 895

Pro Glu Lys Leu Ile Tyr Leu Ile Met Leu Leu Leu Glu Asn Leu Ala
            900                 905                 910

Leu Ser Thr Asp Asp Asn Glu Asp Leu Ile Tyr Cys Leu Lys Gly Trp
    915                 920                 925

Lys His Ser Met Glu Met Cys Lys Gln Lys Asp Asp Gln Trp Ala Leu
930                 935                 940

Phe Ala Lys Ser Phe Leu Asp Arg Thr Arg Leu Ala Leu Ser Ser Lys
945                 950                 955                 960

Ala Glu Tyr Tyr His Gln Ile Leu Gln Pro Ser Ala Glu Tyr Leu Gly
            965                 970                 975

Ser Leu Leu Asp Val Asp Ala Gly Ala Val Ser Ile Phe Thr Glu Glu
            980                 985                 990

Ile Ile Arg Ala Gly Ser Ala Ala Ser Leu Ser Ala Leu Leu Gln Arg
            995                1000                1005

Leu Asp Pro Leu Leu Arg Lys Val Ala His Leu Gly Ser Trp Gln
    1010                1015                1020

Val Ile Ser Pro Val Glu Val Ala Gly Tyr Val Glu Ile Val Glu
    1025                1030                1035

Glu Leu Leu Ala Val Gln Asn Lys Ser Tyr Thr Gln Ser Thr Ile
    1040                1045                1050

Leu Val Ala Lys His Val Arg Gly Glu Glu Glu Ile Pro Asp Gly
    1055                1060                1065

Thr Val Ala Val Leu Thr Pro Asp Met Pro Asp Val Leu Ser His
    1070                1075                1080

Val Ser Val Arg Ala Arg Asn Ser Lys Val Cys Phe Ala Thr Cys
    1085                1090                1095

```
Phe Asp Asp Asn Ile Leu Asp  Glu Phe Arg Arg Asn  Ala Gly Lys
    1100            1105              1110
Leu Phe His Leu Lys Pro Thr  Ser Asp Asp Ile Val  Tyr Ser Lys
    1115            1120              1125
Ile Glu Lys Thr Glu Pro Glu  Asp Val Gly Pro Val  Gln Ala Gly
    1130            1135              1140
Asp Glu Gln Ser Leu Pro Ser  Val Thr Leu Val Arg  Lys His Phe
    1145            1150              1155
Ser Gly Lys Tyr Thr Ile Ser  Ala Glu Glu Phe Thr  Asn Glu Met
    1160            1165              1170
Val Gly Ala Lys Ser Arg Asn  Ile Ser Phe Leu Lys  Gly Lys Val
    1175            1180              1185
Pro Ser Trp Val Gly Ile Pro  Thr Ser Val Ala Leu  Pro Phe Gly
    1190            1195              1200
Val Phe Glu Glu Val Leu Ser  Asn Asp Ile Asn Lys  Glu Ile Ala
    1205            1210              1215
Ser Gln Leu Gln Leu Leu Lys  Glu Lys Leu Ala Ile  Gly Glu Phe
    1220            1225              1230
Asn Ala Leu Leu Asp Ile Arg  Lys Met Ile Leu Gln  Leu Ala Ser
    1235            1240              1245
Pro Ile Glu Leu Val Gln Glu  Leu Lys Gly Lys Met  Gln Ala Ser
    1250            1255              1260
Gly Met Pro Trp Pro Gly Asp  Glu Gly Glu Asp Arg  Trp Glu Leu
    1265            1270              1275
Ala Trp Met Ala Ile Lys Arg  Val Trp Ala Ser Lys  Trp Asn Glu
    1280            1285              1290
Arg Ala Tyr Phe Ser Thr Arg  Lys Val Lys Leu Asp  His Asp Tyr
    1295            1300              1305
Leu Cys Met Ala Val Leu Val  Gln Glu Ile Ile Ser  Ala Asp Tyr
    1310            1315              1320
Ala Phe Val Ile His Thr Thr  Asn Pro Ser Ser Gly  Asp Ser Ser
    1325            1330              1335
Glu Ile Tyr Ala Glu Val Val  Lys Gly Leu Gly Glu  Thr Leu Val
    1340            1345              1350
Gly Ala Tyr Pro Gly Arg Ala  Leu Ser Phe Val Cys  Asn Lys Asn
    1355            1360              1365
Asn Leu Asn Ser Pro Lys Val  Leu Gly Phe Pro Ser  Lys Pro Ile
    1370            1375              1380
Gly Leu Phe Ile Lys Arg Ser  Ile Ile Phe Arg Ser  Asp Ser Asn
    1385            1390              1395
Gly Glu Asp Leu Glu Gly Tyr  Ala Gly Ala Gly Leu  Tyr Asp Ser
    1400            1405              1410
Val Pro Met Asp Glu Glu Glu  Lys Val Val Leu Asp  Tyr Val Ala
    1415            1420              1425
Asp Pro Leu Ile Met Asp Lys  Asn Phe Arg Asn Ser  Leu Leu Ser
    1430            1435              1440
Ser Ile Ala Arg Ala Gly Tyr  Ala Ile Glu Glu Leu  Tyr Gly Ser
    1445            1450              1455
Pro Gln Asp Ile Glu Gly Val  Val Lys Asp Gly Lys  Ile Phe Val
    1460            1465              1470
Val Gln Thr Arg Pro Gln Met
    1475            1480
```

```
<210> SEQ ID NO 5
<211> LENGTH: 3000
<212> TYPE: DNA
<213> ORGANISM: Triticum aestivum
<220> FEATURE:
<221> NAME/KEY: CDS
<222> LOCATION: (227)..(2623)

<400> SEQUENCE: 5
ctccaccgcg gtggcggccg ctctagaact agtggatccc ccgggctgca ggaattcggc      60
acgagcttcg gcctgacccc gttcgtttac ccccacacag agcacactcc agtccagtcc     120
agcccactgc caccgcgcta ctctccactc ccactgccac cacctccgcc tgcgccgcgc     180
tctgggcgga ccaacccgcg aaccgtacca tctcccgccc cgatcc atg tcg tcg        235
                                                    Met Ser Ser
                                                     1 gcg gtc gcg tcc gcc gca tcc ttc ctc gcg ctc gcg tca gcc tcc ccc       283
Ala Val Ala Ser Ala Ala Ser Phe Leu Ala Leu Ala Ser Ala Ser Pro
  5                  10                  15 ggg aga tca cgc agg cgg gcg agg gtg agc gcg cag cca ccc cac gcc       331
Gly Arg Ser Arg Arg Arg Ala Arg Val Ser Ala Gln Pro Pro His Ala
 20                  25                  30                  35 ggg gcc ggc agg ttg cac tgg ccg ccg tgg ccg ccg cag cgc acg gct       379
Gly Ala Gly Arg Leu His Trp Pro Pro Trp Pro Pro Gln Arg Thr Ala
                 40                  45                  50 cgc gac gga gct gtg gcg gcg ctc gcc gcc ggg aag aag gac gcg ggg       427
Arg Asp Gly Ala Val Ala Ala Leu Ala Ala Gly Lys Lys Asp Ala Gly
             55                  60                  65 atc gac gac gcc gcc gcg tcc gtg agg cag ccc cgc gca ctc cgc ggt       475
Ile Asp Asp Ala Ala Ala Ser Val Arg Gln Pro Arg Ala Leu Arg Gly
         70                  75                  80 ggc gcc gcc acc aag gtc gcg gag cga agg gat ccc gtc aag acg ctc       523
Gly Ala Ala Thr Lys Val Ala Glu Arg Arg Asp Pro Val Lys Thr Leu
 85                  90                  95 gac cgc gac gcc gcg gaa ggc ggc ggg ccg tcc ccg ccg gca gcg agg       571
Asp Arg Asp Ala Ala Glu Gly Gly Gly Pro Ser Pro Pro Ala Ala Arg
100                 105                 110                 115 cag gac gcc gcc cgt ccg ccg agt atg aac ggc atg ccg gtg aac ggc       619
Gln Asp Ala Ala Arg Pro Pro Ser Met Asn Gly Met Pro Val Asn Gly
                120                 125                 130 gag aac aaa tct acc ggc ggc ggc gcg act aaa gac agc ggg ctg           667
Glu Asn Lys Ser Thr Gly Gly Gly Ala Thr Lys Asp Ser Gly Leu
            135                 140                 145 ccc acg ccc gca cgc gcg ccc cat ccg tcg acc cag aac aga gca ccg       715
Pro Thr Pro Ala Arg Ala Pro His Pro Ser Thr Gln Asn Arg Ala Pro
        150                 155                 160 gtg aac ggt gaa aac aaa gct aac gtc gcc tcg ccg ccg acg agc ata       763
Val Asn Gly Glu Asn Lys Ala Asn Val Ala Ser Pro Pro Thr Ser Ile
    165                 170                 175 gcc gag gcc gcg gct tcg gat tcc gca gct acc att tcc atc agc gac       811
Ala Glu Ala Ala Ala Ser Asp Ser Ala Ala Thr Ile Ser Ile Ser Asp
180                 185                 190                 195 aag gcg ccg gag tcc gtt gtc cca gct gag aag acg ccg ccg tcg tcc       859
Lys Ala Pro Glu Ser Val Val Pro Ala Glu Lys Thr Pro Pro Ser Ser
                200                 205                 210 ggc tca aat ttc gag tcc tcg gcc tct gct ccc ggg tct gac act gtc       907
Gly Ser Asn Phe Glu Ser Ser Ala Ser Ala Pro Gly Ser Asp Thr Val
            215                 220                 225 agc gac gtg gaa caa gaa ctg aag aag ggt gcg gtc gtt gtc gaa gaa       955
Ser Asp Val Glu Gln Glu Leu Lys Lys Gly Ala Val Val Val Glu Glu
        230                 235                 240
```

```
                                            -continued
gct cca aag cca aag gct ctt tcg ccg cct gca gcc ccc gct gta caa     1003
Ala Pro Lys Pro Lys Ala Leu Ser Pro Pro Ala Ala Pro Ala Val Gln
245             250                 255 gaa gac ctt tgg gat ttc aag aaa tac att ggt ttc gag gag ccc gtg     1051
Glu Asp Leu Trp Asp Phe Lys Lys Tyr Ile Gly Phe Glu Glu Pro Val
260             265                 270                 275 gag gcc aag gat gat ggc cgg gct gtc gca gat gat gcg ggc tcc ttt     1099
Glu Ala Lys Asp Asp Gly Arg Ala Val Ala Asp Asp Ala Gly Ser Phe
                280                 285                 290 gaa cac cac cag aat cac gac tcc gga cct ttg gca ggg gag aat gtc     1147
Glu His His Gln Asn His Asp Ser Gly Pro Leu Ala Gly Glu Asn Val
295             300                 305 atg aac gtg gtc gtg gtg gct gct gag tgt tct ccc tgg tgc aaa aca     1195
Met Asn Val Val Val Val Ala Ala Glu Cys Ser Pro Trp Cys Lys Thr
        310                 315                 320 ggt ggt ctg gga gat gtt gcg ggt gct ctg ccc aag gct ttg gca aag     1243
Gly Gly Leu Gly Asp Val Ala Gly Ala Leu Pro Lys Ala Leu Ala Lys
325             330                 335 aga gga cat cgt gtt atg gtt gtg gta cca agg tat ggg gac tat gaa     1291
Arg Gly His Arg Val Met Val Val Val Pro Arg Tyr Gly Asp Tyr Glu
340             345                 350                 355 gaa gcc tac gat gtc gga gtc cga aaa tac tac aag gct gct gga cag     1339
Glu Ala Tyr Asp Val Gly Val Arg Lys Tyr Tyr Lys Ala Ala Gly Gln
                360                 365                 370 gat atg gaa gtg aat tat ttc cat gct tat atc gat gga gtt gat ttt     1387
Asp Met Glu Val Asn Tyr Phe His Ala Tyr Ile Asp Gly Val Asp Phe
                375                 380                 385 gtg ttc att gac gct cct ctc ttc cga cac cgt cag gaa gac att tat     1435
Val Phe Ile Asp Ala Pro Leu Phe Arg His Arg Gln Glu Asp Ile Tyr
        390                 395                 400 ggg ggc agc aga cag gaa att atg aag cgc atg att ttg ttc tgc aag     1483
Gly Gly Ser Arg Gln Glu Ile Met Lys Arg Met Ile Leu Phe Cys Lys
405             410                 415 gcc gct gtt gag gtt cca tgg cac gtt cca tgc ggc ggt gtc cct tat     1531
Ala Ala Val Glu Val Pro Trp His Val Pro Cys Gly Gly Val Pro Tyr
420             425                 430                 435 ggg gat gga aat ctg gtg ttt att gca aat gat tgg cac acg gca ctc     1579
Gly Asp Gly Asn Leu Val Phe Ile Ala Asn Asp Trp His Thr Ala Leu
                440                 445                 450 ctg cct gtc tat ctg aaa gca tat tac agg gac cat ggt ttg atg cag     1627
Leu Pro Val Tyr Leu Lys Ala Tyr Tyr Arg Asp His Gly Leu Met Gln
                455                 460                 465 tac act cgg tcc att atg gtg ata cat aac atc gct cac cag ggc cgt     1675
Tyr Thr Arg Ser Ile Met Val Ile His Asn Ile Ala His Gln Gly Arg
        470                 475                 480 ggc cct gta gat gaa ttc ccg ttc acc gag ttg cct gag cac tac ctg     1723
Gly Pro Val Asp Glu Phe Pro Phe Thr Glu Leu Pro Glu His Tyr Leu
485             490                 495 gaa cac ttc aga ctg tac gac ccc gtg ggt ggt gaa cac gcc aac tac     1771
Glu His Phe Arg Leu Tyr Asp Pro Val Gly Gly Glu His Ala Asn Tyr
500             505                 510                 515 ttc gcc gcc ggc ctg aag atg gcg gac cag gtt gtc gtg gtg agc ccc     1819
Phe Ala Ala Gly Leu Lys Met Ala Asp Gln Val Val Val Val Ser Pro
                520                 525                 530 ggg tac ctg tgg gag ctg aag acg gtg gag ggc ggc tgg ggg ctt cac     1867
Gly Tyr Leu Trp Glu Leu Lys Thr Val Glu Gly Gly Trp Gly Leu His
                535                 540                 545 gac atc ata cgg cag aac gac tgg aag acc cgc ggc atc gtc aac ggc     1915
Asp Ile Ile Arg Gln Asn Asp Trp Lys Thr Arg Gly Ile Val Asn Gly
            550                 555                 560
```

```
atc gac aac atg gag tgg aac ccc gag gtg gac gcc cac ctc aag tcg     1963
Ile Asp Asn Met Glu Trp Asn Pro Glu Val Asp Ala His Leu Lys Ser
565                 570                 575 gac ggc tac acc aac ttc tcc ctg agg acg ctg gac tcc ggc aag cgg     2011
Asp Gly Tyr Thr Asn Phe Ser Leu Arg Thr Leu Asp Ser Gly Lys Arg
580                 585                 590                 595 cag tgc aag gag gcc ctg cag cgc gag ctg ggc ctg cag gtc cgc gcc     2059
Gln Cys Lys Glu Ala Leu Gln Arg Glu Leu Gly Leu Gln Val Arg Ala
                600                 605                 610 gac gtg ccg ctg ctc ggc ttc atc ggc cgc ctg gac ggg cag aag ggc     2107
Asp Val Pro Leu Leu Gly Phe Ile Gly Arg Leu Asp Gly Gln Lys Gly
            615                 620                 625 gtg gag atc atc gcg gac gcc atg ccc tgg atc gtg agc cag gac gtg     2155
Val Glu Ile Ile Ala Asp Ala Met Pro Trp Ile Val Ser Gln Asp Val
630                 635                 640 cag ctg gtg atg ctg ggc acc ggg cgc cac gac ctg gag agc atg ctg     2203
Gln Leu Val Met Leu Gly Thr Gly Arg His Asp Leu Glu Ser Met Leu
645                 650                 655 cag cac ttc gag cgg gag cac cac gac aag gtg cgc ggg tgg gtg ggg     2251
Gln His Phe Glu Arg Glu His His Asp Lys Val Arg Gly Trp Val Gly
660                 665                 670                 675 ttc tcc gtg cgc ctg gcg cac cgg atc acg gcg ggg gcg gac gcg ctc     2299
Phe Ser Val Arg Leu Ala His Arg Ile Thr Ala Gly Ala Asp Ala Leu
                680                 685                 690 ctc atg ccc tcc cgg ttc gag ccg tgc ggg ctg aac cag ctc tac gcc     2347
Leu Met Pro Ser Arg Phe Glu Pro Cys Gly Leu Asn Gln Leu Tyr Ala
            695                 700                 705 atg gcc tac ggc acc gtc ccc gtc gtg cac gcc gtc ggc ggc ctc agg     2395
Met Ala Tyr Gly Thr Val Pro Val Val His Ala Val Gly Gly Leu Arg
710                 715                 720 gac acc gtg ccg ccg ttc gac ccc ttc aac cac tcc ggg ctc ggg tgg     2443
Asp Thr Val Pro Pro Phe Asp Pro Phe Asn His Ser Gly Leu Gly Trp
725                 730                 735 acg ttc gac cgc gcc gag gcg cac aag ctg atc gag gcg ctc ggg cac     2491
Thr Phe Asp Arg Ala Glu Ala His Lys Leu Ile Glu Ala Leu Gly His
740                 745                 750                 755 tgc ctc cgc acc tac cga gac ttc aag gag agc tgg agg gcc ctc cag     2539
Cys Leu Arg Thr Tyr Arg Asp Phe Lys Glu Ser Trp Arg Ala Leu Gln
                760                 765                 770 gag cgc ggc atg tcg cag gac ttc agc tgg gag cac gcc gcc aag ctc     2587
Glu Arg Gly Met Ser Gln Asp Phe Ser Trp Glu His Ala Ala Lys Leu
            775                 780                 785 tac gag gac gtc ctc gtc aag gcc aag tac cag tgg tgaacgctag         2633
Tyr Glu Asp Val Leu Val Lys Ala Lys Tyr Gln Trp
790                 795 ctgctagccg ctccagcccc gcatgcgtgc atgacaggat ggaactgcat tgcgcacgca   2693
ggaaagtgcc atggagcgcc ggcatccgcg aagtacagtg acatgaggtg tgtgtggttg   2753
agacgctgat tccaatccgg cccgtagcag agtagagcgg aggtatatgg gaatcttaac   2813
ttggtattgt aatttgttat gttgtgtgca ttattacaat gttgttactt attcttgtta   2873
agtcggaggc caagggcgaa agctagctca catgtctgat ggatgcacgt gccatggttg   2933
gtttggtagc gcagtgcaaa cggcaagaat gggaagtgaa ttcctccctg cttgaaaaaa   2993
aaaaaaa                                                             3000

<210> SEQ ID NO 6
<211> LENGTH: 799
<212> TYPE: PRT
<213> ORGANISM: Triticum aestivum
```

```
<400> SEQUENCE: 6

Met Ser Ser Ala Val Ala Ser Ala Ala Ser Phe Leu Ala Leu Ala Ser
1               5                   10                  15

Ala Ser Pro Gly Arg Ser Arg Arg Ala Arg Val Ser Ala Gln Pro
            20                  25                  30

Pro His Ala Gly Ala Gly Arg Leu His Trp Pro Pro Trp Pro Pro Gln
            35                  40                  45

Arg Thr Ala Arg Asp Gly Ala Val Ala Ala Leu Ala Ala Gly Lys Lys
        50                  55                  60

Asp Ala Gly Ile Asp Asp Ala Ala Ala Ser Val Arg Gln Pro Arg Ala
65                  70                  75                  80

Leu Arg Gly Gly Ala Ala Thr Lys Val Ala Glu Arg Arg Asp Pro Val
                85                  90                  95

Lys Thr Leu Asp Arg Asp Ala Ala Glu Gly Gly Pro Ser Pro Pro
            100                 105                 110

Ala Ala Arg Gln Asp Ala Ala Arg Pro Pro Ser Met Asn Gly Met Pro
            115                 120                 125

Val Asn Gly Glu Asn Lys Ser Thr Gly Gly Gly Ala Thr Lys Asp
130                 135                 140

Ser Gly Leu Pro Thr Pro Ala Arg Ala Pro His Pro Ser Thr Gln Asn
145                 150                 155                 160

Arg Ala Pro Val Asn Gly Glu Asn Lys Ala Asn Val Ala Ser Pro Pro
                165                 170                 175

Thr Ser Ile Ala Glu Ala Ala Ser Asp Ser Ala Ala Thr Ile Ser
            180                 185                 190

Ile Ser Asp Lys Ala Pro Glu Ser Val Val Pro Ala Glu Lys Thr Pro
            195                 200                 205

Pro Ser Ser Gly Ser Asn Phe Glu Ser Ser Ala Ser Ala Pro Gly Ser
210                 215                 220

Asp Thr Val Ser Asp Val Glu Gln Glu Leu Lys Lys Gly Ala Val Val
225                 230                 235                 240

Val Glu Glu Ala Pro Lys Pro Lys Ala Leu Ser Pro Pro Ala Ala Pro
                245                 250                 255

Ala Val Gln Glu Asp Leu Trp Asp Phe Lys Lys Tyr Ile Gly Phe Glu
            260                 265                 270

Glu Pro Val Glu Ala Lys Asp Asp Gly Arg Ala Val Ala Asp Asp Ala
            275                 280                 285

Gly Ser Phe Glu His His Gln Asn His Asp Ser Gly Pro Leu Ala Gly
            290                 295                 300

Glu Asn Val Met Asn Val Val Val Ala Ala Glu Cys Ser Pro Trp
305                 310                 315                 320

Cys Lys Thr Gly Gly Leu Gly Asp Val Ala Gly Ala Leu Pro Lys Ala
            325                 330                 335

Leu Ala Lys Arg Gly His Arg Val Met Val Val Pro Arg Tyr Gly
            340                 345                 350

Asp Tyr Glu Glu Ala Tyr Asp Val Gly Val Arg Lys Tyr Tyr Lys Ala
            355                 360                 365

Ala Gly Gln Asp Met Glu Val Asn Tyr Phe His Ala Tyr Ile Asp Gly
            370                 375                 380

Val Asp Phe Val Phe Ile Asp Ala Pro Leu Phe Arg His Arg Gln Glu
385                 390                 395                 400

Asp Ile Tyr Gly Gly Ser Arg Gln Glu Ile Met Lys Arg Met Ile Leu
            405                 410                 415
```

-continued

Phe Cys Lys Ala Ala Val Glu Val Pro Trp His Val Pro Cys Gly Gly
                420                 425                 430

Val Pro Tyr Gly Asp Gly Asn Leu Val Phe Ile Ala Asn Asp Trp His
        435                 440                 445

Thr Ala Leu Leu Pro Val Tyr Leu Lys Ala Tyr Tyr Arg Asp His Gly
        450                 455                 460

Leu Met Gln Tyr Thr Arg Ser Ile Met Val Ile His Asn Ile Ala His
465                 470                 475                 480

Gln Gly Arg Gly Pro Val Asp Glu Phe Pro Phe Thr Glu Leu Pro Glu
                485                 490                 495

His Tyr Leu Glu His Phe Arg Leu Tyr Asp Pro Val Gly Gly Glu His
            500                 505                 510

Ala Asn Tyr Phe Ala Ala Gly Leu Lys Met Ala Asp Gln Val Val Val
            515                 520                 525

Val Ser Pro Gly Tyr Leu Trp Glu Leu Lys Thr Val Glu Gly Gly Trp
    530                 535                 540

Gly Leu His Asp Ile Ile Arg Gln Asn Asp Trp Lys Thr Arg Gly Ile
545                 550                 555                 560

Val Asn Gly Ile Asp Asn Met Glu Trp Asn Pro Glu Val Asp Ala His
                565                 570                 575

Leu Lys Ser Asp Gly Tyr Thr Asn Phe Ser Leu Arg Thr Leu Asp Ser
                580                 585                 590

Gly Lys Arg Gln Cys Lys Glu Ala Leu Gln Arg Glu Leu Gly Leu Gln
                595                 600                 605

Val Arg Ala Asp Val Pro Leu Leu Gly Phe Ile Gly Arg Leu Asp Gly
    610                 615                 620

Gln Lys Gly Val Glu Ile Ile Ala Asp Ala Met Pro Trp Ile Val Ser
625                 630                 635                 640

Gln Asp Val Gln Leu Val Met Leu Gly Thr Gly Arg His Asp Leu Glu
                645                 650                 655

Ser Met Leu Gln His Phe Glu Arg Glu His His Asp Lys Val Arg Gly
                660                 665                 670

Trp Val Gly Phe Ser Val Arg Leu Ala His Arg Ile Thr Ala Gly Ala
            675                 680                 685

Asp Ala Leu Leu Met Pro Ser Arg Phe Glu Pro Cys Gly Leu Asn Gln
            690                 695                 700

Leu Tyr Ala Met Ala Tyr Gly Thr Val Pro Val Val His Ala Val Gly
705                 710                 715                 720

Gly Leu Arg Asp Thr Val Pro Pro Phe Asp Pro Phe Asn His Ser Gly
                725                 730                 735

Leu Gly Trp Thr Phe Asp Arg Ala Glu Ala His Lys Leu Ile Glu Ala
            740                 745                 750

Leu Gly His Cys Leu Arg Thr Tyr Arg Asp Phe Lys Glu Ser Trp Arg
            755                 760                 765

Ala Leu Gln Glu Arg Gly Met Ser Gln Asp Phe Ser Trp Glu His Ala
            770                 775                 780

Ala Lys Leu Tyr Glu Asp Val Leu Val Lys Ala Lys Tyr Gln Trp
785                 790                 795